US011603369B2

(12) United States Patent
Ly et al.

(10) Patent No.: US 11,603,369 B2
(45) Date of Patent: Mar. 14, 2023

(54) DIVALENT NUCLEOBASE COMPOUNDS AND USES THEREFOR

(71) Applicant: Carnegie Mellon University, Pittsburgh, PA (US)

(72) Inventors: Danith H. Ly, Pittsburgh, PA (US); Shivaji A. Thadke, Pittsburgh, PA (US); Ali Nakhi, Pittsburgh, PA (US); J. Dinithi Rashmini Perera, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 581 days.

(21) Appl. No.: 16/336,210

(22) PCT Filed: Sep. 26, 2017

(86) PCT No.: PCT/US2017/053395
§ 371 (c)(1),
(2) Date: Mar. 25, 2019

(87) PCT Pub. No.: WO2018/058091
PCT Pub. Date: Mar. 29, 2018

(65) Prior Publication Data
US 2020/0024274 A1    Jan. 23, 2020

Related U.S. Application Data

(60) Provisional application No. 62/495,843, filed on Sep. 26, 2016.

(51) Int. Cl.
| C07D 471/04 | (2006.01) |
| C07D 471/14 | (2006.01) |
| C07D 475/08 | (2006.01) |
| C07H 21/04 | (2006.01) |
| C07D 487/04 | (2006.01) |
| C07H 1/06 | (2006.01) |
| G01N 33/53 | (2006.01) |

(52) U.S. Cl.
CPC ......... *C07D 471/04* (2013.01); *C07D 471/14* (2013.01); *C07D 475/08* (2013.01); *C07D 487/04* (2013.01); *C07H 1/06* (2013.01); *C07H 21/04* (2013.01); *G01N 33/5308* (2013.01)

(58) Field of Classification Search
CPC .. C07K 14/003; C07D 471/04; C07D 471/14; C07D 475/08; C07D 487/04
See application file for complete search history.

(56) References Cited

U.S. PATENT DOCUMENTS

| 5,217,866 A | 6/1993 | Summerton et al. |
| 5,623,049 A | 4/1997 | Lobberding et al. |
| 5,955,571 A | 9/1999 | Schwemler et al. |
| 6,225,052 B1 | 5/2001 | Batz et al. |
| 6,228,982 B1 | 5/2001 | Norden et al. |
| 6,355,726 B1 | 3/2002 | Doemling et al. |
| 6,357,163 B1 | 3/2002 | Buchardt et al. |
| 6,441,130 B2 | 8/2002 | Egholm et al. |
| 6,495,663 B1 | 12/2002 | Rothbard et al. |
| 6,965,020 B2 * | 11/2005 | McGall ................. C07H 21/00 536/26.6 |
| 8,053,212 B1 | 11/2011 | Benner |
| 8,389,703 B1 | 3/2013 | Benner et al. |
| 8,507,204 B2 | 8/2013 | Pierce et al. |
| 8,630,809 B2 | 1/2014 | Kleinbaum |
| 8,653,254 B2 | 2/2014 | Umemoto et al. |
| 9,334,496 B2 | 5/2016 | Grandis et al. |
| 9,926,592 B2 | 3/2018 | Armitage et al. |
| 9,951,098 B2 | 4/2018 | Rajendiran et al. |
| 10,093,700 B2 | 10/2018 | Ly et al. |
| 10,160,787 B2 | 12/2018 | Ly et al. |
| 10,221,216 B2 | 3/2019 | Ly et al. |
| 10,370,415 B2 | 8/2019 | Ly et al. |
| 10,851,407 B2 | 12/2020 | Ly et al. |
| 2002/0188101 A1 | 12/2002 | Neilsen et al. |
| 2003/0148277 A1 | 8/2003 | Chiesa et al. |
| 2003/0207804 A1 * | 11/2003 | Manoharan .......... C07K 1/1077 530/324 |
| 2005/0009041 A1 | 1/2005 | Buchardt et al. |
| 2005/0260635 A1 | 11/2005 | Dirks et al. |
| 2006/0160751 A1 | 7/2006 | McGuire |
| 2011/0028337 A1 | 2/2011 | Bradley et al. |
| 2011/0268810 A1 | 11/2011 | Saltzman et al. |
| 2011/0294687 A1 | 12/2011 | Kleinbaum |
| 2014/0128570 A1 | 5/2014 | Ly et al. |
| 2014/0206744 A1 | 7/2014 | Kleinbaum et al. |
| 2016/0083433 A1 | 3/2016 | Ly et al. |
| 2016/0083434 A1 | 3/2016 | Ly et al. |
| 2016/0264614 A1 | 9/2016 | Conlee et al. |
| 2017/0058325 A1 | 3/2017 | Ly et al. |
| 2017/0121454 A1 | 5/2017 | Saltzman et al. |
| 2017/0136131 A1 | 5/2017 | Roy et al. |
| 2017/0283830 A1 | 10/2017 | Saltzman et al. |
| 2017/0362238 A1 | 12/2017 | Chen et al. |
| 2019/0337986 A1 | 11/2019 | Ly et al. |
| 2020/0087350 A1 | 3/2020 | Ly et al. |
| 2020/0308590 A1 | 10/2020 | Glazer et al. |
| 2020/0340044 A1 | 10/2020 | Ly et al. |

FOREIGN PATENT DOCUMENTS

| EP | 0968309 B1 | 10/2004 |
| EP | 2561891 A2 | 2/2013 |
| WO | 9852614 A2 | 11/1998 |
| WO | 02053574 A2 | 7/2002 |
| WO | 2004024757 A2 | 3/2004 |

(Continued)

OTHER PUBLICATIONS

Gangadhar et al. Organic Letters 2000, vol. 2, No. 18, pp. 2825-2828 (Year: 2000).*

(Continued)

*Primary Examiner* — Jezia Riley
(74) *Attorney, Agent, or Firm* — The Webb Law Firm

(57) ABSTRACT

Described herein are divalent nucleobases that each binds two nucleic acid strands, matched or mismatched when incorporated into a nucleic acid or nucleic acid analog backbone, such as in a γ-peptide nucleic acid (γPNA). Also provided are genetic recognition reagents comprising one or more of the divalent nucleobases and a nucleic acid or nucleic acid analog backbone, such as a γPNA backbone. Uses for the divalent nucleobases and monomers and genetic recognition reagents containing the divalent nucleobases also are provided.

19 Claims, 13 Drawing Sheets

(56) References Cited

FOREIGN PATENT DOCUMENTS

| WO | 2008061091 | A2 | | 5/2008 | |
| WO | 2011116085 | A1 | | 9/2011 | |
| WO | 2012135405 | A1 | | 10/2012 | |
| WO | 2012138955 | A2 | | 10/2012 | |
| WO | 2013074601 | A1 | | 5/2013 | |
| WO | 2013082529 | A1 | | 6/2013 | |
| WO | 2014169206 | A2 | | 10/2014 | |
| WO | 2014169216 | A2 | | 10/2014 | |
| WO | WO-2014169206 | A2 | * | 10/2014 | ............ C07H 21/04 |
| WO | 2015139051 | A2 | | 9/2015 | |
| WO | 2015172058 | A1 | | 11/2015 | |
| WO | 2016081522 | A1 | | 5/2016 | |
| WO | 2017143042 | A2 | | 8/2017 | |
| WO | 2017143061 | A1 | | 8/2017 | |
| WO | 2017151623 | A1 | | 9/2017 | |
| WO | 2017197128 | A1 | | 11/2017 | |
| WO | 2019126646 | A1 | | 6/2019 | |

OTHER PUBLICATIONS

Adelman, "Molecular Computation of Solutions to Combinatorial Problems", Science, 1994, pp. 1021-1024, vol. 266.
Aldaye et al., "Assembling Materials with DNA as the Guide", Science, 2008, pp. 1795-1799, vol. 321.
Asadi et al., "Janus-AT Bases: Synthesis, Self-Assembly, and Solid State Structures", Journal of Organic Chemistry, 2007, pp. 466-475, vol. 72.
Ashley, "Modeling, Synthesis, and Hybridization Properties of (L)-Ribonucleic Acid", Journal of the American Chemical Society, 1992, pp. 9731-9736, vol. 114, No. 25.
Avitabile et al., "γ sulphate PNA (PNA S): Highly Selective DNA Binding Molecule Showing Promising Antigene Activity", PLoS One, 2012, 10 pages, vol. 7, Issue 5, Article No. e35774.
Bahal et al., "Sequence-Unrestricted, Watson-Crick Recognition of Double Helical B-DNA by (R)-MiniPEG-γPNAs", ChemBioChem, 2012, pp. 56-60, vol. 13.
Bahal et al., "Single-Stranded γPNAs for In Vivo Site-Specific Genome Editing via Watson-Crick Recognition", Current Gene Therapy, 2014, pp. 331-342, vol. 14, No. 5.
Ban et al., "The Complete Atomic Structure of the Large Ribosomal Subunit at 2.4 Å Resolution", Science, 2000, pp. 904-920, vol. 289.
Bath et al., "DNA nanomachines", Nature Nanotechnology, 2007, pp. 275-284, vol. 2.
Beck et al., "Peptide Nucleic Acid (PNA): a DNA Mimic with a Pseudopeptide Backbone", 2003, 24 pages, CRC Press LLC.
Berry et al., "Crystal structure of the HCV IRES central domain reveals strategy for start-codon positioning", Structure, 2011, pp. 1456-1466, vol. 19, No. 10.
Braasch et al., "Synthesis, Analysis, Purification, and Intracellular Delivery of Peptide Nucleic Acids", Methods, 2001, pp. 97-107, vol. 23.
Bryan et al., "Disubstituted 1-Aryl-4Aminopiperidine Library Synthesis Using Computational Drug Design and High-Throughput Batch and Flow Technologies", ACS Combinatorial Science, 2013, pp. 503-511, vol. 15.
Butcher et al., "The Molecular Interactions That Stabilize RNA Tertiary Structure: RNA Motifs, Patterns, and Networks", Accounts of Chemical Research, 2011, pp. 1302-1311, vol. 44, No. 12.
Chen et al., "Synthesis from DNA of molecule with the connectivity of a cube", Letters to Nature, 1991, pp. 631-633, vol. 350.
Chen, "Expanding the Rule Set of DNA Circuitry with Associative Toehold Activation", Journal of the American Chemical Society, 2012, pp. 263-271, vol. 134.
Chin et al., "Correction of a splice-site mutation in the beta-globin gene stimulated by triplex-forming peptide nucleic acids", PNAS, 2008, pp. 13514-13519, vol. 105, No. 36.
Choi et al., "Programmable in situ amplification for multiplexed imaging of mRNA expression", Nature Biotechnology, 2010, pp. 1208-1214, vol. 28, No. 11.
Choi et al., "Next-Generation in Situ Hybridization Chain Reaction: Higher Gain, Lower Cost, Greater Durability", ACS Nano, 2014, pp. 4284-4294, vol. 8, No. 5.
Constantino et al., "tRNA-mRNA mimicry drives translation initiation from a viral IRES", Nature Structural and Molecular Biology, 2008, pp. 57-64, vol. 15, No. 1.
Dawson et al., "Synthesis of Proteins by Native Chemical Ligation", Science, New Series, 1994, pp. 776-779, vol. 266, No. 5186.
De Costa et al., "Evaluating the Effect of Ionic Strength on Duplex Stability for PNA Having Negatively or Positively Charged Side Chains", PLoS One, 2013, 8 pages, vol. 8, Issue 3.
De Francesco et al., "Challenges and successes in developing new therapies for hepatitis C", Nature, 2005, pp. 953-960, vol. 436.
Delebecque et al., "Organization of Intracellular Reactions with Rationally Designed RNA Aesthetics", Science, 2011, pp. 470-474, vol. 333.
Delia et al., "2,4,6-Trifluoropyrimidine. Reactions With Nitrogen Nucleophiles", Journal of Heterocyclic Chemistry, 2004, pp. 991-993, vol. 41.
Demidov et al., "Stability of peptide nucleic acids in human serum and cellular fluids", Biochemical Pharmacology, 1994, pp. 1310-1313, vol. 48, No. 6.
Dezhenkov et al., "Synthesis of anionic peptide nucleic acid oligomers including γ-carboxyethyl thymine monomers", Mendeleev Communications, 2015, pp. 47-48, vol. 25.
Dibrov et al., "Structure of a hepatitis C virus RNA domain in complex with a translation inhibitor reveals a binding mode reminiscent of riboswitches", PNAS, 2012, pp. 5223-5228, vol. 109, No. 4.
Dietz et al., "Folding DNA into Twisted and Curved Nanoscale Shapes", Science, 2009, pp. 725-730, vol. 325.
Dirks et al., "Triggered amplification by hybridization chain reaction", PNAS, 2004, pp. 15275-15278, vol. 101, No. 43.
Dose et al., "Convergent Synthesis of Peptide Nucleic Acids by Native Chemical Ligation", Organic Letters, 2005, pp. 4365-4368, vol. 7, No. 20.
Doudna, "Structural genomics of RNA", Nature Structural Biology Structural Genomics Supplement, 2000, pp. 954-956.
Douglas et al., "A Logic-Gated Nanorobot for Targeted Transport of Molecular Payloads", Science, 2012, pp. 831-834, vol. 335.
Dragulescu-Andrasi et al., "A Simple γ-Backbone Modification Preorganizes Peptide Nucleic Acid into a Helical Structure", Journal of the American Chemical Society, 2006, pp. 10258-10267, vol. 128.
Dueholm et al., "Synthesis of Peptide Nucleic Acid Monomers Containing the Four Natural Nucleobases: Thymine, Cytosine, Adenine, and Guanine and Their Oligomerization", Journal of Organic Chemistry, 1994, pp. 5767-5773, vol. 59.
Englund et al., "Synthesis of γ-Substituted Peptide Nucleic Acids: A New Place to Attach Fluorophores without Affecting DNA Binding", Organic Letters, 2005, pp. 3465-3467, vol. 7, No. 16.
Falkiewicz et al., "Synthesis of achiral and chiral peptide nucleic acid (PNA) monomers using Mitsunobu reaction", Tetrahedron, 2001, pp. 7909-7917, vol. 57.
Fischer, "Einfluss der Configuration auf die Wirkung der Enzyme", Berichte der Deutschen Chemischen Gesellschaft, 1894, pp. 2985-2993, vol. 27.
Frezza et al., "Modular Multi-Level Circuits from Immobilized DNA-Based Logic Gates", Journal of the American Chemical Society, 2007, pp. 14875-14879, vol. 129.
Fujimori et al., "Enantio-DNA Recognizes Complementary RNA but Not Complementary DNA", Journal of the American Chemical Society, 1990, pp. 7436-7438, vol. 112.
Genot et al., "Reversible Logic Circuits Made of DNA", Journal of the American Chemical Society, 2011, pp. 20080-20083, vol. 133.
Gerling et al., "Dynamic DNA devices and assemblies formed by shape-complementary, non-base pairing 3D components", Science, 2015, pp. 1446-1452, vol. 347, Issue 6229.
Hameed, "DNA Computation Based Approach for Enhanced Computing Power", International Journal of Emerging Sciences, 2011, pp. 31-37, vol. 1, No. 1.
Han et al., "DNA Origami with Complex Curvatures in Three-Dimensional Space", Science, 2011, pp. 342-346, vol. 332.

(56) References Cited

OTHER PUBLICATIONS

He et al., "Strand-Invasion of Extended, Mixed-Sequence B-DNA by γPNAS", Journal of the American Chemical Society, 2009, pp. 12088-12090, vol. 131, No. 34.
Hirao et al., "Natural versus Artificial Creation of Base Pairs in DNA: Origin of Nucleobases from the Perspectives of Unnatural Base Pair Studies", Accounts of Chemical Research, 2012, pp. 2055-2065, vol. 45, No. 12.
Huang et al., "Preparation and Determination of Optical Purity of γ-Lysine Modified Peptide Nucleic Acid Analogues", Archives of Pharmacal Research, 2012, pp. 517-522, vol. 35, No. 3.
Immordino et al., "Stealth liposomes: review of the basic science, rationale, and clinical approaches, existing and potential", International Journal of Nanomedicine, 2006, pp. 297-315, vol. 1, No. 3.
Janowski et al., "Inhibiting transcription of chromosomal DNA with antigene peptide nucleic acids", Nature Chemical Biology, 2005, pp. 210-215, vol. 1, No. 4.
Johnston et al., "An HIV Vaccine-Challenges and Prospects", New England Journal of Medicine, 2008, pp. 888-890, vol. 359, No. 9.
Jones et al., "Programmable materials and the nature of the DNA bond", Science, 2015, 11 pages, vol. 347, Issue No. 6224, Article No. 1260901.
Kadhane et al., "Strong coupling between adenine nucleobases in DNA single strands revealed by circular dichroism using synchrotron radiation", Physical Review E, 2008, 4 pages, vol. 77, Article No. 021901.
Ke et al., "Three-Dimensional Structures Self-Assembled from DNA Bricks", Science, 2012, pp. 1177-1183, vol. 338, No. 6111.
Kleiner et al., "DNA-Templated Polymerization of Side-Chain-Functionalized Peptide Nucleic Acid Aldehydes", Journal of the American Chemical Society, 2008, pp. 4646-4659, vol. 130.
Konrad et al., "Synthese und Eigenschaften von 2.4-Diamino-6- und -7-oxo-dihydropteridinen", Chemische Berichte, 1970, pp. 735-744, vol. 103, Issue 3, (English language Abstract).
Koppelhus et al., "Cell-Dependent Differential Cellular Uptake of PNA, Peptides, and PNA-Peptide Conjugates", Antisense & Nucleic Acid Drug Development, 2002, pp. 51-63, vol. 12.
Kosynkina et al., "A Convenient Synthesis Of Chiral Peptide Nucleic Acid (PNA) Monomers", Tetrahedron Letters, 1994, pp. 5173-5176, vol. 35, No. 29.
Kuhn et al., "Hybridization of DNA and PNA Molecular Beacons to Single-Stranded and Double-Stranded DNA Targets", Journal of the American Chemical Society, 2002, pp. 1097-1103, vol. 124, No. 6.
Kumar et al., "Conformationally Constrained PNA Analogues: Structural Evolution toward DNA/RNA Binding Selectivity", Accounts of Chemical Research, 2005, pp. 404-412, vol. 38, No. 5.
Kuzyk et al., "DNA-based self-assembly of chiral plasmonic nanostructures with tailored optical response", Nature, 2012, pp. 311-314, vol. 483, No. 7389.
Li et al., "DNA-Templated Organic Synthesis: Nature's Strategy for Controlling Chemical Reactivity Applied to Synthetic Molecules", Angewandte Chemie International Edition, 2004, pp. 4848-4870, vol. 43, No. 37.
Li et al., "Controlled assembly of dendrimer-like DNA", Nature Materials, 2004, pp. 38-42, vol. 3.
Liedl et al., "DNA-based nanodevices", Nanotoday, 2007, pp. 36-41, vol. 2, No. 2.
Lin et al., "Whole-Genome Shotgun Optical Mapping of Deinococcus radiodurans", Science, 1999, pp. 1558-1562, vol. 285, No. 5433.
Lund et al., "Molecular robots guided by prescriptive landscapes", Nature, 2010, pp. 206-210, vol. 465, No. 7295.
Manna et al., "Synthesis of optically pure γPNA monomers: a comparative study", Tetrahedron, 2015, pp. 3507-3514, vol. 71.
Michaelis et al., "Amplification by nucleic acid-templated reactions", Organic & Biomolecular Chemistry, 2014, pp. 2821-2833, vol. 12.
Mir, "Sequencing Genomes: From Individuals to Populations", Briefings in Functional Genomics and Proteomics, 2009, pp. 367-378, vol. 8, No. 5.

Mitra et al., "Aminomethylene Peptide Nucleic Acid (am-PNA): Synthesis, Regio-/Stereospecific DNA Binding, And Differential Cell Uptake of (α/γ,R/S)am-PNA Analogues", The Journal of Organic Chemistry, 2012, pp. 5696-5704, vol. 77.
Moradpour et al., "Replication of hepatitis C virus", Microbiology, 2007, pp. 453-463, vol. 5.
Morens et al., "The challenge of emerging and re-emerging infectious diseases", Nature, 2004, pp. 242-249, vol. 430, No. 6996.
Nielsen et al., "Sequence-Selective Recognition of DNA by Strand Displacement with a Thymine-Substituted Polyamide", Science, 1991, pp. 1497-1500, vol. 254, No. 5037.
Nielsen, "Peptide Nucleic Acid. A Molecule with Two Identities", Accounts of Chemical Research, 1999, pp. 624-630, vol. 32, No. 7.
Nielsen, "Addressing the challenges of cellular delivery and bioavailability of peptide nucleic acids (PNA)", Quarterly Reviews of Biophysics, 2005, pp. 345-350, vol. 38, No. 4.
Nissen et al., "RNA tertiary interactions in the large ribosomal subunit: The A-minor motif", PNAS, 2001, pp. 4899-4903, vol. 98, No. 9.
Niu et al., "AApeptides as a new class of antimicrobial agents", Organic & Biomolecular Chemistry, 2013, pp. 4283-4290, vol. 11.
Noller, "RNA Structure: Reading the Ribosome", Science, 2005, pp. 1508-1514, vol. 309, No. 5740.
Oh et al., "Excimer-Based Peptide Beacons: A Convenient Experimental Approach for Monitoring Polypeptide-Protein and Polypeptide-Oligonucleotide Interactions", Journal of the American Chemical Society, 2006, pp. 14018-14019, vol. 128.
Omabegho et al., "A Bipedal DNA Brownian Motor with Coordinated Legs", Science, 2009, pp. 67-71, vol. 324, No. 5923.
Pfingsten et al., "Structural Basis for Ribosome Recruitment and Manipulation by a Viral IRES RNA", Science, 2006, pp. 1450-1454, vol. 314, No. 5804.
Piccirilli et al., "Enzymatic incorporation of a new base pair into DNA and RNA extends the genetic alphabet", Nature, 1990, pp. 33-37, vol. 343, No. 6253.
Pinheiro et al., "Challenges and opportunities for structural DNA nanotechnology", Nature Nanotechnology, 2011, pp. 763-772, vol. 6, No. 12.
Poehlsgaard et al., "The Bacterial Ribosome as a Target for Antibiotics", Nature Reviews Microbiology, 2005, pp. 870-881, vol. 3, No. 11.
Qian et al., "Scaling Up Digital Circuit Computation with DNA Strand Displacement Cascades", Science, 2011, pp. 1196-1201, vol. 332, No. 6034.
Rajwanshi et al., "LNA stereoisomers: xylo-LNA (β-D-xylo configured locked nucleic acid) and α-L-LNA (α-L-ribo configured locked nucleic acid)", Chemical Communications, 1999, pp. 1395-1396, Issue 15.
Ranasinghe et al., "Linear fluorescent oligonucleotide probes with an acridine quencher generate a signal upon hybridisation", Chemical Communications, 2001, pp. 1480-1481, Issue 16.
Rapireddy et al., "Strand Invasion of Mixed-Sequence B-DNA by Acridine-Linked, γ-Peptide Nucleic Acid (γ-PNA)", Journal of the American Chemical Society, 2007, pp. 15596-15600, vol. 129.
Rapireddy et al., "Strand Invasion of Mixed-Sequence, Double-Helical B-DNA by γ-Peptide Nucleic Acids Containing G-Clamp Nucleobases under Physiological Conditions", Biochemistry, 2011, pp. 3913-3918, vol. 50.
Ratilainen et al., "Hybridization of Peptide Nucleic Acid", Biochemistry, 1998, pp. 12331-12342, vol. 37.
Ratilainen et al., "Thermodynamics of Sequence-Specific Binding of PNA to DNA", Biochemistry, 2000, pp. 7781-7791, vol. 39.
Rothemund, "Folding DNA to create nanoscale shapes and patterns", Nature, 2006, pp. 297-302, vol. 440, No. 7082.
Sahoo et al., "Pyrene Excimer Fluorescence: A Spatially Sensitive Probe To Monitor Lipid-Induced Helical Rearrangement of Apolipophorin III", Biochemistry, 2000, pp. 6594-6601, vol. 39.
Sahu et al., "Synthesis of Conformationally Preorganized and Cell-Permeable Guanidine-Based γ-Peptide Nucleic Acids (γGPNAs)", Journal of Organic Chemistry, 2009, pp. 1509-1516, vol. 74, No. 4.

(56) References Cited

OTHER PUBLICATIONS

Sahu et al., "Synthesis and Characterization of Conformationally-Preorganized, MiniPEG-Containing γPNAs with Superior Hybridization Properties and Water Solubility", Journal of Organic Chemistry, 2011, pp. 5614-5627, vol. 76, No. 14.

Saladino et al., "Meteorites as Catalysts for Prebiotic Chemistry", Chemistry A European Journal, 2013, pp. 16916-16922, vol. 19.

Seelig et al., "Enzyme-Free Nucleic Acid Logic Circuits", Science, 2006, pp. 1585-1588, vol. 314, No. 5805.

Seitz, "Solid-Phase Synthesis of Doubly Labeled Peptide Nucleic Acids as Probes for the Real-Time Detection of Hybridization", Angewandte Chemie International Edition, 2000, pp. 3249-3252, vol. 39, No. 18.

Serpell et al., "Precision Polymers and 3D DNA Nanostructures: Emergent Assemblies from New Parameter Space", Journal of the American Chemical Society, 2014, pp. 15767-15774, vol. 136.

Severcan et al., "A polyhedron made of tRNAs", Nature Chemistry, 2010, pp. 772-779, vol. 2, No. 9.

Sforza et al., "Chiral Peptide Nucleic Acids (PNAs): Helix Handedness and DNA Recognition", European Journal of Organic Chemistry, 1999, pp. 197-204.

Silverman et al., "Detecting RNA and DNA with Templated Chemical Reactions", Chemical Reviews, 2006, pp. 3775-3789, vol. 106, No. 9.

Singer et al., "Electronic Barcoding of a Viral Gene at the Single-Molecule Level", Nano Letters, 2012, pp. 1722-1728, vol. 12, No. 3.

Smalley et al., "Fluorescence of covalently attached pyrene as a general RNA folding probe", Nucleic Acids Research, 2006, pp. 152-166, vol. 34, No. 1.

Srinivasan et al., "Pyridopyrimidines. 11. Synthesis of 5-Deaza-5-oxoaminopterin and Related Compounds", Journal of Organic Chemistry, 1980, pp. 3746-3748, vol. 45, No. 19.

Stanzl et al., "Fifteen Years of Cell-Penetrating, Guanidinium-Rich Molecular Transporters: Basic Science, Research Tools, and Clinical Applications", Accounts of Chemical Research, 2013, pp. 2944-2954, vol. 46, No. 12.

Stratagene, "Gene Characterization Kits", 1988 Catalog, 1988, p. 39.

Sugiyama et al., "Chiral Peptide Nucleic Acids with a Substituent in the N-(2-Aminoethyl)glycine Backbone", Molecules, 2013, pp. 287-310, vol. 18.

Svirskaya et al., "Fluorinated Heterocyclic Compounds. 2. 2,4-Difluoro and 4-Amino-2-fluoropyrimidines, Nucleoside Base Analogs", Journal of Heterocyclic Chemistry, 1985, pp. 149-153, vol. 22.

Tackett et al., "Non-Watson-Crick interations between PNA and DNA inhibit the ATPase activity of bacteriophage T4 Dda helicase", Nucleic Acids Research, 2002, pp. 950-957, vol. 30, No. 4.

Tedeschi et al., "Synthesis of new chiral PNAs bearing a dipeptide-mimic monomer with two lysine-derived stereogenic centres", Tetrahedron Letters, 2005, pp. 8395-8399, vol. 46.

Teixidó et al., "Selective Hydrolysis of 2,4-Diaminopyrimidine Systems: A Theoretical and Experimental Insight into an Old Rule", Journal of Organic Chemistry, 2001, pp. 192-199, vol. 66.

Theimer et al., "Structure of the Human Telomerase RNA Pseudoknot Reveals Conserved Tertiary Interactions Essential for Function", Molecular Cell, 2005, pp. 671-682, vol. 17, No. 5.

Thurner et al., "Conserved RNA secondary structures in Flaviviridae genomes", Journal of General Virology, 2004, pp. 1113-1124, vol. 85, Part 5.

Tomac et al., "Ionic Effects on the Stability and Conformation of Peptide Nucleic Acid Complexes", Journal of the American Chemical Society, 1996, pp. 5544-5552, vol. 118, No. 24.

Wan et al., "Understanding the transcriptome through RNA structure", Nature Reviews Genomics, 2011, pp. 641-655, vol. 12, No. 9.

Watts et al., "Architecture and secondary structure of an entire HIV-1 RNA genome", Nature, 2009, pp. 711-716, vol. 460, No. 7256.

Wei et al., "Complex shapes self-assembled from single-stranded DNA tiles", Nature, 2012, pp. 623-626, vol. 485, No. 7400.

Wengel, "Synthesis of 3'-C- and 4'-C-Branched Oligodeoxynucleotides and the Development of Locked Nucleic Acid (LNA)", Accounts of Chemical Research, 1999, pp. 301-310, vol. 32, No. 4.

Wimberly et al., "Structure of the 30S ribosomal subunit", Nature, 2000, pp. 327-339, vol. 407, No. 6802.

Winssinger, "Nucleic Acid-programmed Assemblies: Translating Instruction into Function in Chemical Biology", Chimia, 2013, pp. 340-348, vol. 67, No. 5.

Wittung et al., "DNA-like double helix formed by peptide nucleic acid", Letters to Nature, 1994, pp. 561-563, vol. 368, No. 6471.

Wittung et al., "Induced Chirality in PNA-PNA Duplexes", Journal of the American Chemical Society, 1995, pp. 10167-10173, vol. 117, No. 41.

Wu et al., "Synthesis of chiral peptide nucleic acids using Fmoc chemistry", Tetrahedron, 2001, pp. 8107-8113, vol. 57, No. 38.

Yang et al., "Light-switching excimer probes for rapid protein monitoring in complex biological fluids", PNAS, 2005, pp. 17278-17283, vol. 102, No. 48.

Yan et al., "DNA-Templated Self-Assembly of Protein Arrays and Highly Conductive Nanowires", Science, 2003, pp. 1882-1884, vol. 301, No. 5641.

Yeh et al., "Crystal Structure of Chiral γ PNA with Complementary DNA Strand—Insights into the Stability and Specificity of Recognition and Conformational Preorganization", Journal of the American Chemical Society, 2010, pp. 10717-10727, vol. 132, No. 31.

Yurke et al., "A DNA-fuelled molecular machine made of DNA", Nature, 2000, pp. 605-608, vol. 406, No. 6796.

Zhang et al., "Dynamic DNA nanotechnology using strand-displacement reactions", Nature Chemistry, 2011, pp. 103-113, vol. 3, No. 2.

Zhou et al., "Novel Binding and Efficient Cellular Uptake of Guanidine-Based Peptide Nucleic Acids (GPNA)", Journal of the American Chemical Society, 2003, pp. 6878-6879, vol. 125, No. 23.

Arambula et al., "A simple ligand that selectively targets CUG trinucleotide repeats and inhibits MBNL protein binding", PNAS, 2009, pp. 16068-16073, vol. 106, No. 38.

Artigas et al., "Synthesis of Janus Compounds for the Recognition of G-U Mismatched Nucleobase Pairs", The Journal of Organic Chemistry, 2013, pp. 10666-10677, vol. 78.

Branda et al., "Janus Wedges: a new approach towards nucleobase-pair recognition", Chemical Communications, 1996, pp. 2443-2444, Issue 21.

Chen et al., "Formation and Stability of a Janus-Wedge Type of DNA Triplex", Journal of the American Chemical Society, 2004, pp. 70-71, vol. 126.

Chen et al., "A Janus-Wedge DNA Triplex with A-W1-T and G-W2-C Base Triplets", Journal of the American Chemical Society, 2008, pp. 13190-13191, vol. 130.

Robinson et al., "Modular Riboswitch Toolsets for Synthetic Genetic Control in Diverse Bacterial Species", Journal of the American Chemical Society, 2014, pp. 10615-10624, vol. 136.

Shin et al., "Bifacial Nucleoside as a Surrogate for Both T and A in Duplex DNA", Journal of the American Chemical Society, 2011, pp. 6926-6929, vol. 133.

Zeng et al., "Discrete Assembly of Synthetic Peptide-DNA Triplex Structures from Polyvalent Melamine-Thymine Bifacial Recognition", Journal of the American Chemical Society, 2012, pp. 832-835, vol. 134.

Zhao et al., "Synthesis of a Complete Janus-type Guanosine-Cytosine Base and Its 2'-Deoxyribonucleoside", Chemistry Letters, 2011, pp. 684-686, vol. 40.

Alsbaiee et al., "Synthesis of rhenium chelated MAG3 functionalized rosette nanotubes", Tetrahedron Letters, 2012, pp. 1645-1651, vol. 53.

Deng et al., "Covalent Capture of Self-Assembled Rosette Nanotubes", Macromolecules, 2012, pp. 7157-7162, vol. 45.

Fenniri et al., "Helical Rosette Nanotubes: Design, Self-Assembly and Characterization", J. Am. Chem. Soc. 2001, pp. 3854-3855, vol. 123.

Jonhson et al., "Nanotubes and Related Nanostructures", Materials Research Society Symposium Proceedings, 2007, vol. 1057.

(56) References Cited

OTHER PUBLICATIONS

Tikhomirov et al., "Synthesis of Hydrophobic Derivatives of the G[and]C Base for Rosette Nanotube Self-Assembly in Apolar Media", J. Org. Chem., 2008, pp. 4248-4251, vol. 73.
Yang et al., "Synthesis of Janus type nucleoside analogues and their preliminary bioactivity", Organic & Biomolecular Chemistry, 2010, pp. 1516-1522, vol. 9.
Zhang et al., "Arginine-glyzine-aspartic acid modified rosette nanotube-hydrogel composites for bone tissue engineering", Biomaterials, 2009, pp. 1309-1320, vol. 30.
Zhang et al., "Tuning cell adhesion on titanium with osteogenic rosette nanotubes", J. Biomed. Mater. Res., 2010, pp. 550-563, vol. 95A:2.
Cheng et al., "Canonical and Non-Canonical Barriers Facing AntimiR Cancer Therapeutics", Curr Med Chem., 2013, vol. 20, No. 29, pp. 3582-3593.
Gupta et al., "Anti-tumor Activity of miniPEG-γ-Modified PNAs to Inhibit MicroRNA-210 for Cancer Therapy", Molecular Therapy: Nucleic Acids, 2017, vol. 9, pp. 111-119.
McNeer et al., "Nanoparticles Deliver Triplex-forming PNAs for Site-specific Genomic Recombination in CD34+ Human Hematopoietic Progenitors", 2011, Molecular Therapy, vol. 19, No. 1, pp. 172-180.
McNeer et al., "Nanoparticles that deliver triplex-forming peptide nucleic acid molecules correct F508del CFTR in airway epithelium", Nature Communications, 2015, 6:6952, 11 pages.
Schleifman et al., "Site-specific Genome Editing in PBMCs With PLGA Nanoparticle-delivered PNAs Confers HIV-1 Resistance in Humanized Mice", Molecular Therapy—Nucleic Acids, 2013, vol. 2, No. 11, 10 pages.
Ausin et al., "Synthesis of Amino- and Guanidino-G-Clamp PNA Monomers", Organic Letters, 2002, pp. 4073-4075, vol. 4:23.
Babar et al., "Nanoparticle-based therapy in an in vivo microRNA-155 (miR-155)-dependent mouse model of lymphoma", PNAS, 2012, pp. E1695-E1704.
Debaene et al., "Synthesis of a PNA-encoded cysteine protease inhibitor library", Tetrahedron, 2004, pp. 8677-8690, vol. 60.
Douglas et al., "Self-assembly of DNA into nanoscale three-dimensional shapes", Nature, 2009, pp. 414-418, vol. 459 (7245).
Dragulescu-Andrasi et al., "Cell-permeable GPNA with appropriate backbone stereochemistry and spacing binds sequence-specifically to RNA", Chem. Commun., 2005, pp. 244-246.
Dragulescu-Andrasi et al., "Cell-Permeable Peptide Nucleic Acid Designed to Bind to the 5'-Untranslated Region of E-cadherin Transcript Induces Potent and Sequence-Specific Antisense Effects", J. Am. Chem. Soc., 2006, pp. 16104-16112, vol. 128.
Englund et al., "γ-Substituted Peptide Nucleic Acids Constructed from L-Lysine are a Versatile Scaffold for Multifunctional Display", Angew. Chem. Int. Ed., 2007, pp. 1414-1418, vol. 46.
Felix et al., "Covalent Linkage of Melamine and Cyanurate Improves the Thermodynamic Stability of Hydrogen-Bonded Double Rosettes in Polar Solvents", Eur. J. Org. Chem., 2003, pp. 1463-1474.
Gangamani et al., "Synthesis of N alpha-(Purinyl/Pyrimidinyl acetyl)-4-Aminoproline Diastereomers with Potential Use in PNA Synthesis", Tetrahedron, 1996, pp. 15017-15030, vol. 52:47.
Gangamani et al., "Chiral analogues of Peptide Nucleic Acids: Synthesis of 4-aminoprolyl nucleic acids and DNA complementation studies using UV/CD spectroscopy", Tetrahedron, 1999, pp. 177-192, vol. 55.
Gartner et al., "DNA-Templated Organic Synthesis and Selection of a Library of Macrocycles", Science, 2004, 9 pages, vol. 305 (5690).
Gellman, "Foldamers: A Manifesto", Acc. Chem. Res., 1998, pp. 173-180, vol. 31.
Gokhale et al., "Amino / guanidino-functionalized N-(pyrrolidin-2-ethyl)glycine-based pet-PNA: Design, synthesis and binding with DNA/RNA", Org. Biomol. Chem., 2010, pp. 3742-3750, vol. 8.
Govindaraju et al., "(1S,2R/1R,2S)-cis-Cyclopentyl PNAs (cpPNAs) as Constrained PNA Analogues: Synthesis and Evaluation of aeg-cpPNA Chimera and Stereopreferences in Hybridization with DNA/RNA", J. Org. Chem., 2004, pp. 5725-5734, vol. 69.

Griffith et al., "Tissue Engineering—Current Challenges and Expanding Opportunities", Science, 2002, pp. 1009-1014, vol. 295.
Gu et al., "A Proximity-Based Programmable DNA Nanoscale Assembly Line", Nature, 2010, pp. 202-205, vol. 465 (7295).
Harris et al., "Activity Profile of Dust Mite Allergen Extract Using Substrate Libraries and Functional Proteomic Microarrays", Chemistry & Biology, 2004, pp. 1361-1372, vol. 11.
Hill et al., "A Field Guide to Foldamers", Chem. Rev., 2001, pp. 3893-4011, vol. 101.
Hirao et al., "A Synthetic Biology Approach to the Expansion of the Genetic Alphabet: Molecular Design of Unnatural Base Pairs of DNA", TCIMAIL, 2012, pp. 1-10.
Hirao et al., "Unnatural base pair systems toward the expansion of the genetic alphabet in the central dogma", Proc. Jpn. Acad., Ser. B, 2012, pp. 345-367, vol. 88:7.
Jordan et al., "Synthesis of New Building Blocks for Peptide Nucleic Acids Containing Monomers With Variations in the Backbone", Bioorganic & Medicinal Chemistry Letters, 1997, pp. 681-686, vol. 7:6.
Jordan et al., "New Hetero-Oligomeric Peptide Nucleic Acids With Improved Binding Properties to Complementary DNA", Bioorganic & Medicinal Chemistry Letters, 1997, pp. 687-690, vol. 7:6.
Kanan et al., "Reaction discovery enabled by DNA-templated synthesis and in vitro selection", Nature, 2004, pp. 545-549, vol. 431.
Kwon et al., "Materials science of DNA", J. Mater. Chem, 2009, pp. 1353-1380, vol. 19.
Lusvarghi et al., "Loop and Backbone Modifications of Peptide Nucleic Acid Improve G-Quadruplex Binding Selectivity", J. Am. Chem. Soc., 2009, pp. 18415-18424, vol. 131.
Malyshev et al., "Solution Structure, Mechanism of Replication, and Optimization of an Unnatural Base Pair", Chemistry, 2010, pp. 12650-12659, vol. 16 (42).
Manicardi et al., "Cellular Uptakes, Biostabilities and Anti-miR-210 Activities of Chiral Arginine-PNAs in Leukaemic K562 Cells", ChemBioChem, 2012, pp. 1327-1337, vol. 13.
Marras, "Selection of Fluorophore and Quencher Pairs for Fluorescent Nucleic Acid Hybridization Probes", Methods in Molecular Biology, 2006, pp. 3-16.
McNeer et al., "Polymer Delivery Systems for Site-Specific Genome Editing", J Control Release, 2011, pp. 312-316, vol. 155 (2).
Nielsen, "Peptide Nucleic Acid. A Molecule with Two Identities", Acc. Chem. Res., 1999, pp. 624-630, vol. 32.
Pensato et al., "γ-Hydroxymethyl PNAs: Synthesis, interaction with DNA and inhibition of protein/DNA interactions", Bioorganic Chemistry, 2010, pp. 196-201, vol. 38.
Pianowski et al., "Imaging of mRNA in Live Cells Using Nucleic Acid-Templated Reduction of Azidorhodamine Probes", J. Am. Chem. Soc., 2009, pp. 6492-6497, vol. 131.
Picuri et al., "Universal Translators for Nucleic Acid Diagnosis", J. Am. Chem. Soc., 2009, pp. 9368-9377, vol. 131.
Poth et al., "Discovery of Cyclotides in the Fabaceae Plant Family Provides New Insights into the Cyclization, Evolution, and Distribution of Circular Proteins", ACS Chem. Biol., 2011, pp. 345-355, vol. 6.
Rapireddy et al., "RTD-1 Mimic Containing γPNA Scaffold Exhibits Broad-Spectrum Antibacterial Activities", J. Am. Chem. Soc., 2012, pp. 4041-4044, vol. 134.
Reif, "Scaling Up DNA Computation", Science, 2011, pp. 1156-1157, vol. 332.
Rozners, "Recent Advances in Chemical Modification of Peptide Nucleic Acids", Journal of Nucleic Acids, 2012, pp. 1-8.
Sforza et al., "A Peptide Nucleic Acid Embedding a Pseudopeptide Nuclear Localization Sequence in the Backbone Behaves as a Peptide Mimic", Eur J. Org. Chem., 2010, pp. 2441-2444.
Shiryaeva et al., "Solid-phase synthesis of negatively charged oligomeric polyamide mimetics of nucleic acids", Fine Chemical Technologies, 2011, pp. 81-85, vol. 6:2 (English-language Abstract).
Sivakumar et al., "A Fluorogenic 1,3-Dipolar Cycloaddition Reaction of 3-Azidocoumarins and Acetylenes", Organic Letters, 2004, pp. 4603-4606, vol. 6:24.
Tallia et al., "Sepsis: Improving the odds", Perspectives, Spring 2009, pp. 6-11.

(56) References Cited

OTHER PUBLICATIONS

Tauraite et al., "Modified Nucleotides as Substrates of Terminal Deoxynucleotidyl Transferase", Molecules, 2017, pp. 1-16, vol. 22.
Van Steensel et al., "Genomics tools for the unraveling of chromosome architecture", Nat Biotechnol, 2010, pp. 1089-1095, vol. 28 (10).
Whyte et al., "Master Transcription Factors and Mediator Establish Super-Enhancers at Key Cell Identity Genes", Cell, 2013, pp. 307-319, vol. 153 (2).
Wierzbinski et al., "Effect of Backbone Flexibility on Charge Transfer Rates in Peptide Nucleic Acid Duplexes", J. Am. Chem. Soc., 2012, pp. 9335-9342, vol. 134.
Winssinger et al., "From Split-Pool Libraries to Spatially Addressable Microarrays and Its Application to Functional Proteomic Profiling", Angew. Chem. Int. Ed., 2001, pp. 3152-3155, vol. 40:17.
Winssinger et al., "PNA-Encoded Protease Substrate Microarrays", Chemistry & Biology, 2004, pp. 1351-1360, vol. 11.
Zhang et al., "Engineering Entropy-Driven Reactions and Networks Catalyzed by DNA", Science, 2007, pp. 1121-1125, vol. 318.

\* cited by examiner

DIVALENT NUCLEOBASE COMPOUNDS AND USES THEREFOR

CROSS REFERENCE TO RELATED APPLICATIONS

This application is the United States national phase of International Application No. PCT/US2017/053395 filed Sep. 26, 2017, and claims the benefit of U.S. Provisional Patent Application No. 62/495,843 filed Sep. 26, 2016, each of which is incorporated herein by reference in its entirety.

STATEMENT REGARDING FEDERAL FUNDING

This invention was made with government support under the National Science Foundation CHE-1012467. The government has certain rights in this invention.

BACKGROUND

Described herein are nucleobases, polymer monomers comprising the nucleobases and nucleic acids and analogs thereof comprising the nucleobases. Also described herein are methods of use of the nucleobases, polymer monomers comprising the nucleobases and nucleic acids and analogs thereof comprising the nucleobases.

For most organisms, genetic information is encoded in double-stranded DNA in the form of Watson-Crick base-pairing—in which adenine (A) pairs with thymine (T) and cytosine (C) with guanine (G). Depending on which set of this genetic information is decoded through transcription and translation, the developmental program and physiological status will be determined. Development of molecules that can be tailor-designed to bind sequence-specifically to any part of this genetic biopolymer (DNA or RNA), thereby enabling the control of the flow of genetic information and assessment and manipulation of the genome's structures and functions, is important for biological and biomedical research in the effort to unravel the molecular basis of life, including molecular tools for basic research in biology. This effort is also important for medicinal and therapeutic applications for the treatment and detection of genetic diseases.

Compared to proteins, RNA molecules are easier to target because they are made up of just four building blocks (A, C, G, U), whose interactions are defined by the well-established rules of Watson-Crick base-pairing. Compared to standard, double-stranded DNA (or RNA), the secondary structures of RNA are generally thermodynamically less stable and, thus, energetically less demanding for binding because, in addition to being canonical (perfectly-matched) base-pairs, many of them are noncanonical (mismatched) and contain single-stranded loops, bulges, and junctions. The presence of these local interacting domains is essential for 'tertiary' interactions and assembly of the secondary structures into compact three-dimensional shapes. As such, slight variations in the interaction patterns or bonding strengths within these regions will have a profound effect on the overall three-dimensional folding patterns of RNA. Thus, molecules that can be used to modulate RNA interactions and thereby interfere with the RNA folding behaviors are important as molecular tools for assessing RNA functions, as well as therapeutic and diagnostic reagents.

RNA-RNA and RNA-protein interactions play key roles in gene regulation, including replication, translation, folding and packaging. The ability to selectively bind to regions within the secondary structures of RNA will often modify their physiological functions.

SUMMARY

Provided herein are reagents that can be used to target double-stranded nucleic acid sequences and bring together mismatched sequences. The reagents are relatively small in size, can be manufactured in large quantity and more cheaply using solution-phase methodology, and are readily taken-up by cells. They are especially appealing for targeting rapidly evolving sites, such as those associated with the pathology of cancer, bacterial and viral infection, because the described recognition scheme is modular in nature and can be readily modified to match a newly emerged sequence at will. As such, divalent nucleobases are described herein. Divalent nucleobases are capable of forming directional hydrogen bonding interactions with two strands of DNA and/or RNA, whether or not mismatches are present. This platform has applications in basic research in biology and biotechnology, diagnostics, and therapeutics. The described molecular recognition platform is expected to lead to the development of molecular tools for manipulation of nucleic acid structures and functions, as well as in the development of molecular therapies for treating genetic diseases and infectious diseases.

According to one aspect of the invention, a genetic recognition reagent is provided. The genetic recognition reagent comprises a plurality of nucleobase moieties attached to a nucleic acid or nucleic acid analog backbone, in which at least one nucleobase moiety is chosen from:

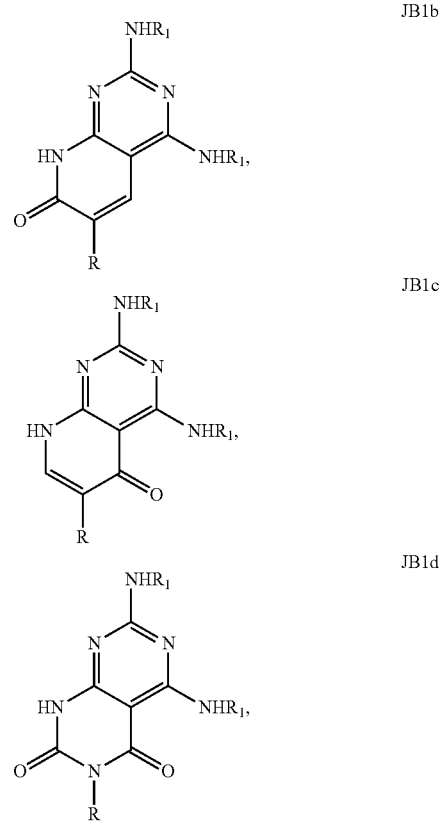

JB2b 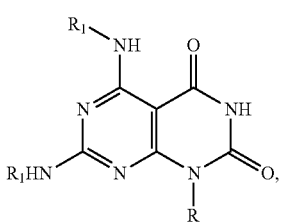
JB3b 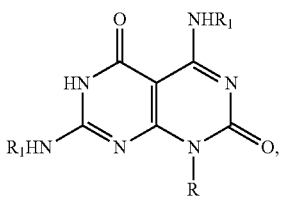
JB4b 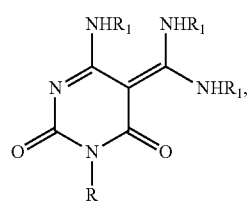
JB4c 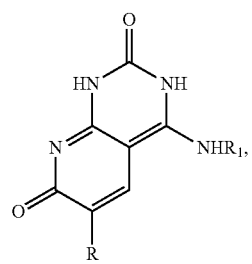
JB4d 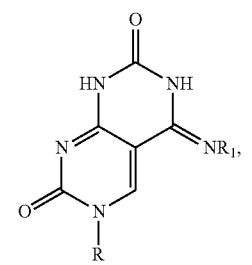
JB4e 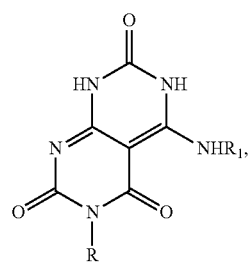
JB5b 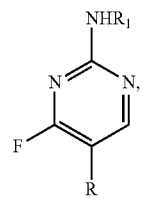
JB5c 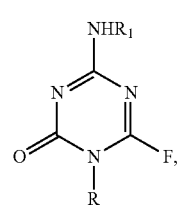
JB5d 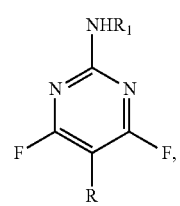
JB6b 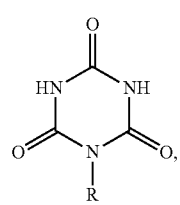
JB7e 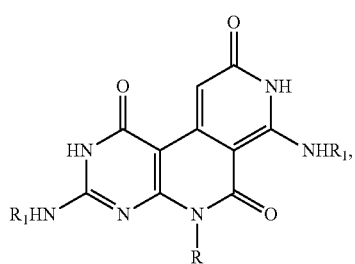
JB7f 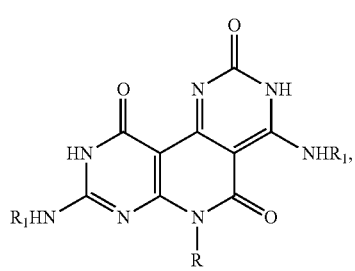
JB8b 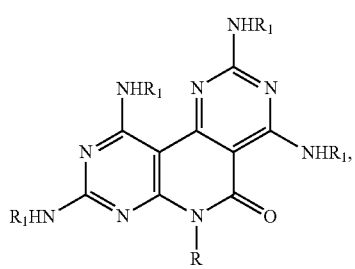
JB9c 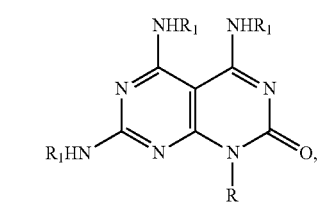

-continued

JB10b, JB10c, JB11b, JB11c, JB11d, JB11e, JB12b, JB13b, JB13c, JB13d, JB13e, JB13f, JB13g, JB13h (Chemical structures of heterocyclic compounds with R and NHR₁ substituents)

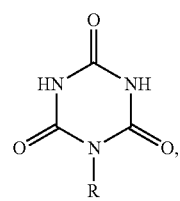
JB13i wherein R1 is H or a protecting group, and R is a residue of a nucleic acid or nucleic acid analog backbone monomer in the genetic recognition reagent. According to one aspect, an array comprising the genetic recognition reagent is provided.

According to another aspect of the invention, a compound is provided having a structure:

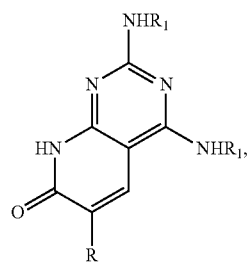
JB1b

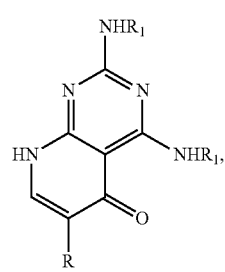
JB1c

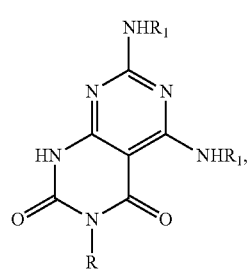
JB1d

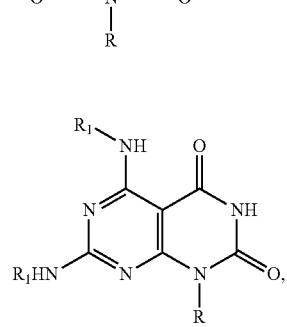
JB2b

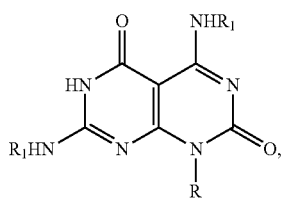
JB3b

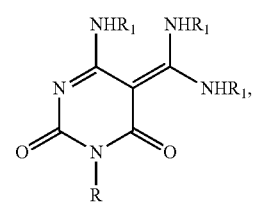
JB4b

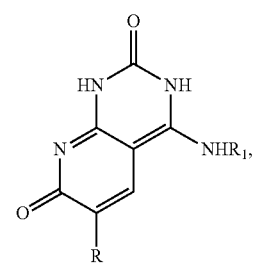
JB4c

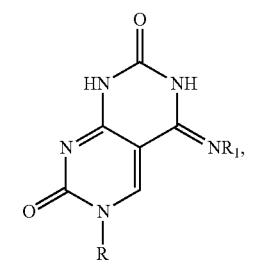
JB4d

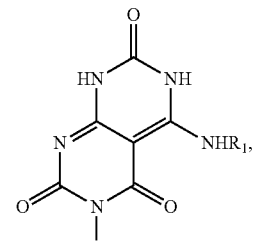
JB4e

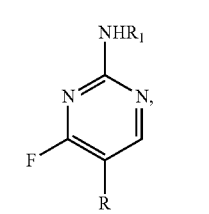
JB5b

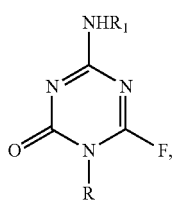
JB5c

-continued
JB5d
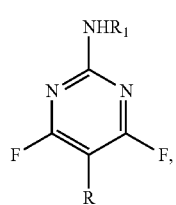
JB6b
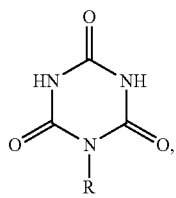
JB7e
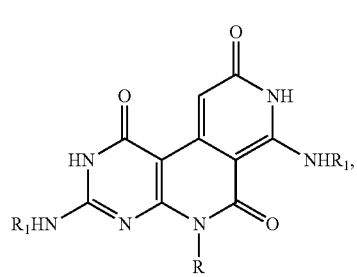
JB7f
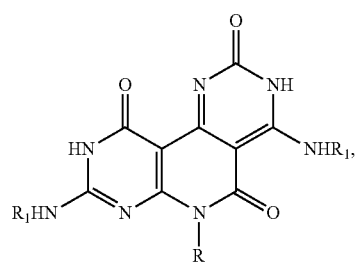
JB8b
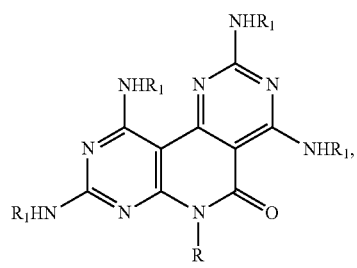
JB9c
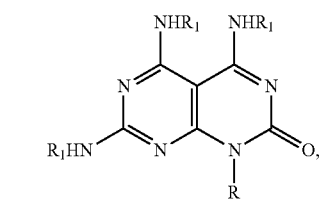
-continued
JB10b
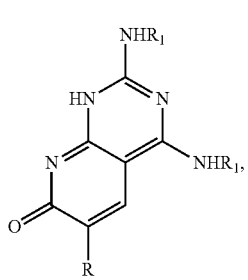
JB10c
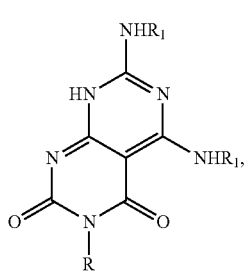
JB11b
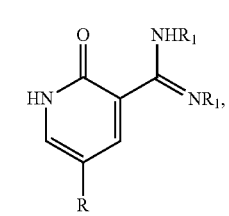
JB11c
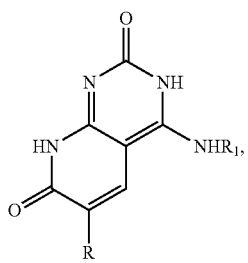
JB11d
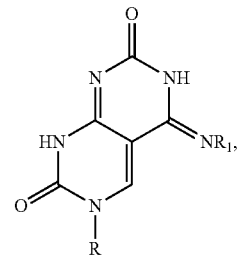
JB11e
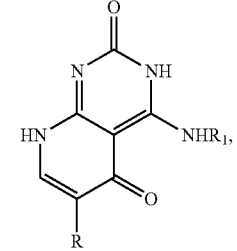

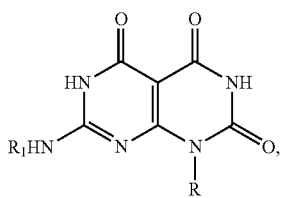
JB12b

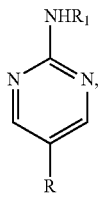
JB13b

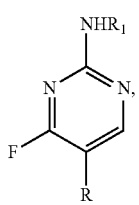
JB13c

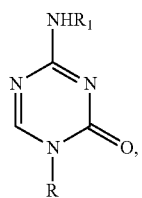
JB13d

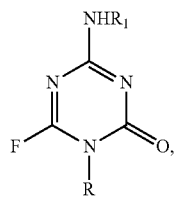
JB13e

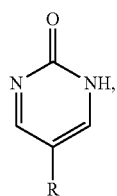
JB13f

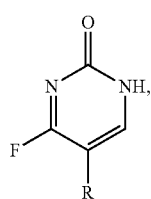
JB13g

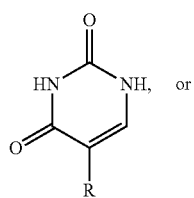
JB13h

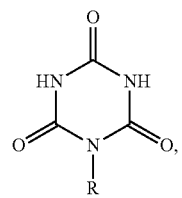
JB13i wherein R1 is H or a protecting group, and R is: H; a protecting group; a reactive group; a solid substrate; or a nucleic acid or nucleic acid analog backbone monomer or a residue thereof in a nucleic acid or nucleic acid analog polymer. A composition, such as a pharmaceutical composition, comprising the compound also is provided. According to yet another aspect, a kit is provided comprising the compound in a vessel, such as a cartridge. In one aspect, R is a nucleic acid or nucleic acid analog backbone monomer.

According to aspects, a method of detection of a target sequence in a nucleic acid also is provided. The method comprising contacting the genetic recognition reagent with a sample comprising nucleic acid, and detecting binding of the genetic recognition reagent with a nucleic acid.

According to another aspect, a method of isolation and purification or a nucleic acid containing a target sequence is provided, comprising, contacting a nucleic acid sample with the genetic recognition reagent, separating the nucleic acid sample from the genetic recognition reagent, leaving any nucleic acid bound to the genetic recognition reagent bound to the genetic recognition reagent, and separating the genetic recognition reagent from any nucleic acid bound to the genetic recognition reagent.

DETAILED DESCRIPTION

Figure 1A:
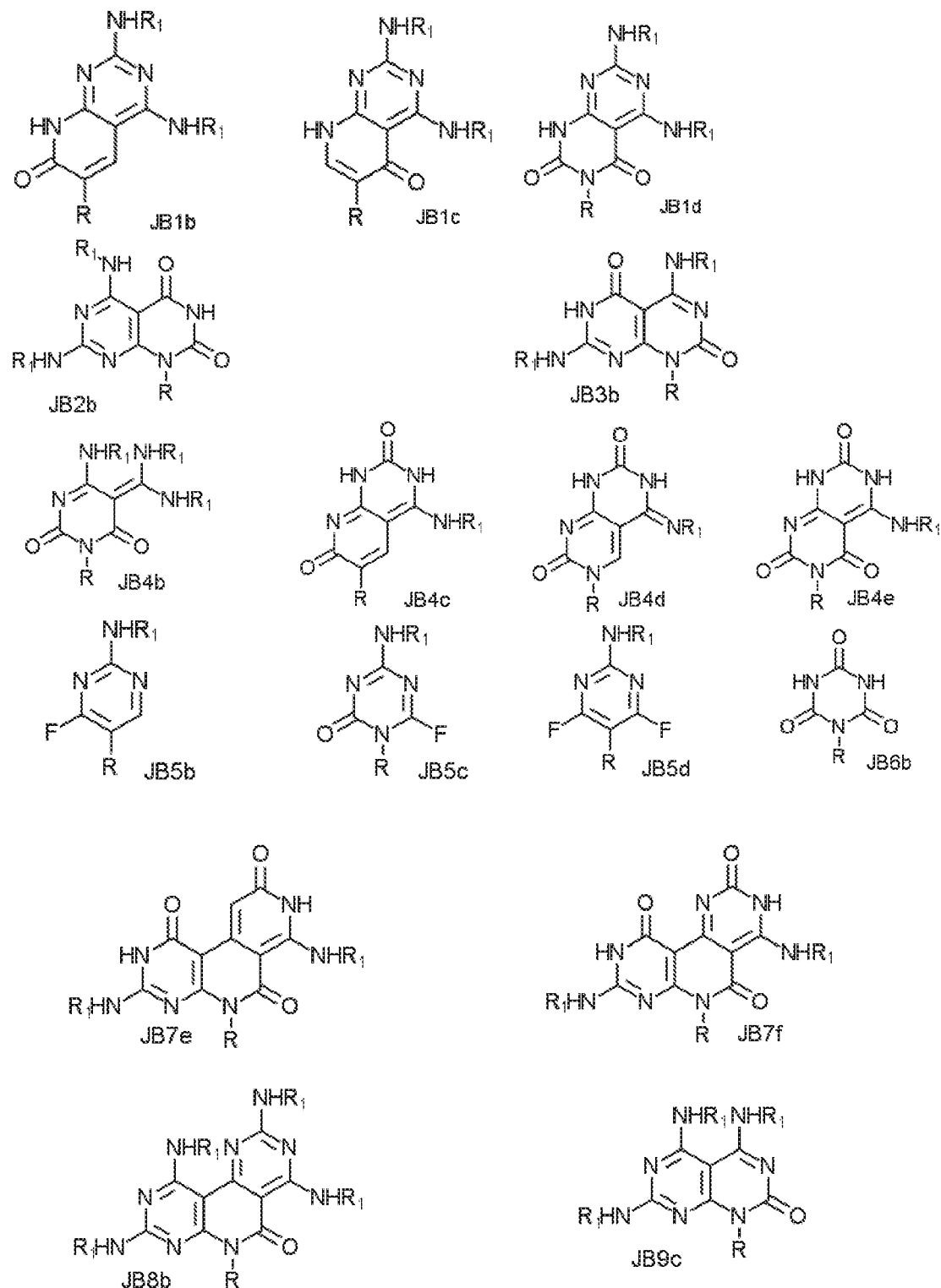
FIGS. 1A and 1B provide structures of the second-generation nucleobases disclosed herein.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of ranges is intended as a continuous range including every value between the minimum and maximum values. As used herein "a" and "an" refer to one or more.

As used herein, the term "comprising" is open-ended and may be synonymous with "including", "containing", or "characterized by". As used herein, embodiments "comprising" one or more stated elements or steps also include, but are not limited to embodiments "consisting essentially of" and "consisting of" these stated elements or steps.

The term "polymer composition" is a composition comprising one or more polymers. As a class, "polymers" includes, without limitation, homopolymers, heteropolymers, co-polymers, block polymers, block co-polymers and can be both natural and synthetic. Homopolymers contain one type of building block, or monomer, whereas co-polymers contain more than one type of monomer. An "oligomer" is a polymer that comprises a small number of monomers, such as, for example, from 3 to 100 monomer residues. As such, the term "polymer" includes oligomers. The terms "nucleic acid" and "nucleic acid analog" includes nucleic acid and nucleic acid polymers and oligomers.

A polymer "comprises" or is "derived from" a stated monomer if that monomer is incorporated into the polymer. Thus, the incorporated monomer that the polymer comprises is not the same as the monomer prior to incorporation into a polymer, in that at the very least, certain linking groups are incorporated into the polymer backbone or certain groups are removed in the polymerization process. A polymer is said to comprise a specific type of linkage if that linkage is present in the polymer. An incorporated monomer is a "residue". A typical monomer for a nucleic acid or nucleic acid analog is referred to as a nucleotide.

A "moiety" (pl. "moieties")) is a part of a chemical compound, and includes groups, such as functional groups. As such, as therapeutic agent moiety is a therapeutic agent or compound that is modified by attachment to another compound moiety, such as a polymer monomer, e.g. the nucleic acid or nucleic acid analog monomers described herein, or a polymer, such as a nucleic acid or nucleic acid analog as described herein.

"Alkyl" refers to straight, branched chain, or cyclic hydrocarbon groups including from 1 to about 20 carbon atoms, for example and without limitation $C_{1-3}$, $C_{1-6}$, $C_{1-10}$ groups, for example and without limitation, straight, branched chain alkyl groups such as methyl, ethyl, propyl, butyl, pentyl, hexyl, heptyl, octyl, nonyl, decyl, undecyl, dodecyl, and the like. "Substituted alkyl" refers to alkyl substituted at 1 or more, e.g., 1, 2, 3, 4, 5, or even 6 positions, which substituents are attached at any available atom to produce a stable compound, with substitution as described herein. "Optionally substituted alkyl" refers to alkyl or substituted alkyl. "Halogen," "halide," and "halo" refers to —F, —Cl, —Br, and/or —I. "Alkylene" and "substituted alkylene" refer to divalent alkyl and divalent substituted alkyl, respectively, including, without limitation, ethylene (—$CH_2$—$CH_2$—). "Optionally substituted alkylene" refers to alkylene or substituted alkylene.

"Alkene or alkenyl" refers to straight, branched chain, or cyclic hydrocarbyl groups including from 2 to about 20 carbon atoms, such as, without limitation $C_{1-3}$, $C_{1-6}$, $C_{1-10}$ groups having one or more, e.g., 1, 2, 3, 4, or 5, carbon-to-carbon double bonds. "Substituted alkene" refers to alkene substituted at 1 or more, e.g., 1, 2, 3, 4, or 5 positions, which substituents are attached at any available atom to produce a stable compound, with substitution as described herein.

"Optionally substituted alkene" refers to alkene or substituted alkene. Likewise, "alkenylene" refers to divalent alkene. Examples of alkenylene include without limitation, ethenylene (—CH═CH—) and all stereoisomeric and conformational isomeric forms thereof. "Substituted alkenylene" refers to divalent substituted alkene. "Optionally substituted alkenylene" refers to alkenylene or substituted alkenylene.

"Alkyne or alkynyl" refers to a straight or branched chain unsaturated hydrocarbon having the indicated number of carbon atoms and at least one triple bond. Examples of a ($C_2$-$C_8$)alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein below. The term "alkynylene" refers to divalent alkyne. Examples of alkynylene include without limitation, ethynylene, propynylene. "Substituted alkynylene" refers to divalent substituted alkyne.

The term "alkoxy" refers to an —O-alkyl group having the indicated number of carbon atoms. For example, a ($C_1$-$C_6$)alkoxy group includes —O-methyl (methoxy), —O-ethyl (ethoxy), —O-propyl (propoxy), —O-isopropyl (isopropoxy), —O-butyl (butoxy), —O-sec-butyl (sec-butoxy), —O-tert-butyl (tert-butoxy), —O-pentyl (pentoxy), —O—isopentyl (isopentoxy), —O-neopentyl (neopentoxy), —O-hexyl (hexyloxy), —O-isohexyl (isohexyloxy), and —O-neohexyl (neohexyloxy). "Hydroxyalkyl" refers to a ($C_{1-10}$) alkyl group wherein one or more of the alkyl group's hydrogen atoms is replaced with an —OH group. Examples of hydroxyalkyl groups include, but are not limited to, —$CH_2OH$, —$CH_2CH_2OH$, —$CH_2CH_2CH_2OH$, —$CH_2CH_2CH_2CH_2OH$, —$CH_2CH_2CH_2CH_2CH_2OH$, —$CH_2CH_2CH_2CH_2CH_2CH_2OH$, and branched versions thereof. The term "ether" or "oxygen ether" refers to ($C_1$-$C_{10}$)alkyl group wherein one or more of the alkyl group's carbon atoms is replaced with an —O— group. The term ether includes —$CH_2$—(O$CH_2$—$CH_2$)$_q$O$P_1$ compounds where $P_1$ is a protecting group, —H, or a ($C_1$-$C_{10}$)alkyl. Exemplary ethers include polyethylene glycol, diethylether, methylhexyl ether and the like.

The term "thioether" refers to ($C_1$-$C_{10}$)alkyl group wherein one or more of the alkyl group's carbon atoms is replaced with an —S— group. The term thioether includes —$CH_2$—(S$CH_2$—$CH_2$)$_q$—S$P_1$ compounds where $P_1$ is a protecting group, —H, or a ($C_1$-$C_{10}$)alkyl. Exemplary thioethers include dimethylthioether, ethylmethyl thioether. Protecting groups are known in the art and include, without limitation: 9-fluorenylmethyloxy carbonyl (Fmoc), t-butyloxycarbonyl (Boc), benzhydryloxycarbonyl (Bhoc), benzyloxycarbonyl (Cbz), O-nitroveratryloxycarbonyl (Nvoc), benzyl (Bn), allyloxycarbonyl (alloc), trityl (Trt), dimethoxytrityl (DMT), 1-(4,4-dimethyl-2,6-dioxacyclohexylidene)ethyl (Dde), diathiasuccinoyl (Dts), benzothiazole-2-sulfonyl (Bts) and monomethoxytrityl (MMT) groups.

"Aryl," alone or in combination refers to an aromatic monocyclic or bicyclic ring system such as phenyl or naphthyl. "Aryl" also includes aromatic ring systems that are optionally fused with a cycloalkyl ring. A "substituted aryl" is an aryl that is independently substituted with one or more substituents attached at any available atom to produce a stable compound, wherein the substituents are as described herein. "Optionally substituted aryl" refers to aryl or substituted aryl. "Arylene" denotes divalent aryl, and "substituted arylene" refers to divalent substituted aryl. "Optionally substituted arylene" refers to arylene or substituted arylene.

"Heteroatom" refers to N, O, P and S. Compounds that contain N or S atoms can be optionally oxidized to the corresponding N-oxide, sulfoxide or sulfone compounds. "Hetero-substituted" refers to an organic compound in any embodiment described herein in which one or more carbon atoms are substituted with N, O, P or S.

"Cycloalkyl" refer to monocyclic, bicyclic, tricyclic, or polycyclic, 3- to 14-membered ring systems, which are either saturated, unsaturated or aromatic. The cycloalkyl group may be attached via any atom. Cycloalkyl also contemplates fused rings wherein the cycloalkyl is fused to an aryl or hetroaryl ring. Representative examples of cycloalkyl include, but are not limited to cyclopropyl, cyclobutyl, cyclopentyl, and cyclohexyl. A cycloalkyl group can be unsubstituted or optionally substituted with one or more substituents as described herein below. "Cycloalkylene" refers to divalent cycloalkyl. The term "optionally substituted cycloalkylene" refers to cycloalkylene that is substituted with 1, 2 or 3 substituents, attached at any available atom to produce a stable compound, wherein the substituents are as described herein.

"Carboxyl" or "carboxylic" refers to group having the indicated number of carbon atoms and terminating in a —C(O)OH group, thus having the structure —R—C(O)OH, where R is a divalent organic group that includes linear, branched, or cyclic hydrocarbons. Non-limiting examples of these include: $C_{1-8}$ carboxylic groups, such as ethanoic, propanoic, 2-methylpropanoic, butanoic, 2,2-dimethylpropanoic, pentanoic, etc.

"$(C_3-C_8)$aryl-$(C_1-C_6)$alkylene" refers to a divalent alkylene wherein one or more hydrogen atoms in the $C_1-C_6$ alkylene group is replaced by a $(C_3-C_8)$aryl group. Examples of $(C_3-C_8)$aryl-$(C_1-C_6)$alkylene groups include without limitation 1-phenylbutylene, phenyl-2-butylene, I-phenyl-2-methylpropylene, phenylmethylene, phenylpropylene, and naphthylethylene. The term "$(C_3-C_8)$cycloalkyl-$(C_1-C_6)$alkylene" refers to a divalent alkylene wherein one or more hydrogen atoms in the $C_1-C_6$ alkylene group is replaced by a $(C_3-C_8)$cycloalkyl group. Examples of $(C_3-C_8)$cycloalkyl-$(C_1-C_6)$alkylene groups include without limitation 1-cycloproylbutylene, cycloproyl-2-butylene, cyclopentyl-1-phenyl-2-methylpropylene, cyclobutylmethylene and cyclohexylpropylene.

Provided herein are nucleic acids and analogs thereof, collectively "genetic recognition reagents" (genetic recognition reagent), that bind specifically to two nucleic acid strands, whether or not the two strands are independent strands, two portions of a single strand (e.g., in a hairpin), or contain mismatches in the sense that at one or more positions within the two strands at the site of binding to the genetic recognition reagents, the bases are not able to base pair according to traditional Watson-Crick base pairing (A-T/U, T/U-A, G-C or C-G). The genetic recognition reagent comprises a plurality of nucleobase moieties, each attached to a nucleic acid or nucleic acid analog backbone monomer residue, and forming a part of the larger genetic recognition reagent comprising at least two nucleic acid or nucleic acid monomer residues, and therefore at least two nucleobases (nucleobase moieties). In one aspect, the two strands binding the genetic recognition reagent are non-complementary, meaning they do not hybridize under physiological conditions and typically contain less than 50% complementarity, meaning that less than 50% of the bases in the two strands are mismatched when aligned to nucleobases of the genetic recognition reagent. Thus, depending upon choice of nucleobases in the sequence, the genetic recognition reagents described herein can invade or otherwise hybridize to two strands of fully-complementary, partially-complementary or non-complementary double-stranded nucleic acids.

In one aspect, the genetic recognition reagents described herein comprise all divalent nucleobases. In another embodiment, the genetic recognition reagents described herein comprise at least one divalent nucleobases, with other nucleobases being monovalent. As used herein, a monovalent nucleobase binds one nucleobase on a single nucleic acid strand, while a divalent nucleobase binds to two nucleobases, one on a first nucleic acid strand, and another on a second nucleic acid strand.

Figure 1B:
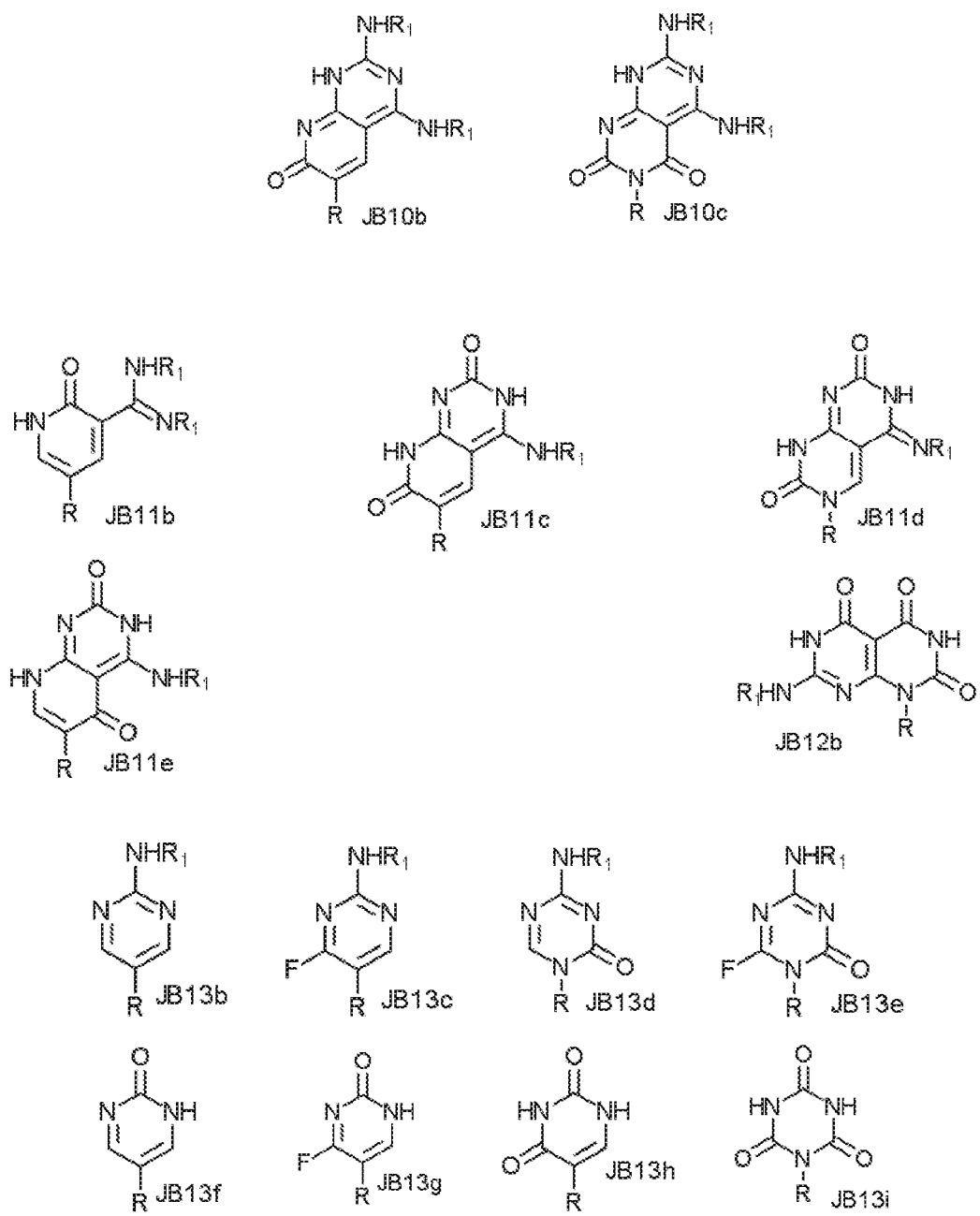

Thus in one aspect, divalent nucleobases are provided. Those nucleobases can be incorporated into a genetic recognition reagent monomer, which can then be incorporated into an oligomer of monomers with a desired sequence of nucleobases. Table 1 provides binding specificities of the divalent nucleobases provided herein FIGS. 1A and 1B provide structures for the nucleobases.

TABLE 1

Divalent Nucleobase binding

| Nucleobase | Bases represented |
|---|---|
| JB1b, JB1c, and JB1d | T(U)/D* |
| JB2b | D/T(U) |
| JB3b | G/C |
| JB4b, JB4c, JB4d, and JB4e | C/G |
| JB5b, JB5c, and JB5d | C/C |
| JB6b | T(U)/T(U) |
| JB7e and JB7f | G/G |
| JB8b | D/D |
| JB9c | A/C |
| JB10b and JB10c | C/A |
| JB11b, JB11c, JB11d, and JB11e | T(U)/G |
| JB12b | G/T(U) |
| JB13b, JB13c, JB13d, JB13e, JB13f, JB13g, JB13h, and JB13i | C/T(U) |

*diaminopurine (D), an adenine analog

For the structures of FIGS. 1A and 1B, R refers to a covalently-linked group or moiety attached to the nucleobase moiety, such as, for example:

a reactive group that reacts, for example and without limitation, with a backbone monomer during synthesis of a monomer, non-limiting examples of which include: carboxyl (e.g., —C(O)OH), hydroxyl (e.g., —C—OH), amine, cyanate (e.g., —C—C≡N), thiol (e.g., —C—SH), epoxide (oxirane), vinyl, allyl, n-hydroxysuccinimide (NHS) ester, azide, alkynyl, maleimide, hydrazide, tetrazine, phosphoramidite, cycloalkyne, nitrile, —$(CH_2)_n CO_2 H$ or —$(CH_2)_n CO_2 Y$ (n=1-5, Y=any leaving group such as Cl, alkyl, aryl, etc.);

a backbone monomer moiety, as described herein, such as, without limitation, a ribose, deoxyribose, nucleic acid analog backbone monomer, or a peptide nucleic acid backbone monomer, as described in further detail herein;

a nucleic acid or nucleic acid analog as described in further detail herein;

a protecting group; or any covalently-linked group, moiety, composition, substrate, or device, such as, without limitation, H, halo, hydrocarbyl, substituted hydrocarbyl, a polymer, a substrate (e.g., a silicon chip or an implantable device), a protein or peptide, a ligand, a binding reagent such as an antibody, an antibody fragment, or other paratopecontaining moieties, or an aptamer, an affinity tag (e.g., epitope or a ligand such as biotin), or a receptor or fragment thereof, or a receptor-binding moiety.

R1 is H or a protecting group. Where instances of R1 are H, the amines of the compounds or moieties are said to be deprotected. Depending on the chemistries employed to prepare the monomers or polymers comprising the monomers, one or more amine is protected with R1 being a protecting group, as is needed. Protecting groups for amines, include, for example and without limitation: methyl, formyl, ethyl, acetyl, anisyl, benzyl, benzoyl, carbamate, trifluoroacetyl, diphenylmethyl, triphenylmethyl, N-hydroxysuccinimide, benzyloxymethyl, benzyloxycarbonyl, 2-nitrobenzoyl, t-Boc (tert-butyloxycarbonyl), 4-methylbenzyl, 4-nitrophenyl, 2-chlorobenzyloxycarbonyl, 2-bromobenzyloxycarbonyl, 2,4,5-trichlorophenyl, thioanizyl, thiocresyl, cbz (carbobenzyloxy), p-methoxybenzyl carbonyl, 9-fluorenylmethyloxycarbonyl, pentafluorophenyl, p-methoxybenzyl, 3,4-dimethozybenzyl, p-methoxyphenyl, 4-toluenesulfonyl, p-nitrobenzenesulfonates, 9-fluorenylmethyloxycarbonyl, 2-nitrophenylsulfenyl, 2,2, 5,7,8-pentamethyl-chroman-6-sulfonyl, and p-bromobenzenesulfonyl.

Figure 2A:
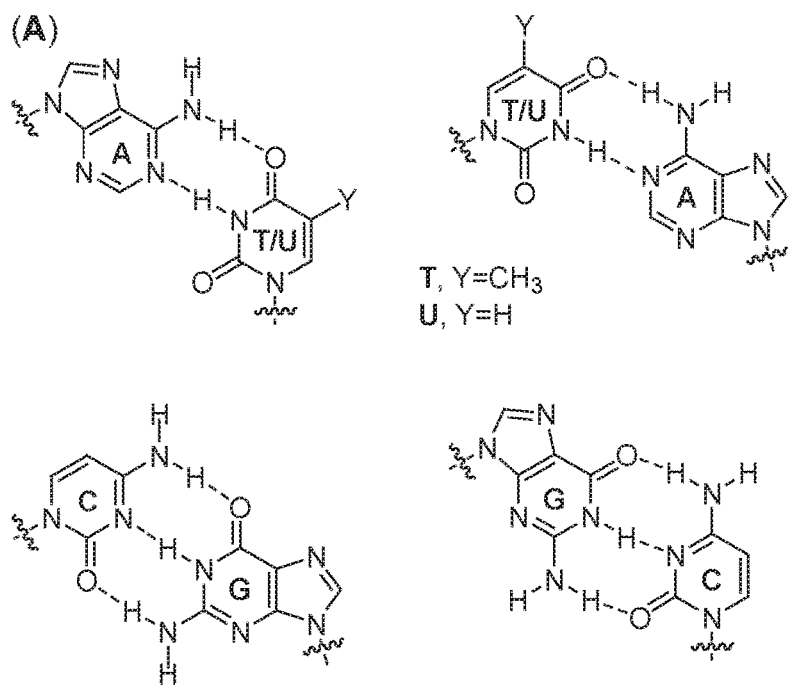
FIG. 2A illustrates hydrogen-bonding interactions between natural base-pairs.
Figure 2C:
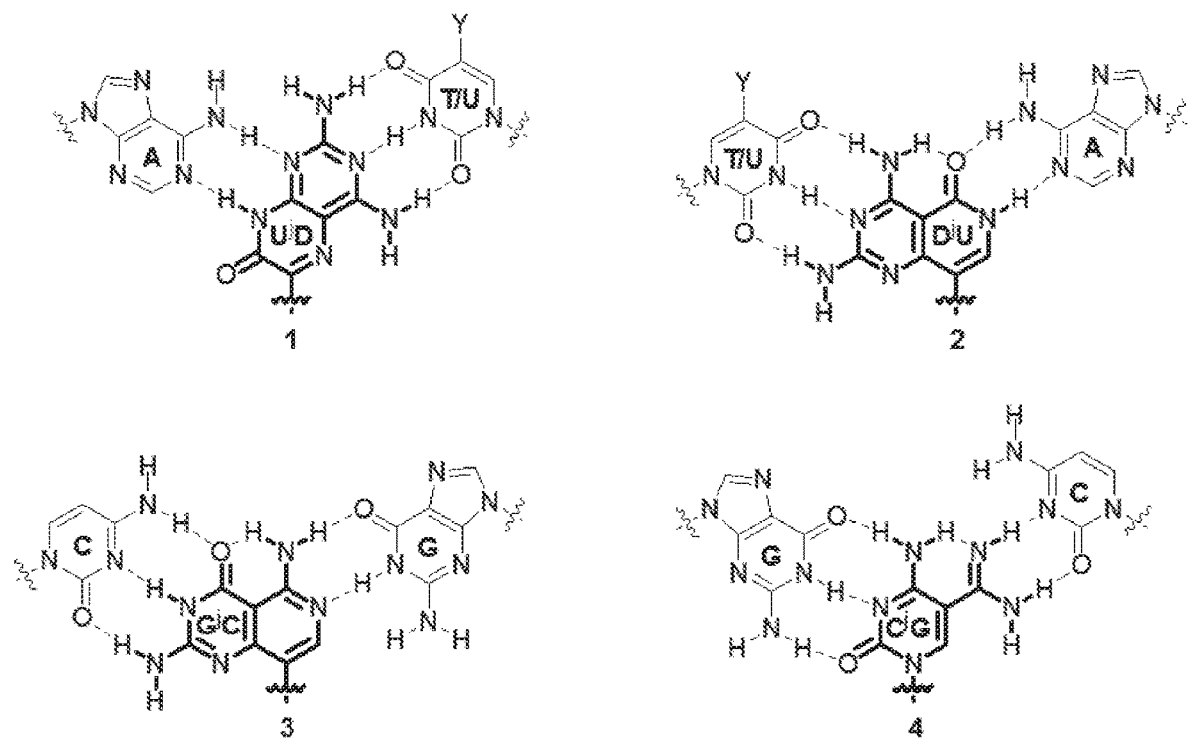
FIG. 2C depicts hydrogen-bonding interactions JB1-JB4 (labeled 1-4) and a perfectly-matched DNA or RNA target.
Figure 2B:
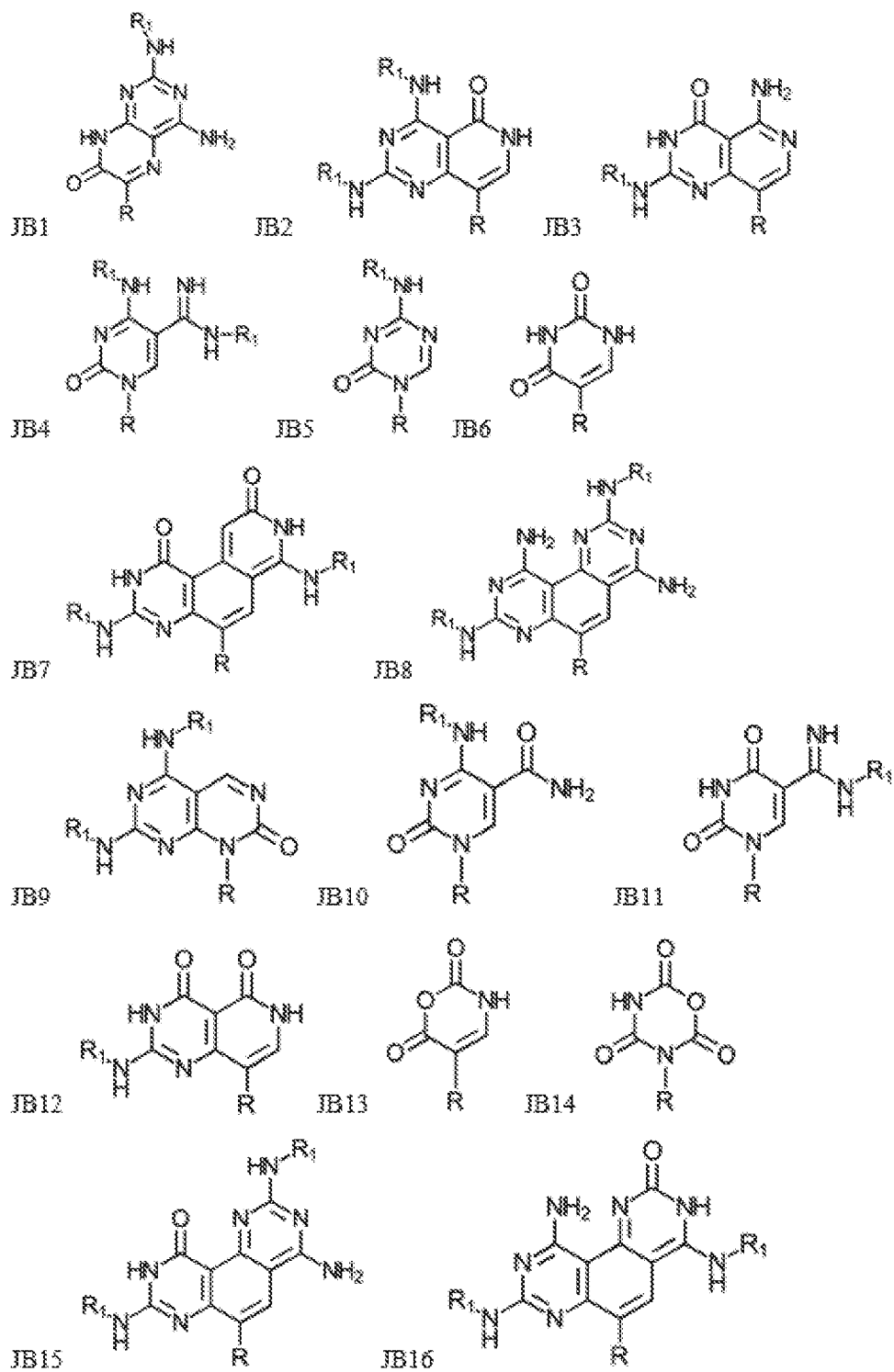
FIG. 2B depicts structures of first generation divalent nucleobases, as described in United States Patent Publication No. 20160083434 A1 (R1 and R are as defined below).
Figure 2D:
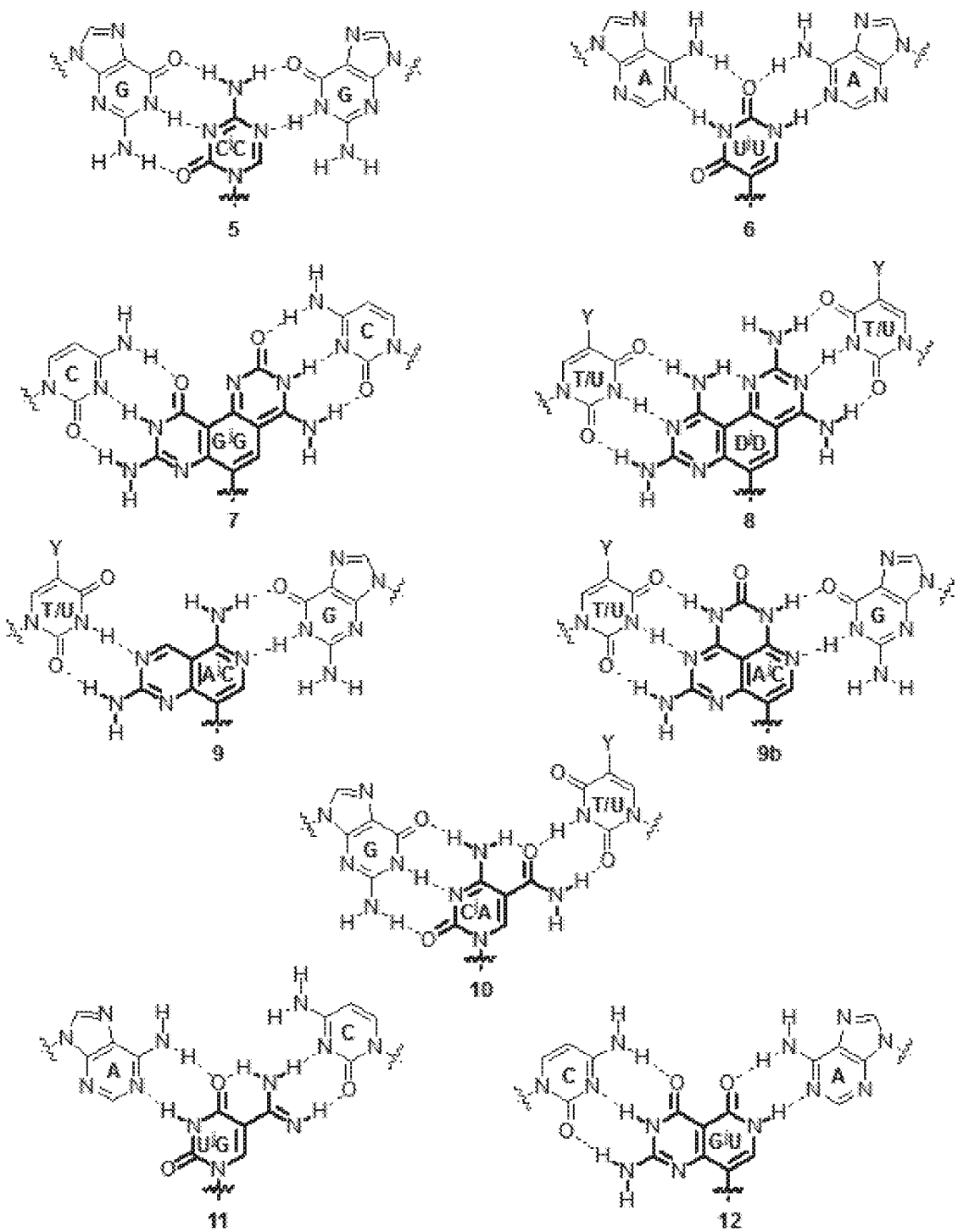
FIGS. 2D and 2E depict hydrogen-bonding interactions between JB5-JB16 (labeled 5-16) and a mismatched DNA or RNA target.
Figure 2E:
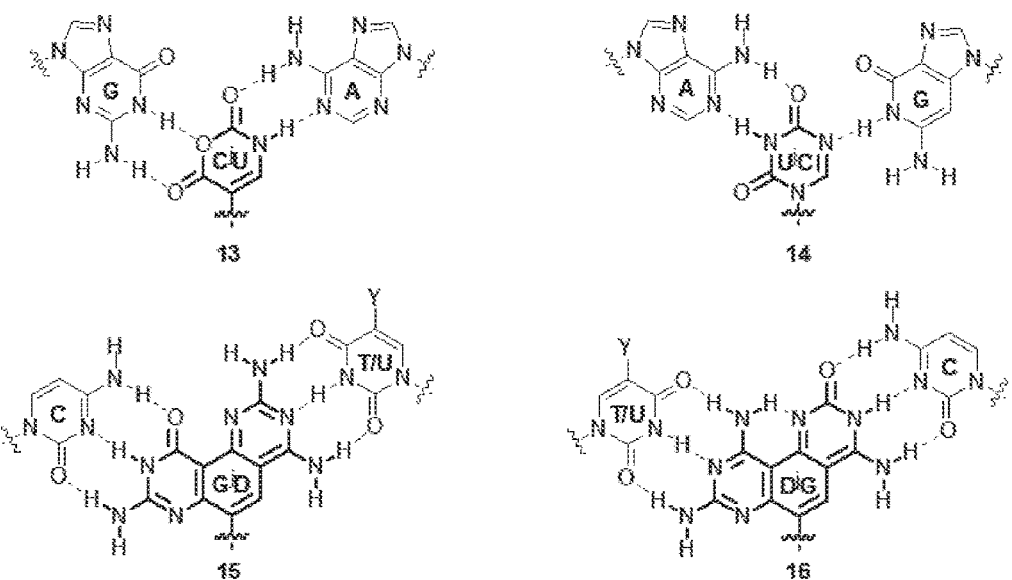

In the context of the present disclosure, a "nucleotide" refers to a monomer comprising at least one nucleobase and a backbone element, which in a nucleic acid, such as RNA or DNA is ribose or deoxyribose. "Nucleotides" also typically comprise reactive groups that permit polymerization under specific conditions. In native DNA and RNA, those reactive groups are the 5' phosphate and 3' hydroxyl groups. For chemical synthesis of nucleic acids and analogs thereof, the bases and backbone monomers may contain modified groups, such as blocked amines, as are known in the art. A "nucleotide residue" refers to a single nucleotide that is incorporated into an oligonucleotide or polynucleotide. Likewise, a "nucleobases residue" refers to a nucleobases incorporated into a nucleotide or a nucleic acid or analog thereof. A "genetic recognition reagent" refers generically to a nucleic acid or a nucleic acid analog that comprises a sequence of nucleobases that is able to hybridize to a complementary nucleic acid sequence on a nucleic acid by cooperative base pairing, e.g., Watson-Crick base pairing or Watson-Crick-like base pairing (see, FIG. 2A). United States Patent Publication No. 20160083434 A1 describes first generation counterparts of the divalent nucleobases described herein (see FIG. 2B providing structures for JB1-JB16, and FIGS. 2C-2E, showing hydrogen bonding of those compounds as illustration of the hydrogen bonding of the divalent nucleobases provided herein). As described in that publication, the first generation nucleobases JB1-JB4 bind naturally complementary bases (e.g., C-G, G-C, A-T and T-A), while JB5-JB16 bind mismatches, and thus can be used to bind two strands of matched and/or mismatched bases.

Divalent nucleobases described herein have the same base-pairing as their counterpart first-generation compounds. Nucleobases described herein that have the same nucleobase binding affinity as the first generation JB1-JB16 nucleobases are referred to as "JB #-series nucleobases" where # refers to the number of the first-generation nucleobase (JB1, JB2, JB3, JB4, JB5, JB6, JB7, JB8, JB9, JB9b, JB10, JB11, JB12, JB13, JB14, JB15, JB16 nucleobases, respectively) having the same nucleobase binding affinity. Reference to a JB #-series of nucleobases includes both the first generation and second generation nucleobases. For example JB1b, JB1c, and JB1d bind both A and T/U in the same order as JB1, and are therefore referred to as JB1- series nucleobases, inclusive of JB1; JB4b-e bind G and C in the same order as JB4, and are therefore referred to as JB4-series nucleobases, inclusive of JB4; and JB13b-i bind G and A in the same order as JB13, and are therefore referred to as JB13-series nucleobases, inclusive of JB13.

The compounds of FIGS. 1A and 1B are synthesized according to methods known in the chemical and organic synthesis arts. Illustrative synthesis schemes and spectra are provided in the Examples below, and additional synthesis schemes are provided in United States Patent Publication No. 20160083434 A1, incorporated herein by reference in its entirety.

The nucleobases of FIGS. 1A and 1B have divalent binding affinity, as indicated above. Of note, JB1-series, JB2-series, JB3-series and JB4-series compounds account for matched (complementary) sequences, while the remainder of the compounds bind mismatched sequences.

Figure 3:
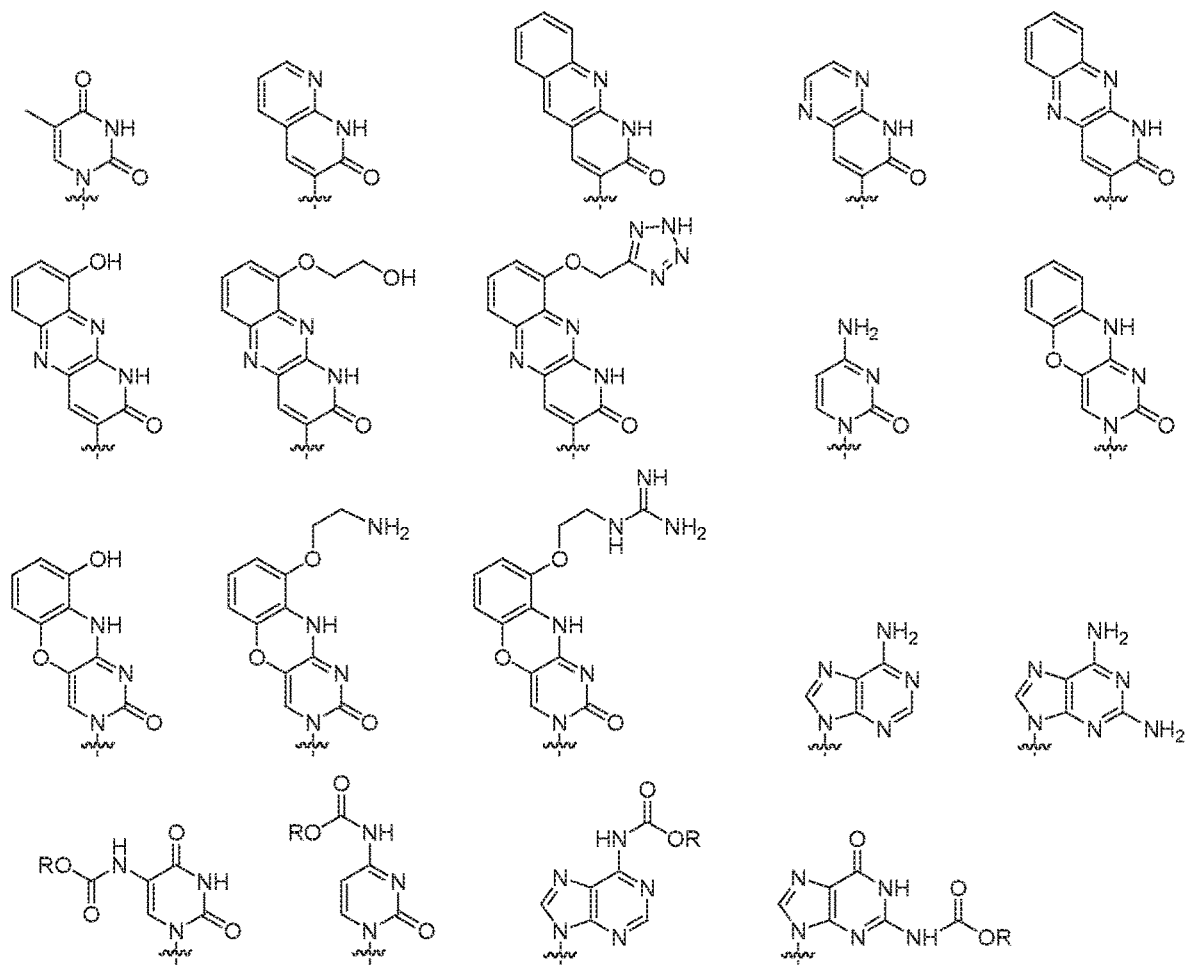
FIG. 3 provides structures of exemplary nucleobases.

In aspects, provided herein are divalent nucleobases. Nucleobases are recognition moieties that bind specifically to one or more of adenine, guanine, thymine, cytosine, and uracil, e.g., by Watson-Crick or Watson-Crick-like base pairing by hydrogen bonding. A "nucleobase" includes primary (natural) nucleobases: adenine, guanine, thymine, cytosine, and uracil, as well as modified purine and pyrimidine bases, such as, without limitation, hypoxanthine, xanthene, 7-methylguanine, 5, 6, dihydrouracil, 5-methylcytosine, and 5-hydroxymethylcytosine. FIG. 3 also depicts non-limiting examples of nucleobases, including monovalent nucleobases (e.g., adenine, cytosine, guanine, thymine or uracil, which bind to one strand of nucleic acid or nucleic acid analogs), and "clamp" nucleobases, such as a "G-clamp," which binds complementary nucleobases with enhanced strength. Additional purine, purine-like, pyrimidine and pyrimidine-like nucleobases are known in the art, for example as disclosed in U.S. Pat. Nos. 8,053,212, 8,389,703, and 8,653,254. Divalent nucleobases as described herein, bind two nucleobases instead of one and therefore can form trimeric structures with matched or mismatched nucleic acids.

Also provided herein are nucleotides having the structure A-B wherein A is a backbone monomer moiety and B is a divalent nucleobase as described above. The backbone monomer can be any suitable nucleic acid backbone monomer, such as a ribose triphosphate or deoxyribose triphosphate, or a monomer of a nucleic acid analog, such as peptide nucleic acid (PNA), such as a gamma PNA (γPNA). In one example the backbone monomer is a ribose mono-, di-, or tri-phosphate or a deoxyribose mono-, di-, or tri-phosphate, such as a 5' monophosphate, diphosphate, or triphosphate of ribose or deoxyribose. The backbone monomer includes both the structural "residue" component, such as the ribose in RNA, and any active groups that are modified in linking monomers together, such as the 5' triphosphate and 3' hydroxyl groups of a ribonucleotide, which are modified when polymerized into RNA to leave a phosphodiester linkage. Likewise for PNA, the C-terminal carboxyl and N-terminal amine active groups of the N-(2-aminoethyl)glycine backbone monomer are condensed during polymerization to leave a peptide (amide) bond. In another aspect, the active groups are phosphoramidite groups useful for phosphoramidite oligomer synthesis, as is broadly-known in the arts. The nucleotide also optionally comprises one or more protecting groups as are known in the art, such as 4,4'-dimethoxytrityl (DMT), and as described herein. A number of additional methods of preparing synthetic genetic recognition reagents are known, and depend on the backbone structure and particular chemistry of the base addition process. Determination of which active groups to utilize in joining nucleotide monomers and which groups to protect in the bases, and the required steps in preparation of oligomers is well within the abilities of those of ordinary skill in the chemical arts and in the particular field of nucleic acid and nucleic acid analog oligomer synthesis.

Figure 4:
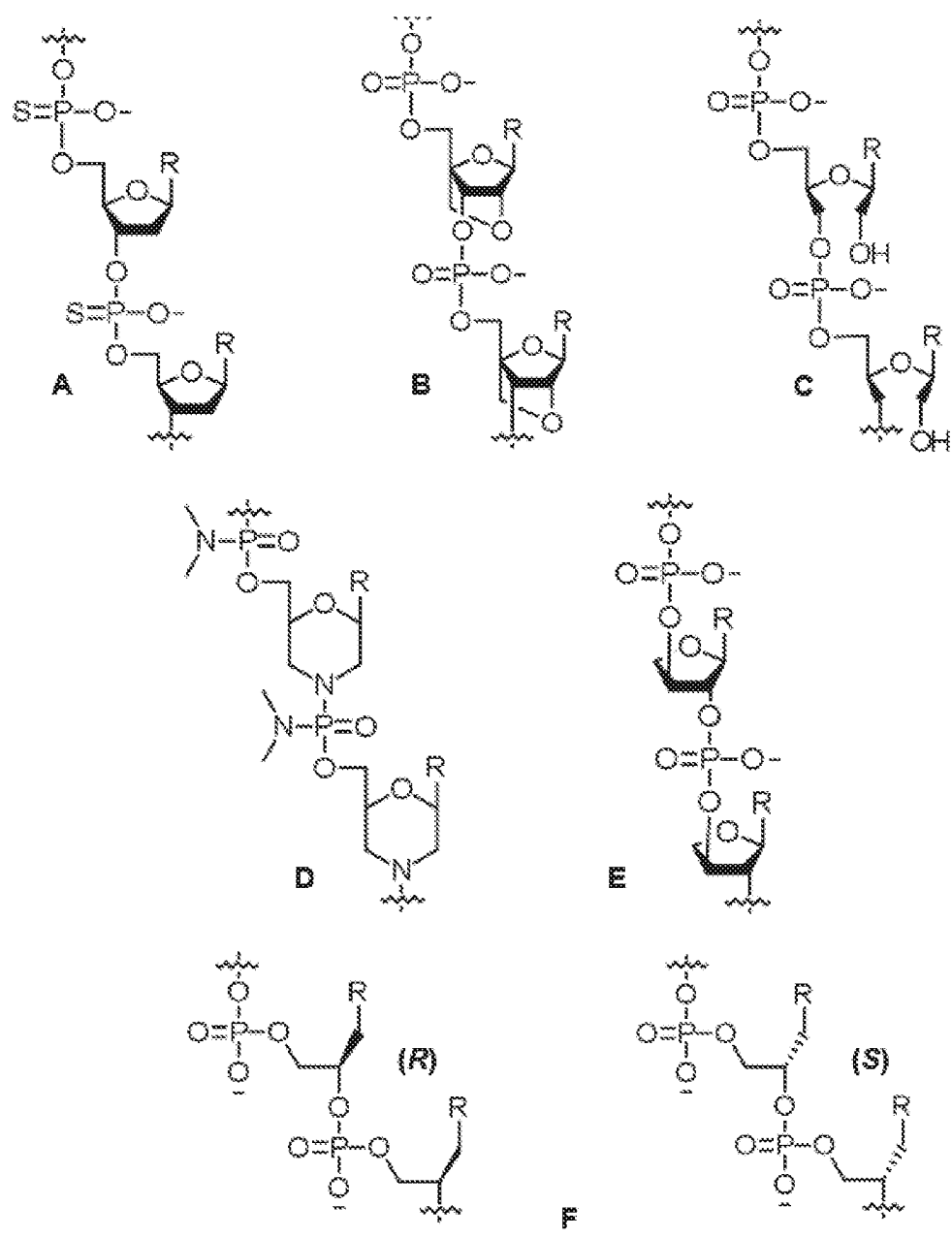
FIGS. 4(A-F) provide exemplary structures of nucleic acid analogs.

Non-limiting examples of common nucleic acid analogs include peptide nucleic acids, such as γPNA, phosphorothioate (e.g., FIG. 4(A)), locked nucleic acid (2'-O-4'-C-methylene bridge, including oxy, thio or amino versions thereof, e.g., FIG. 4(B)), unlocked nucleic acid (the C2'-C3' bond is cleaved, e.g., FIG. 4(C)), 2'-O-methyl-substituted RNA, morpholino nucleic acid (e.g., FIG. 4(D)), threose nucleic acid (e.g., FIG. 4(E)), glycol nucleic acid (e.g., FIG. 4(F), showing R and S Forms), etc. FIG. 4(A-F) shows monomer structures for various examples of nucleic acid analogs. FIGS. 4(A-F) each show two monomer residues incorporated into a longer chain as indicated by the wavy lines. Incorporated monomers are referred to herein as "residues" and the part of the nucleic acid or nucleic acid analog excluding the nucleobases is referred to as the "backbone" of the nucleic acid or nucleic acid analog. As an example, for RNA, an exemplary nucleobase is adenine, a corresponding monomer is adenosine triphosphate, and the incorporated residue is an adenosine monophosphate residue. For RNA, the "backbone" consists of ribose subunits linked by phosphates, and thus the backbone monomer is ribose triphosphate prior to incorporation and a ribose monophosphate residue after incorporation.

According to one aspect, with the advent of conformationally-preorganized γPNA (Bahal, R., et al. "Sequence-unrestricted, Watson-Crick recognition of double helical B-DNA by (R)-MiniPEG-γPNAs (2012) ChemBioChem 13:56-60), γPNA can be designed to bind to any sequence of double helical B-DNA based on the well-established rules of Watson-Crick base-pairing. However, with an arsenal of only natural nucleobases as recognition elements, strand invasion of DNA by γPNA is confined to sub-physiological ionic strengths (Rapireddy, S., R. et al. "Strand invasion of mixed-sequence, double-helical B-DNA by γ-peptide nucleic acids containing G-clamp nucleobases under physiological conditions," (2011) Biochemistry 50:3913-3918). A reduction in the efficiency of productive γPNA binding at elevated ionic strengths is not due to the lack of base-pair accessibility, but rather due to the lack of binding free energy. Under physiological conditions, DNA double helix is sufficiently dynamic to permit strand invasion, provided that the required binding free energy could be met. One way to improve the binding free energy of such a system would be to enhance the base-stacking and H-bonding capabilities of the recognition elements, which is met by the present invention. In one aspect, γPNA monomers and oligomers containing a specialized set of divalent nucleobases that are capable of forming directional hydrogen bonding interactions with both strands of the DNA or RNA double helix is provided. Examples of the chemical structures of the divalent nucleobases are illustrated in FIGS. 1A and 1B. Non-limiting examples of γPNA monomers and oligomers are provided below, with, e.g., an amino acid side chain, or a PEGylated (polyethyleneglycol, or PEG) group at the chiral gamma carbon.

As used herein, the term "nucleic acid" refers to deoxyribonucleic acids (DNA) and ribonucleic acids (RNA). Nucleic acid analogs include, for example and without limitation: 2'-O-methyl-substituted RNA, locked nucleic acids, unlocked nucleic acids, triazole-linked DNA, peptide nucleic acids, morpholino oligomers, dideoxynucleotide oligomers, glycol nucleic acids, threose nucleic acids and combinations thereof including, optionally ribonucleotide or deoxyribonucleotide residue(s). Herein, "nucleic acid" and "oligonucleotide", which is a short, single-stranded structure made of up nucleotides, are used interchangeably. An oligonucleotide may be referred to by the length (i.e. number of nucleotides) of the strand, through the nomenclature "-mer". For example, an oligonucleotide of 22 nucleotides would be referred to as a 22-mer.

A "peptide nucleic acid" refers to a DNA or RNA analog or mimic in which the sugar phosphodiester backbone of the DNA or RNA is replaced by a N-(2-aminoethyl)glycine unit. A gamma PNA (γPNA) is an oligomer or polymer of gamma-modified N-(2-aminoethyl)glycine monomers of the following structure:

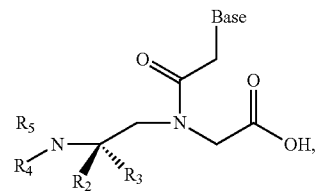

where at least one of $R_2$ or $R_3$ attached to the gamma carbon is not a hydrogen, or $R_2$ and $R_3$ are different, such that the gamma carbon is a chiral center. "Base" refers to a nucleobase, such as a divalent nucleobase according to any aspect described herein. When $R_2$ and $R_3$ are hydrogen (N-(2-aminoethyl)-glycine backbone), or the same, there is no such chirality about the gamma carbon. When $R_2$ and $R_3$ are different, such as when one of $R_2$ or $R_3$ are H and the other is not, there is chirality about the gamma carbon. Typically, for γPNAs and γPNA monomers, either of $R_2$ or $R_3$ is an H and the other is an amino acid sidechain or an organic group, such as a ($C_1$-$C_{10}$) organic group or hydrocarbon, optionally PEGylated with from 1 to 50 oxyethylene residues—that is, [—O—$CH_2$—$CH_2$-]n, where n is 1 to 50, inclusive. $R_4$ can be H or an organic group, such as a ($C_1$-$C_{10}$) organic group or hydrocarbon, optionally PEGylated with from 1 to 50 oxyethylene residues. For example and without limitation, $R_2$, $R_3$ and $R_4$ are, independently, H, amino acid side chains, linear or branched ($C_1$-$C_8$)alkyl, ($C_2$-$C_8$)alkenyl, ($C_2$-$C_8$)alkynyl, ($C_1$-$C_8$)hydroxyalkyl, ($C_3$-$C_8$)aryl, ($C_3$-$C_8$)cycloalkyl, ($C_3$-$C_8$)aryl($C_1$-$C_6$)alkylene, ($C_3$-$C_8$)cycloalkyl($C_1$-$C_6$) alkylene, PEGylated moieties of the preceding comprising from 1 to 50 (—O—$CH_2$—$CH_2$—) residues, —$CH_2$—(O$CH_2$—$CH_2$)$_q$O$P_1$, —$CH_2$—(O$CH_2$—$CH_2$)$_q$—NH$P_1$, —$CH_2$—(O$CH_2$—$CH_2$-0)$_q$—S$P_1$ and —$CH_2$—(S$CH_2$—$CH_2$)$_q$—S$P_1$, —$CH_2$—(O$CH_2$—$CH_2$)$_r$—OH, —$CH_2$—(O$CH_2$—$CH_2$)$_r$—NH$_2$, —$CH_2$—(O$CH_2$—$CH_2$)$_r$—NHC(NH)NH$_2$, or —$CH_2$—(O$CH_2$—$CH_2$)$_r$—S—S[$CH_2CH_2$]$_s$NHC(NH)NH$_2$, where $P_1$ is selected from the group consisting of H, ($C_1$-$C_8$)alkyl, ($C_2$-$C_8$)alkenyl, ($C_2$-$C_8$)alkynyl, ($C_3$-$C_8$)aryl, ($C_3$-$C_8$)cycloalkyl, ($C_3$-$C_8$)aryl($C_1$-$C_6$)alkylene and ($C_3$-$C_8$)cycloalkyl($C_1$-$C_6$)alkylene; q is an integer from 0 to 10, inclusive; r and s are each independently integers from 1 to 50, inclusive; where $R_2$ and $R_3$ are different, and optionally one of $R_2$ or $R_3$ is H. $R_5$ is H or a protective group.

Figure 5:
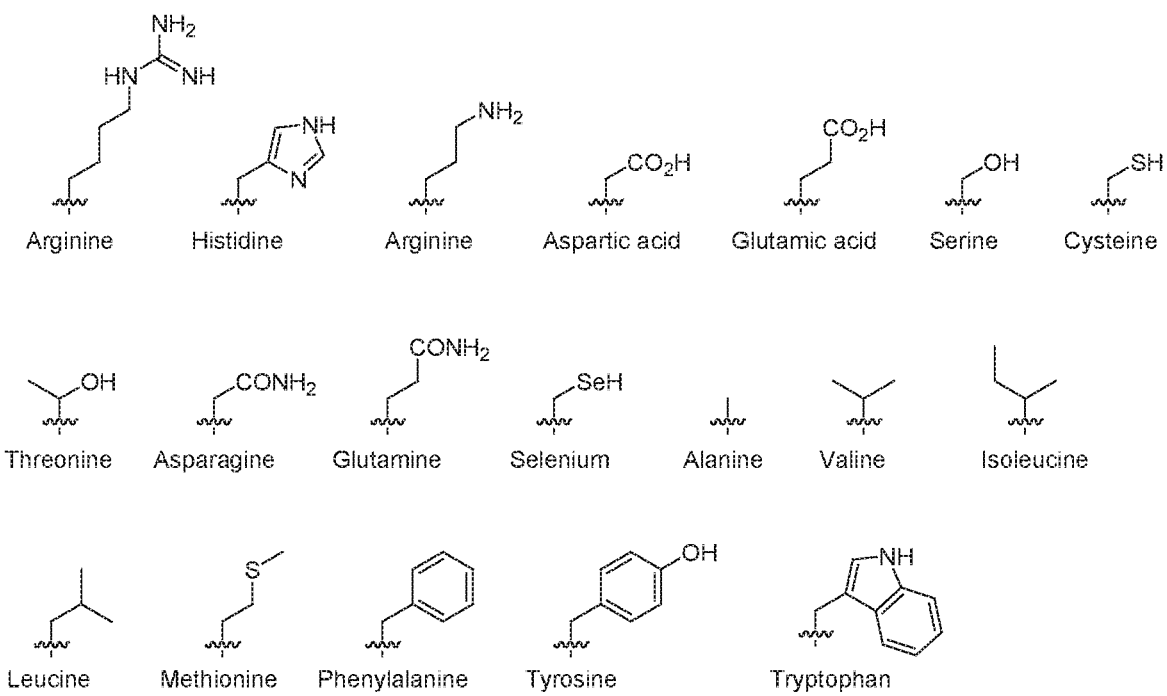
FIG. 5 provides examples of amino acid side chains.

An "amino acid side chain" is a side chain for an amino acid. Amino acids have the structure:

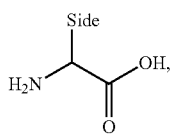

where "Side" is the amino acid side chain. Non-limiting examples of amino acid side chains are shown in FIG. 5. Glycine is not represented because in the embodiment there is no side chain (Side=H).

A γPNA monomer incorporated into a γPNA oligomer or polymer,

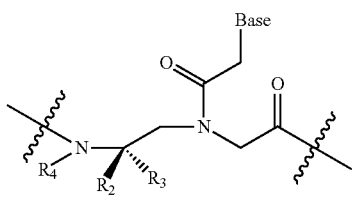

(where $R_2$, $R_4$, $R_4$, and Base are as defined above) is referred to herein as a "γPNA monomer residue", with each residue having the same or different Base group as its nucleobase, such as adenine, guanine, cytosine, thymine and uracil bases, or other nucleobases, such as the monovalent and divalent bases described herein, such that the order of bases on the γPNA is its "sequence", as with DNA or RNA. The depicted γPNA residue structure shows a backbone monomer residue attached to a nucleobase (Base). A sequence of nucleobases in a nucleic acid or a nucleic acid analog oligomer or polymer, such as a γPNA oligomer or polymer, binds to a complementary sequence of adenine, guanine, cytosine, thymine and/or uracil residues in a nucleic acid strand by cooperative bonding, essentially as with Watson-Crick binding of complementary bases in double-stranded DNA or RNA. "Watson-Crick-like" bonding refers to hydrogen bonding of nucleobases other than G, A, T, C or U, such as the bonding of the divalent bases shown herein with G, A, T, C, U or other nucleobases.

Unless otherwise indicated, the nucleic acids and nucleic acid analogs described herein are not described with respect to any particular sequence of bases. The present disclosure is directed to divalent nucleobases, compositions comprising the divalent nucleobases, and methods of use of the divalent nucleobases and compounds containing those nucleobases, and the usefulness of any specific embodiments described herein, while depending upon a specific sequence in each instance, is generically applicable. Based on the abundance of published work with nucleic acids, nucleic acid analogs and PNA (e.g., γPNA), it is expected that any nucleobase sequence attached to the backbone of the described γPNA oligomers would hybridize in an expected, specific manner with a complementary nucleobase sequence of a target nucleic acid or nucleic acid analog by Watson-Crick or Watson-Crick-like hydrogen bonding. One of ordinary skill would understand that the compositions and methods described herein are sequence-independent and describe novel, generalized compositions comprising divalent nucleobases and related methods.

In another aspect, a genetic recognition reagent oligomer is provided, comprising at least one divalent nucleobase. The genetic recognition reagent comprises a backbone and at least two nucleobases, at least one of which is a divalent nucleobase as described herein. An exemplary structure is:

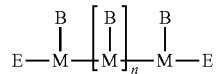

where each instance of M is a backbone monomer residue, and each instance of B is, independently a nucleobase in any sequence, where at least one instance of B is a divalent nucleobase according to any aspect as described herein, e.g. is selected from: JB1b, JB1c, JB1d, JB2b, JB3b, JB4b, JB4c, JB4d, JB4e, JB5b, JB5c, JB5d, JB6b, JB7e, JB7f, JB8b, JB9c, JB10b, JB10c, JB11b, JB11c, JB11d, JB11e, JB12b, JB13b, JB13c, JB13d, JB13e, JB13f, JB13g, JB13h, and JB13i. E are independently end (terminal) groups that are part of the terminal monomer residues, and "n" is any positive integer or 0, for example 48 or less, 28 or less, 23 or less, and 18 or less, including 0, 1, 2, 3, 4, 5, 6, 7, 8, 9, 10, 11, 12, 13, 14, 15, 16, 17, and 18. Typically, all instances of M are the same with the exception of the terminal monomer residues which typically have different end-groups E as compared to internal monomers, such as, without limitation $NH_2$ and C(O)OH or $CONH_2$ at the respective N-terminal and C-terminal ends for PNAs, and hydroxyl groups at the 5' and 3' ends of nucleic acids.

Genetic recognition reagents can be prepared as small oligonucleotides and can be assembled in situ, in vivo, ex vivo, or in vitro, for example as described in United States Patent Application Publication No. 20160083433 A1, incorporated herein by reference in its entirety. By that method, small oligomers of high cell or tissue permeability as compared to longer sequences, such as trimers, can be transferred to a cell, and the oligomers can be assembled as a contiguous larger sequence once hybridized to a template nucleic acid. The same can be accomplished in vitro or ex vivo, for example, for rapidly assembling a longer sequence for use in hybridizing to a target nucleic acid.

In one aspect, the genetic recognition reagent is provided on an array. Arrays are particularly useful in implementing high-throughput assays, such as genetic detection assays. As used herein, the term "array" refers to reagents, for example the genetic recognition reagents described herein, located or attached at two or more discrete, identifiable and/or addressable locations on a substrate. In one aspect, an array is an apparatus having two or more discrete, identifiable reaction chambers, such as, without limitation a 96-well dish, in which reactions comprising identified constituents are performed. In one aspect, two or more genetic recognition reagents comprising one or more divalent nucleobases as described herein are immobilized onto a substrate in a spatially addressable manner so that each individual primer or probe is located at a different and (addressable) identifiable location on the substrate. One or more genetic recognition reagent is either covalently-linked to the substrate or are otherwise bound or located at addressable locations on the array. Substrates include, without limitation, multi-well plates, silicon chips and beads. In one aspect, the array comprises two or more sets of beads, with each bead set having an identifiable marker, such as a quantum dot or fluorescent tag, so that the beads are individually identifiable using, for example and without limitation, a flow cytometer. In one aspect, an array is a multi-well plate containing two or more wells with the described genetic recognition reagents for binding specific sequences. As such, reagents, such as probes and primers may be bound or otherwise deposited onto or into, or otherwise located at specific locations on an array. Reagents may be in any suitable form, including, without limitation: in solution, dried, lyophilized, or glassified. When linked covalently to a substrate, such as an agarose bead or silicon chip, a variety of linking technologies are known for attaching chemical moieties, such as the genetic recognition reagents to such substrates. Linkers and spacers for use in linking nucleic acids, peptide nucleic acids and other nucleic acid analogs are broadly known in the chemical and array arts and for that reason are not described herein. As a non-limiting example, a γPNA genetic recognition reagent contains a reactive amine, which can be reacted with carboxyl-, cyanogen bromide-, N-hydroxysuccinimide ester-, carbonyldiimidazole-, or aldehyde-functional agarose beads, available, for instance from Thermo Fisher Scientific (Pierce Protein Biology Products), Rockford, Ill., and a variety of other sources. The genetic recognition reagents described herein can be attached to a substrate in any manner, with or without linkers. Devices for use in conducting reactions, and for reading arrays are broadly-known and available, and informatics and/or statistical software or other computer-implemented processes for analyzing array data and/or identifying genetic risk factors from data obtained from a patient sample, are known in the art.

Certain of the divalent compositions described exhibit fluorescence, such as JB1, JB2 and JB3, due to their ring structure, with the triple-ring compounds, such as JB7e, JB7f, and JB8b, showing the greatest fluorescence and the double-ring structures also showing fluorescence. These compositions can be used as fluorochromes, or the intrinsic fluorescence can be employed as a probe, for example, by binding target sequences in an in situ assay or in a gel or blot, such that a target sequence can be visualized.

According to one aspect of the present invention, a method is provided for detection of a target sequence in a nucleic acid, comprising contacting a genetic recognition reagent composition as described herein with a sample comprising nucleic acid and detecting binding of the genetic recognition reagent with a nucleic acid. In one aspect, the genetic recognition reagent is immobilized on a substrate, for example in an array, and labeled (e.g., fluorescently labeled or radiolabeled) nucleic acid sample is contacted with the immobilized genetic recognition reagent and the amount of labeled nucleic acid specifically bound to the genetic recognition reagent is measured. In a variation, genetic recognition reagent or a nucleic acid comprising a target sequence of the genetic recognition reagent is bound to a substrate, and a labeled nucleic acid comprising a target sequence of the genetic recognition reagent or a labeled genetic recognition reagent is bound to the immobilized genetic recognition reagent or nucleic acid, respectively to form a complex. In one aspect, the nucleic acid of the complex comprises a partial target sequence so that a nucleic acid comprising the full target sequence would out-compete the complexed nucleic acid for the genetic recognition reagent. The complex is then exposed to a nucleic acid sample and loss of bound label from the complex could be detected and quantified according to standard methods, facilitating quantification of a nucleic acid marker in the nucleic acid sample. These are merely two of a large number of possible analytical assays that can be used to detect or quantify the presence of a specific nucleic acid in a nucleic acid sample.

By "immobilized" in reference to a composition such as a nucleic acid or genetic recognition reagent as described herein, it is meant attached to a substrate of any physical structure or chemical composition. The immobilized composition is immobilized by any method useful in the context of the end use. The composition is immobilized by covalent or non-covalent methods, such as by covalent linkage of amine groups to a linker or spacer, or by non-covalent bonding, including Van derWaals and/or hydrogen bonding. A "label" is a chemical moiety that is useful in detection of, or purification or a molecule or composition comprising the label. A label may be, for example and without limitation, a radioactive moiety, such as $^{14}C$, $^{32}P$, $^{35}S$, a fluorescent dye, such as fluorescein isothiocyanate or a cyanine dye, an enzyme, or a ligand for binding other compounds such as biotin for binding streptavidin, or an epitope for binding an antibody. A multitude of such labels, and methods of use thereof are known to those of ordinary skill in the immunology and molecular biology arts. That said, because certain divalent nucleobases described herein are highly-fluorescent, incorporation of such bases into nucleotide residues of a nucleic acid or nucleic acid analog, or covalently-linking a divalent nucleobase to a nucleic acid, nucleic acid analog, binding reagent, ligand or other detection reagent can permit detection of and/or quantification of a reagent in a sample, reaction mixture, array, etc.

In yet another aspect of the present invention, a method of isolation and purification or a nucleic acid containing a target sequence is provided. In one non-limiting aspect, a genetic recognition reagent as described herein is immobilized on a substrate, such as a bead (for example and without limitation, an agarose bead, a bead containing a fluorescent marker for sorting, or a magnetic bead), porous matrix, surface, tube, etc. A nucleic acid sample is contacted with the immobilized genetic recognition reagent and nucleic acids containing the target sequence bind to the genetic recognition reagent. The bound nucleic acid is then washed to remove unbound nucleic acids, and the bound nucleic acid is then eluted, and can be precipitated or otherwise concentrated by any useful method as are broadly known in the molecular biological arts.

In a further aspect, kits are provided. A kit comprises at a minimum a vessel of any form, including cartridges for automated nucleic acid, nucleic acid analog, or PNA synthesis, which may comprise one or more vessels in the form of individual and independent, optionally independently-addressable compartments, for use, for example, in an automatic sequence preparation device for preparing nucleic acids and/or nucleic acid analogs. Vessels may be single-use, or contain sufficient contents for multiple uses. A kit also may comprise an array. A kit may optionally comprise one or more additional reagents for use in making or using genetic recognition reagents in any embodiment described herein. The kit comprises a vessel containing any divalent nucleobase in any form described herein, or monomers or genetic recognition reagents according to any aspect described herein. Different nucleobases, monomers or genetic recognition reagents are typically packaged into separate vessels, which may be separate compartments in a cartridge.

In aspects, the compounds and genetic recognition reagents are used for therapeutic purposes and therefore those compounds and genetic recognition reagents are formulated in a drug product, pharmaceutical composition, or dosage form, including compositions for human and veterinary use, including a therapeutically effective amount of the compound or genetic recognition reagent and an excipient, e.g., a vehicle or diluent for therapeutic delivery, e.g., and without limitation, for oral, topical, intravenous, intramuscular, or subcutaneous administration. The composition can be formulated in a classical manner using solid or liquid vehicles, diluents and additives appropriate to the desired mode of administration. Orally, the compounds can be administered in the form of tablets, capsules, granules, powders and the like. The compositions optionally comprise one or more additional active agents, as are broadly known in the pharmaceutical, medicinal, veterinary or biological arts. The compounds described herein may be administered in any effective manner. Further examples of delivery routes include, without limitation: topical, for example, epicutaneous, inhalational, enema, ocular, otic and intranasal delivery; enteral, for example, orally, by gastric feeding tube or swallowing, and rectally; and parenteral, such as, intravenous, intraarterial, intramuscular, intracardiac, subcutaneous, intraosseous, intradermal, intrathecal, intraperitoneal, transdermal, iontophoretic, transmucosal, epidural and intravitreal. Therapeutic/pharmaceutical compositions are prepared in accordance with acceptable pharmaceutical procedures, as are broadly-known.

Any of the compounds described herein may be compounded or otherwise manufactured into a suitable composition for use, such as a pharmaceutical dosage form or drug product in which the compound or genetic recognition reagent is an active ingredient. According to one example, the drug product described herein is an oral tablet, capsule, caplet, liquid-filled or gel-filled capsule, etc. Compositions may comprise a pharmaceutically acceptable carrier, or excipient. An "excipient" is an inactive substance used as a carrier for the active ingredients of a medication. Although "inactive," excipients may facilitate and aid in increasing the delivery, stability or bioavailability of an active ingredient in a drug product. Non-limiting examples of useful excipients include: antiadherents, binders, rheology modifiers, coatings, disintegrants, emulsifiers, oils, buffers, salts, acids, bases, fillers, diluents, solvents, flavors, colorants, glidants, lubricants, preservatives, antioxidants, sorbents, vitamins, sweeteners, etc., as are available in the pharmaceutical/compounding arts.

The following examples are illustrative of various aspects of the invention.

Example

As indicated above, United States Patent Publication No. 20160083434 A1 describes first generation counterparts of the divalent nucleobases described herein and methods of synthesis of such compounds. Provided below are illustrative synthesis methods for selected second-generation nucleobases, and associated NMR data. Additional compounds described herein can be synthesized using standard chemical synthesis methods.

Example 1—Synthesis of Second-Generation Divalent Nucleobases

Figure 6A:
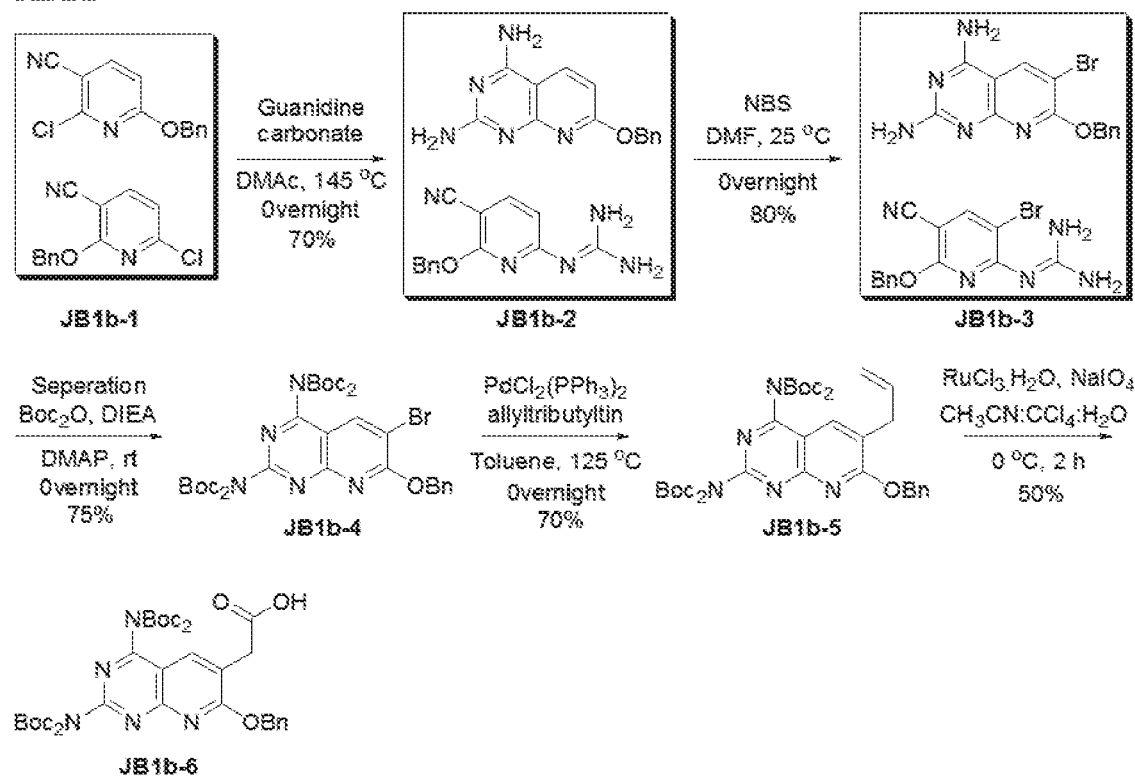
FIG. 6A shows the synthesis scheme for compound JB1b.
Figure 6B:
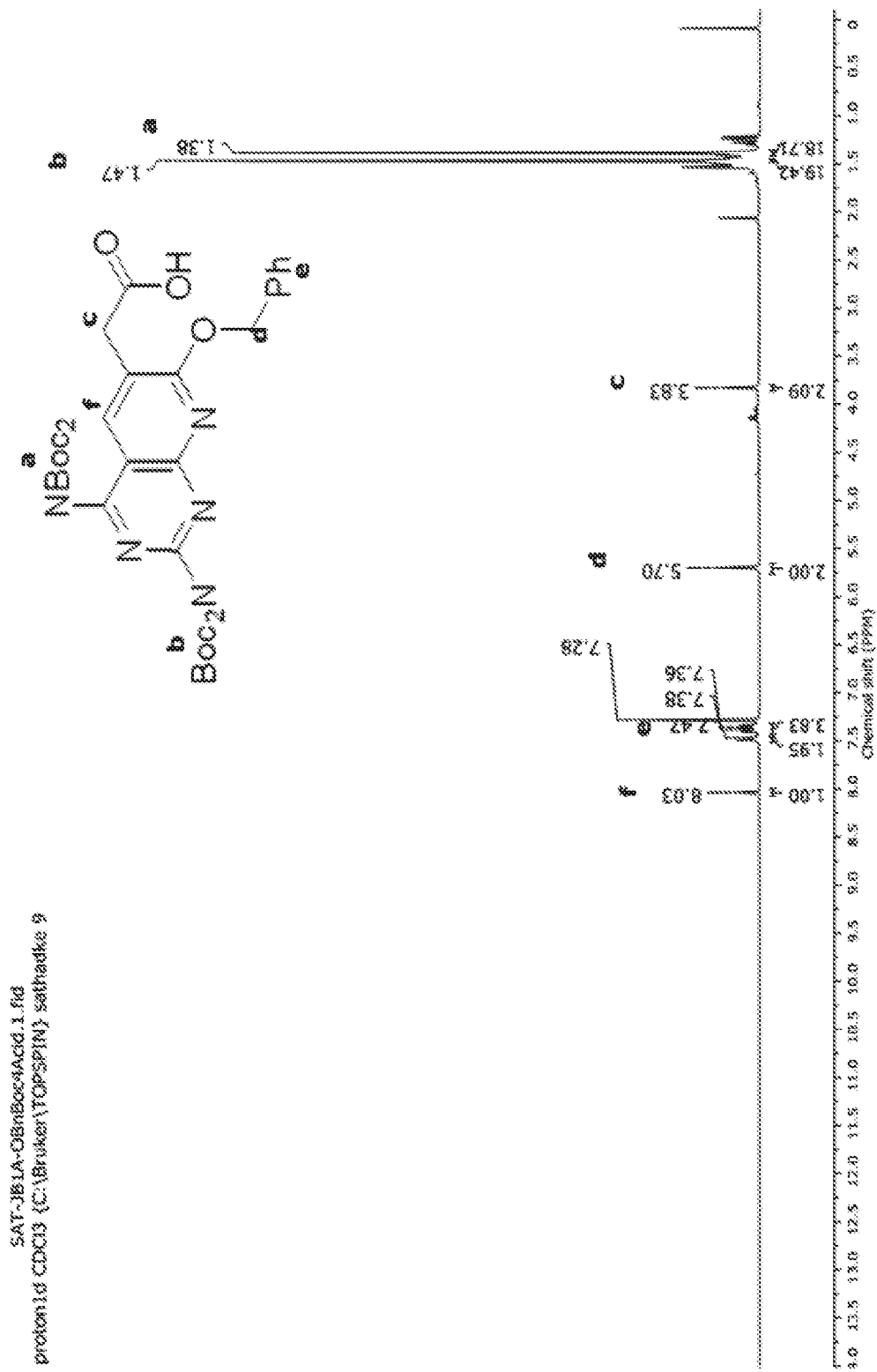
FIG. 6B provides an NMR spectrum of the JB1b-6 product.

FIGS. 6A and 6B shows a synthesis scheme and NMR spectrum, respectively for nucleobase JB1b.

Figure 7A:
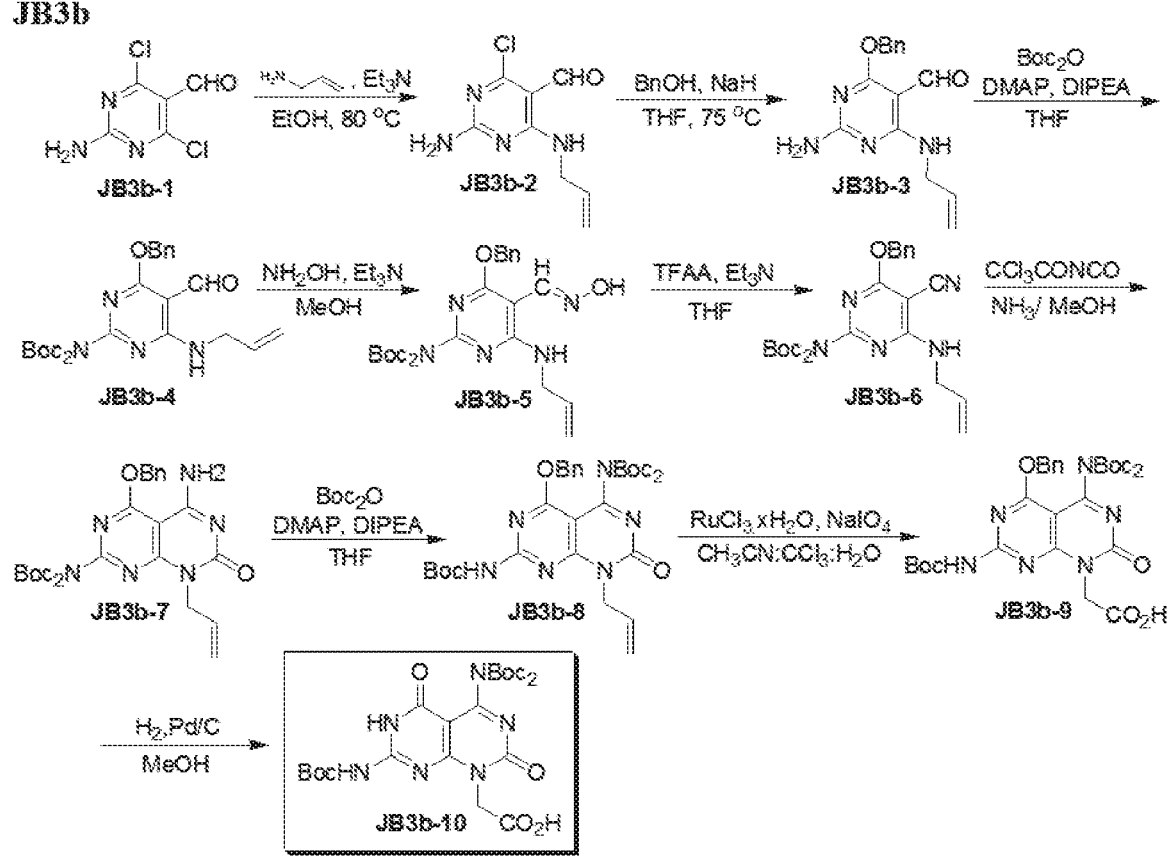
FIG. 7A shows the synthesis scheme for compound JB3b.
Figure 7B:
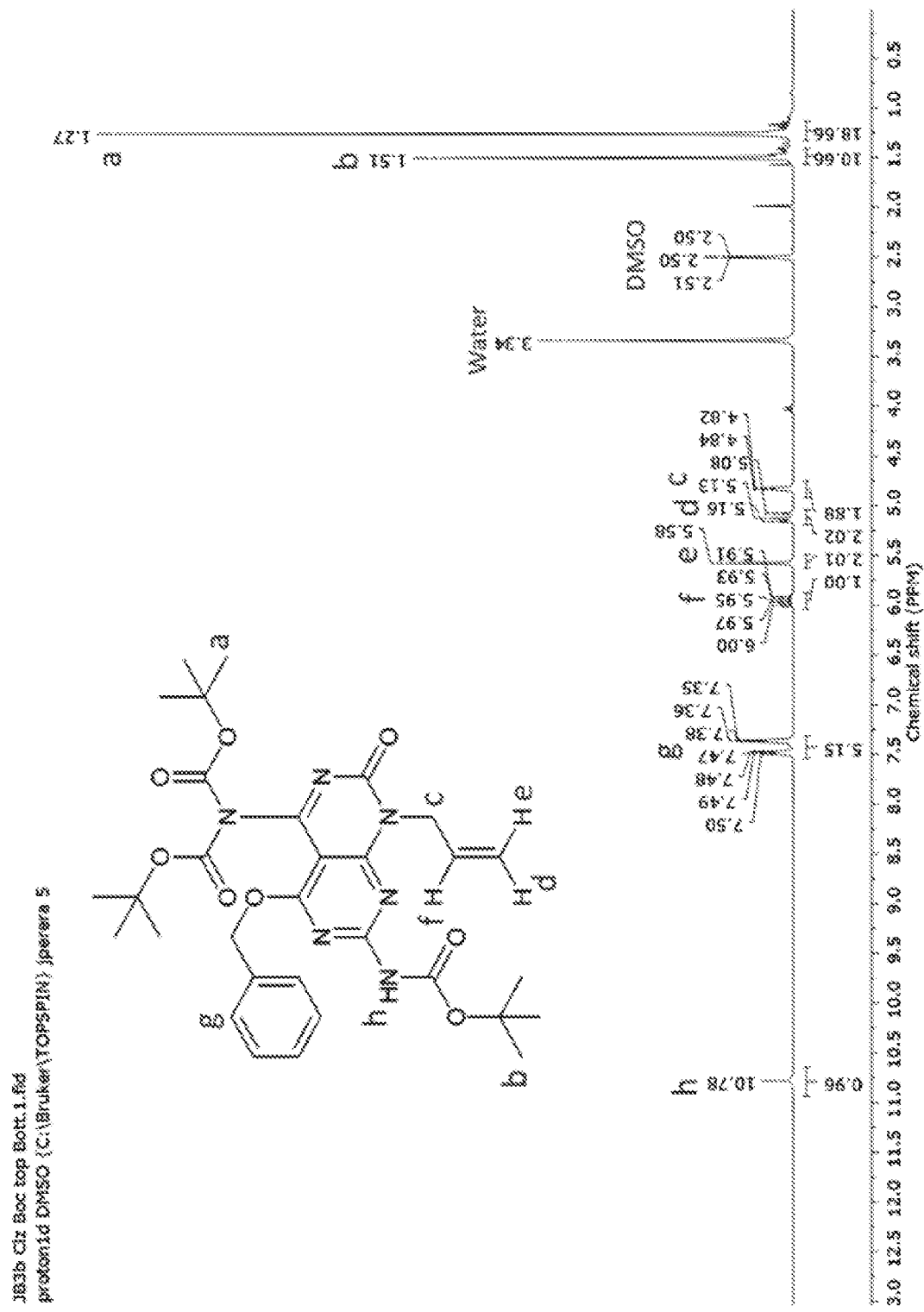
FIG. 7B provides an NMR spectrum of the JB3b-8 product.

FIGS. 7A and 7B shows a synthesis scheme and NMR spectrum, respectively for nucleobase JB3b.

Figure 8A:
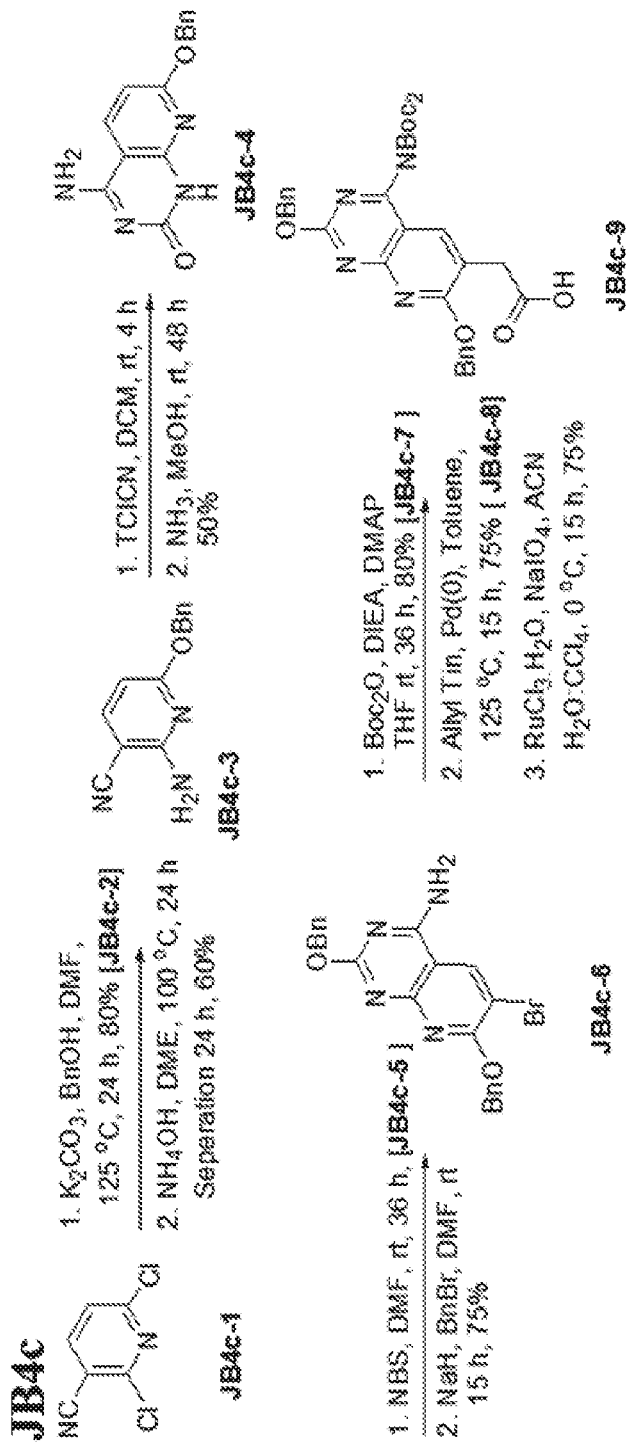
FIG. 8A shows the synthesis scheme for compound JB4c.
Figure 8B:
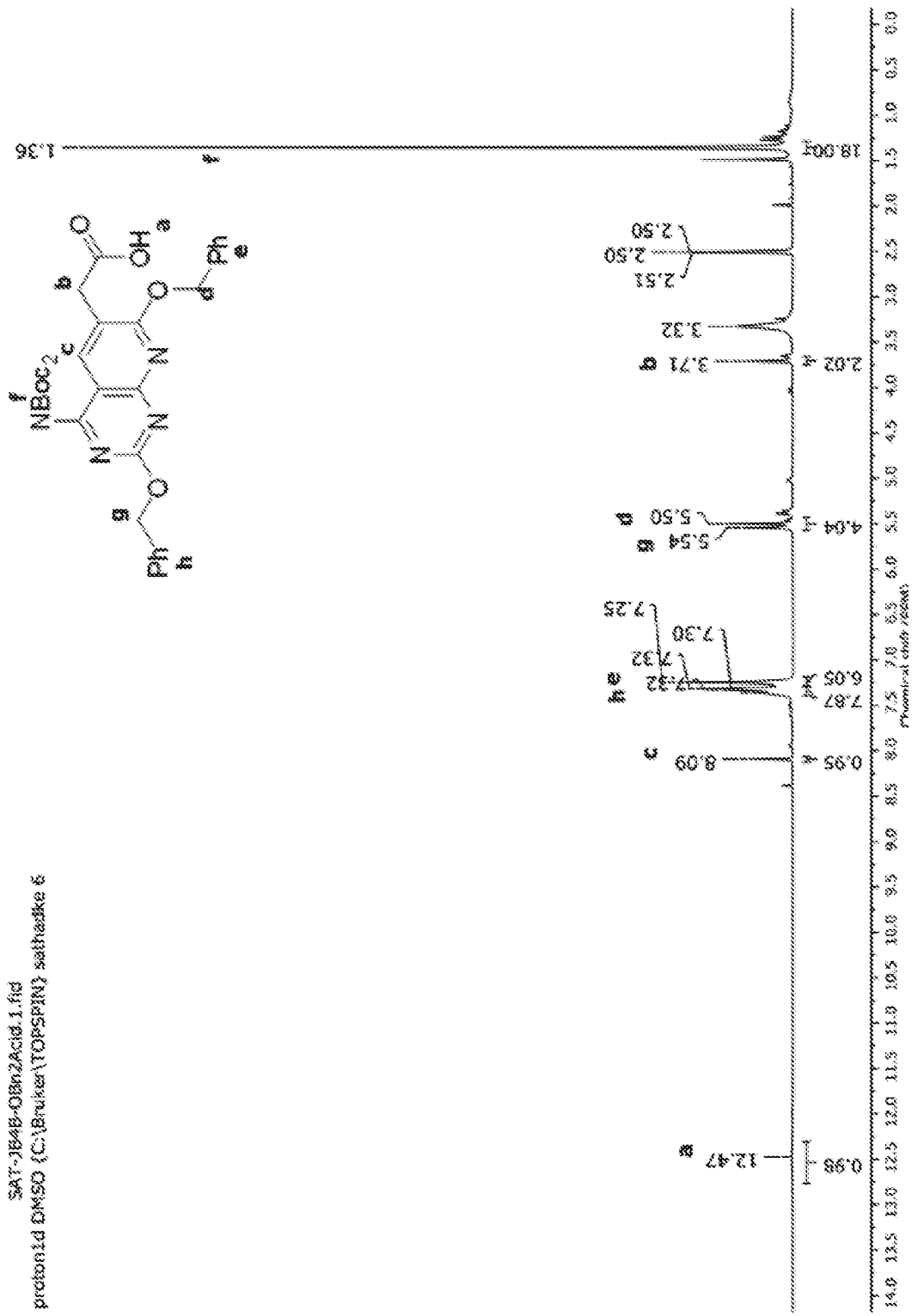
FIG. 8B provides an NMR spectrum of the JB4c-9 product.

FIGS. 8A and 8B shows a synthesis scheme and spectrum, respectively for nucleobase JB4c.

The following numbered clauses are illustrative of various aspects of the invention.
1. A genetic recognition reagent comprising a plurality of nucleobase moieties attached to a nucleic acid or nucleic acid analog backbone, in which at least one nucleobase moiety is chosen from:

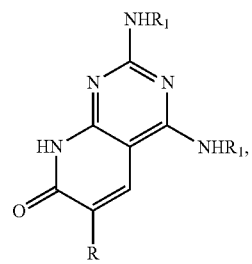

JB1b

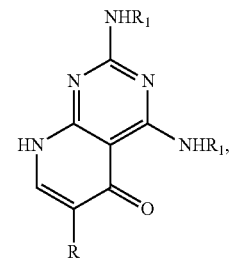

JB1c

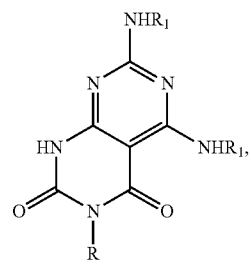

JB1d

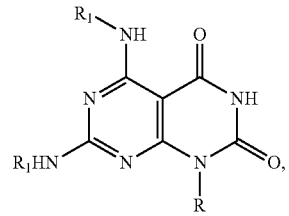

JB2b

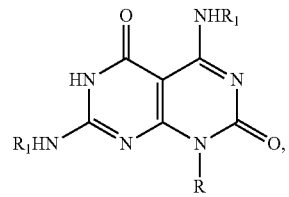

JB3b

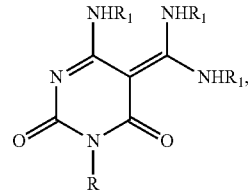

JB4b

-continued
JB4c
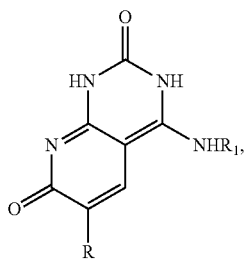
JB4d
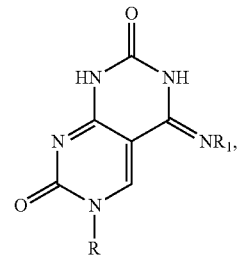
JB4e
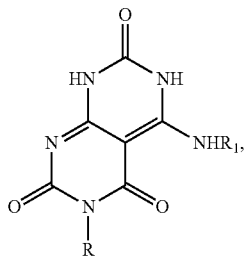
JB5b
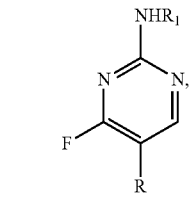
JB5c
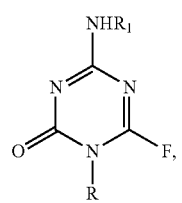
JB5d
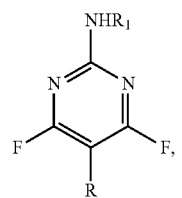
JB6b
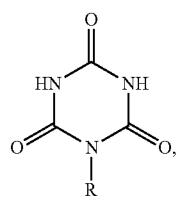
-continued
JB7e
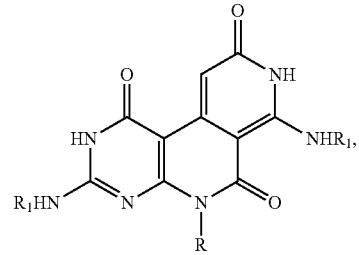
JB7f
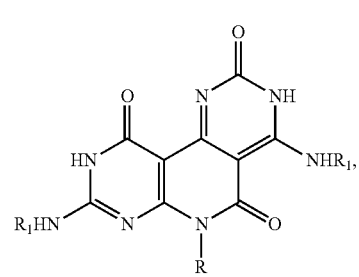
JB8b
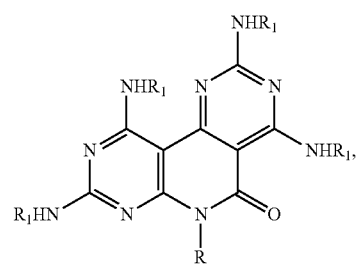
JB9c
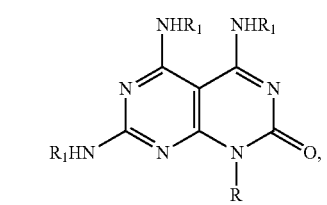
JB10b
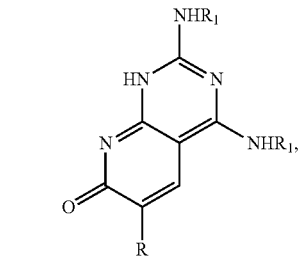
JB10c
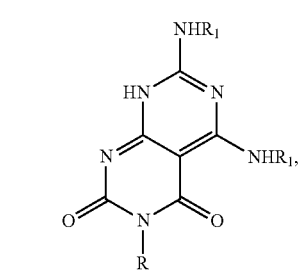

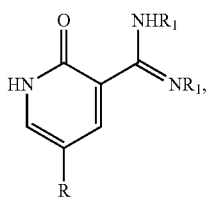 JB11b

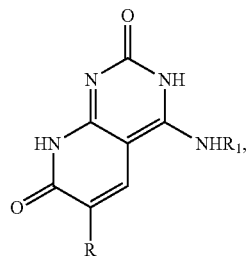 JB11c

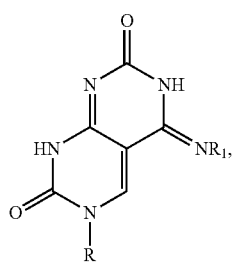 JB11d

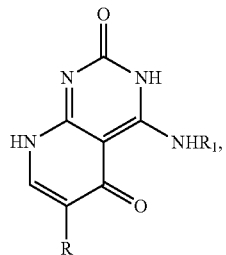 JB11e

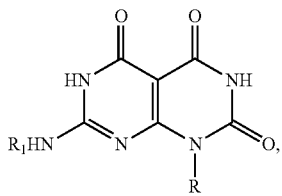 JB12b

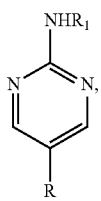 JB13b

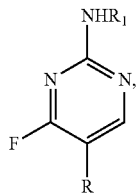 JB13c

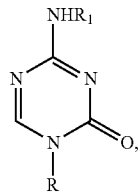 JB13d

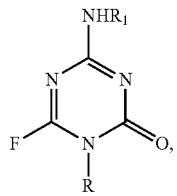 JB13e

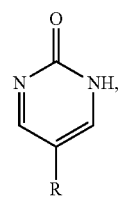 JB13f

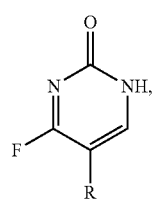 JB13g

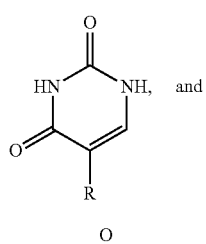 JB13h and JB13i wherein R1 is H or a protecting group, and R is a residue of a nucleic acid or nucleic acid analog backbone monomer in the genetic recognition reagent.

2. The genetic recognition reagent of clause 1, in which one or more instances of R1 is a protecting group, optionally chosen from: methyl, formyl, ethyl, acetyl, anisyl, benzyl, benzoyl, carbamate, trifluoroacetyl, diphenylmethyl, triphenylmethyl, N-hydroxysuccinimide, benzyloxymethyl, benzyloxycarbonyl, 2-nitrobenzoyl, t-Boc (tert-butyloxycarbonyl), 4-methylbenzyl, 4-nitrophenyl, 2-chlorobenzyloxycarbonyl, 2-bromobenzyloxycarbonyl, 2,4,5-trichlorophenyl, thioanizyl, thiocresyl, cbz (carbobenzyloxy), p-methoxybenzyl carbonyl, 9-fluorenylmethyloxycarbonyl, pentafluorophenyl, p-methoxybenzyl, 3,4-dimethozybenzyl, p-methoxyphenyl, 4-toluenesulfonyl, p-nitrobenzenesulfonates, 9-fluorenylmethyloxycarbonyl, 2-nitrophenylsulfenyl, 2,2,5,7,8-pentamethyl-chroman-6-sulfonyl, and p-bromobenzenesulfonyl.

3. The genetic recognition reagent of clause 1, in which the backbone is chosen from one of a DNA, RNA, peptide nucleic acid (PNA), phosphorothioate, locked nucleic acid, unlocked nucleic acid, 2'-O-methyl-substituted RNA, morpholino nucleic acid, threose nucleic acid, or glycol nucleic acid backbone, or any combination thereof.

4. The genetic recognition reagent of clause 1, in which the backbone is a peptide nucleic acid (PNA) backbone.

5. The genetic recognition reagent of clause 1, in which the backbone is a gamma peptide nucleic acid (γPNA) backbone.

6. The genetic recognition reagent of clause 5, in which the backbone is PEGylated, with one or more PEG moieties of two to fifty (—O—CH$_2$—CH$_2$—) residues.

7. The genetic recognition reagent of clause 1, in which the backbone is a γPNA backbone in which R is

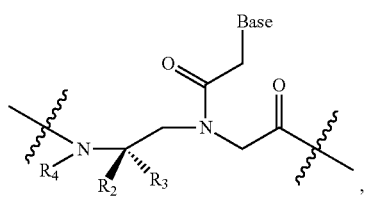

where R2, R3 and R4 are, independently, H, amino acid side chains, linear or branched (C$_1$-C$_8$)alkyl, (C$_2$-C$_8$)alkenyl, (C$_2$-C$_8$)alkynyl, (C$_1$-C$_6$)hydroxyalkyl, (C$_3$-C$_8$)aryl, (C$_3$-C$_8$)cycloalkyl, (C$_3$-C$_8$)aryl(C$_1$-C$_6$)alkylene, (C$_3$-C$_8$)cycloalkyl (C$_1$-C$_6$)alkylene, PEGylated moieties of the preceding comprising from 1 to 50 (—O—CH$_2$—CH$_2$—) residues, —CH$_2$—(OCH$_2$—CH$_2$)$_q$OP$_1$, —CH$_2$—(OCH$_2$—CH$_2$)$_q$—NHP$_1$, —CH$_2$—(OCH$_2$—CH$_2$—O)$_q$—SP$_1$ and —CH$_2$—(SCH$_2$—CH$_2$)$_q$—SP$_1$, —CH$_2$—(OCH$_2$—CH$_2$)$_r$—OH, —CH$_2$—(OCH$_2$—CH$_2$)$_r$—NH$_2$, —CH$_2$—(OCH$_2$—CH$_2$) NHC(NH)NH$_2$, or —CH$_2$—(OCH$_2$—CH$_2$)$_r$—S—S [CH$_2$CH$_2$]$_s$NHC(NH)NH$_2$, where P$_1$ is selected from the group consisting of H, (C$_1$-C$_8$)alkyl, (C$_2$-C$_8$)alkenyl, (C$_2$-C$_8$)alkynyl, (C$_3$-C$_8$)aryl, (C$_3$-C$_8$)cycloalkyl, (C$_3$-C$_8$)aryl (C$_1$-C$_6$)alkylene and (C$_3$-C$_8$)cycloalkyl(C$_1$-C$_6$)alkylene; q is an integer from 0 to 10, inclusive; r and s are each independently integers from 1 to 50, inclusive; where R2 and R3 are different and one of R2 or R3 is H, and wherein Base is the nucleobase moiety.

8. The genetic recognition reagent of clause 7, in which R3 is H, R2 is an amino acid side chain that is optionally PEGylated, with one or more PEG moieties of one to twelve (—O—CH$_2$—CH$_2$—) residues.

9. The genetic recognition reagent of clause 1, in which the nucleobases are arranged in a sequence complementary to a target sequence of a nucleic acid.

10. The genetic recognition reagent of clause 1, having from 3 to 25 nucleobases.

11. The genetic recognition reagent of clause 1, having the structure:

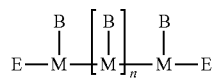

where each instance of M is a backbone monomer residue and each instance of B is a nucleobase moiety, where at least one instance of B is the divalent nucleobase moiety, E are independently end groups, and optionally "n" is zero or a positive integer ranging from 1 to 48.

12. The genetic recognition reagent of any one of clauses 1-12, in which all instances of R1 are H.

13. The genetic recognition reagent of any one of clauses 1-12, comprising a divalent nucleobase chosen from JB1b, JB1c, and JB1d.

14. The genetic recognition reagent of any one of clauses 1-12, comprising the nucleobase JB2b.

15. The genetic recognition reagent of any one of clauses 1-12, comprising the nucleobase JB3b.

16. The genetic recognition reagent of any one of clauses 1-12, comprising a divalent nucleobase chosen from JB4b, JB4c, JB4d, and JB4e.

17. The genetic recognition reagent of any one of clauses 1-12, comprising a divalent nucleobase chosen from JB5b, JB5c, and JB5d.

18. The genetic recognition reagent of any one of clauses 1-12, comprising the nucleobase JB6b.

19. The genetic recognition reagent of any one of clauses 1-12, comprising a divalent nucleobase chosen from JB7e and JB7f.

20. The genetic recognition reagent of any one of clauses 1-12, comprising the nucleobase JB8b.

21. The genetic recognition reagent of any one of clauses 1-12, comprising the nucleobase JB9c.

22. The genetic recognition reagent of any one of clauses 1-12, comprising a divalent nucleobase chosen from JB10b and JB10c.

23. The genetic recognition reagent of any one of clauses 1-12, comprising a divalent nucleobase chosen from JB11b, JB11c, JB11d, and JB11e.

24. The genetic recognition reagent of any one of clauses 1-12, comprising the nucleobase JB12b.

25. The genetic recognition reagent of any one of clauses 1-12, comprising a divalent nucleobase chosen from JB13b, JB13c, JB13d, JB13e, JB13f, JB13g, JB13h, and JB13i.

26. The genetic recognition reagent of any one of clauses 1-12, comprising a divalent nucleobase chosen from JB1b, JB1c, JB1d, JB2b, JB3b, B4b, JB4c, JB4d, and JB4e.

27. A compound having a structure:

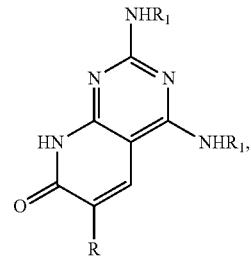

JB1b

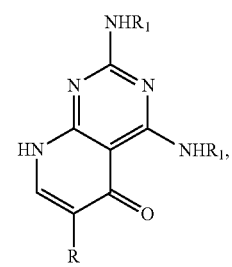

JB1c

-continued
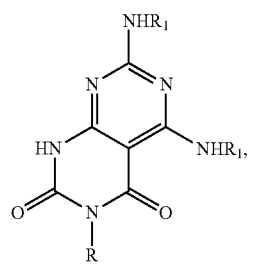
JB1d
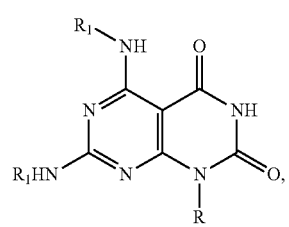
JB2b
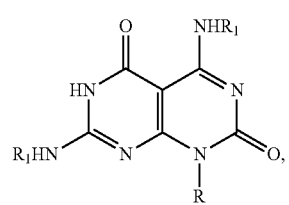
JB3b
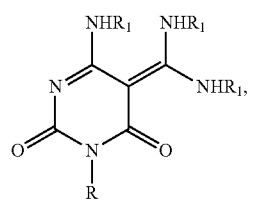
JB4b
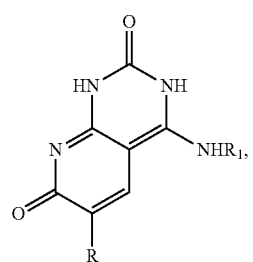
JB4c
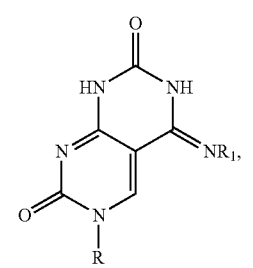
JB4d
-continued
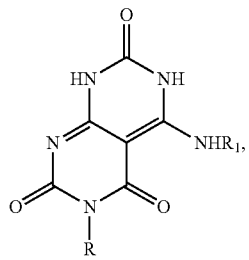
JB4e
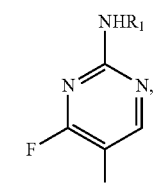
JB5b
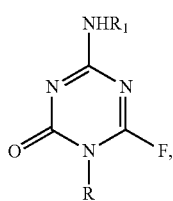
JB5c
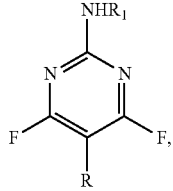
JB5d
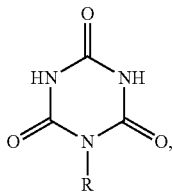
JB6b
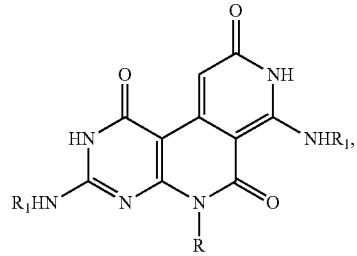
JB7e
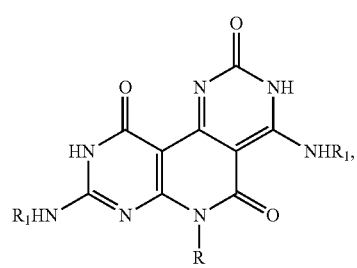
JB7f JB8b
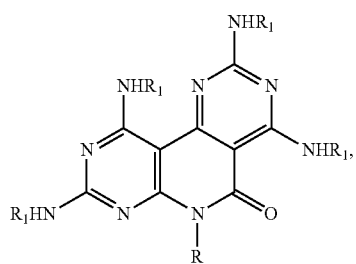
JB9c
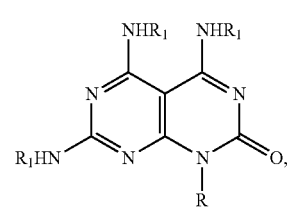
JB10b
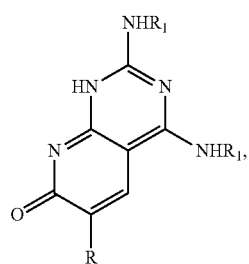
JB10c
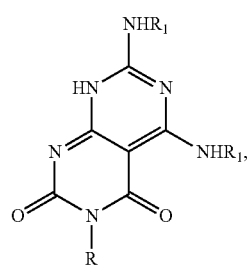
JB11b
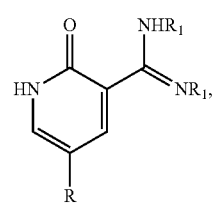
JB11c
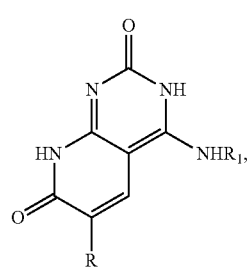
JB11d
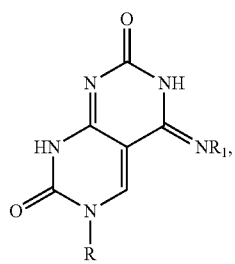
JB11e
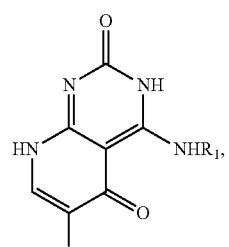
JB12b
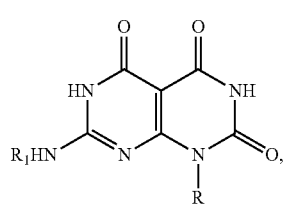
JB13b
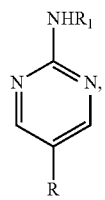
JB13c
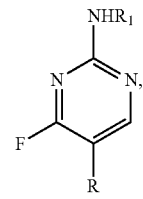
JB13d
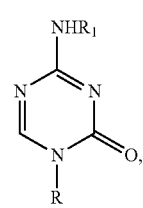
JB13e
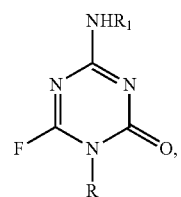

-continued

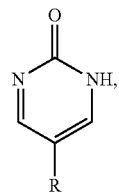
JB13f

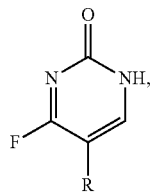
JB13g

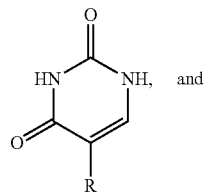
JB13h

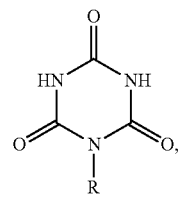
JB13i

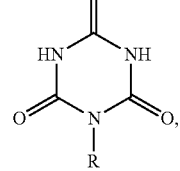

wherein R1 is H or a protecting group, and R is: H; a protecting group; a reactive group; a solid substrate; or a nucleic acid or nucleic acid analog backbone monomer or a residue thereof in a nucleic acid or nucleic acid analog polymer.

28. The compound of clause 27, wherein R is a reactive group, such as carboxyl, hydroxyl, amine, cyanate, thiol, epoxide, vinyl, allyl, n-hydroxysuccinimide (NHS) ester, azide, alkynyl, maleimide, hydrazide, tetrazine, phosphoramidite, cycloalkyne, nitrile, or $(CH_2)_nCO_2H$ or $(CH_2)_nCO_2Y$ where n=1-5 and Y=a leaving group.

29. The compound of clause 27, wherein R is a nucleic acid or nucleic acid analog backbone monomer.

30. The compound of clause 27, wherein R is a residue of a nucleic acid or nucleic acid analog backbone monomer in a nucleic acid or nucleic acid analog polymer.

31. The compound of clause 27, wherein R is a solid substrate, such as a silicon wafer, a multi-well dish, or a polymeric bead, and optionally an array.

32. The compound of any one of clauses 27-31, chosen from JB1b, JB1c, and JB1d.

33. The compound of any one of clauses 27-31, having the structure of JB2b.

34. The compound of any one of clauses 27-31, having the structure of JB3b.

35. The compound of any one of clauses 27-31, chosen from JB4b, JB4c, JB4d, and JB4e.

36. The compound of any one of clauses 27-31, chosen from JB5b, JB5c, and JB5d.

37. The compound of any one of clauses 27-31, having the structure of JB6b.

38. The compound of any one of clauses 27-31, chosen from JB7e and JB7f.

39. The compound of any one of clauses 27-31, having the structure of JB8b.

40. The compound of any one of clauses 27-31, having the structure of JB9c.

41. The compound of any one of clauses 27-31, chosen from JB10b and JB10c.

42. The compound of any one of clauses 27-31, chosen from JB11b, JB11c, JB11d, and JB11e.

43. The compound of any one of clauses 27-31, having the structure of JB12b.

44. The compound of any one of clauses 27-31, chosen from JB13b, JB13c, JB13d, JB13e, JB13f, JB13g, JB13h, and JB13i.

45. The compound of any one of clause 27-31, chosen from JB1b, JB1c, JB1d, JB2b, JB3b, B4b, JB4c, JB4d, and JB4e.

46. The compound of any one of clauses 27-45, wherein R1 is a protecting group.

47. The compound of clause 46, wherein the protecting group is chosen from one or more of: methyl, formyl, ethyl, acetyl, anisyl, benzyl, benzoyl, carbamate, trifluoroacetyl, diphenylmethyl, triphenylmethyl, N-hydroxysuccinimide, benzyloxymethyl, benzyloxycarbonyl, 2-nitrobenzoyl, t-Boc (tert-butyloxycarbonyl), 4-methylbenzyl, 4-nitrophenyl, 2-chlorobenzyloxycarbonyl, 2-bromobenzyloxycarbonyl, 2,4,5-trichlorophenyl, thioanizyl, thiocresyl, cbz (carbobenzyloxy), p-methoxybenzyl carbonyl, 9-fluorenylmethyloxycarbonyl, pentafluorophenyl, p-methoxybenzyl, 3,4-dimethozybenzyl, p-methoxyphenyl, 4-toluenesulfonyl, p-nitrobenzenesulfonates, 9-fluorenylmethyloxycarbonyl, 2-nitrophenylsulfenyl, 2,2,5,7,8-pentamethyl-chroman-6-sulfonyl, and p-bromobenzenesulfonyl.

48. The compound of clause 27, wherein R is peptide nucleic acid backbone monomer or a residue thereof in a peptide nucleic acid polymer.

49. The compound of clause 48, wherein the peptide nucleic acid backbone monomer is a gamma peptide nucleic acid (γPNA) backbone monomer.

50. The compound of clause 48 or 49, wherein the peptide nucleic acid backbone backbone monomer is PEGylated, with one or more PEG moieties of from 2 to 50 ($-O-CH_2-CH_2-$) residues.

51. The compound of clause 49, wherein gamma peptide nucleic acid (γPNA) backbone monomer is

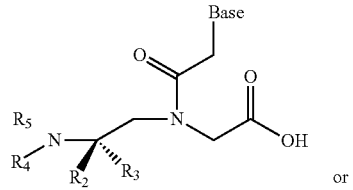

or

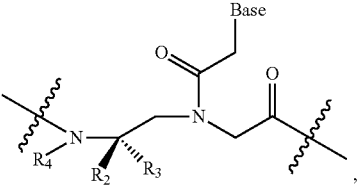

, where R2, R3 and R4 are, independently, H, amino acid side chains, linear or branched $(C_1-C_8)$alkyl, $(C_2-C_8)$alkenyl, $(C_2-C_8)$alkynyl, $(C_1-C_8)$hydroxyalkyl, $(C_3-C_8)$aryl, $(C_3-C_8)$cycloalkyl, $(C_3-C_8)$aryl$(C_1-C_6)$alkylene, $(C_3-C_8)$cycloalkyl $(C_1-C_6)$alkylene, PEGylated moieties of the preceding comprising from 1 to 50 ($-O-CH_2-CH_2-$) residues, —CH$_2$—(OCH$_2$—CH$_2$)$_q$OP$_1$, —CH$_2$—(OCH$_2$—CH$_2$)$_q$—NHP$_1$, —CH$_2$—(OCH$_2$—CH$_2$-0)$_q$—SP$_1$, and —CH$_2$—(SCH$_2$—CH$_2$)$_q$—SP$_1$, —CH$_2$—(OCH$_2$—CH$_2$)$_r$—OH, —CH$_2$—(OCH$_2$—CH$_2$)$_r$—NH$_2$, —CH$_2$—(OCH$_2$—CH$_2$)$_r$—NHC(NH)NH$_2$, or —CH$_2$—(OCH$_2$—CH$_2$)$_r$—S—S[CH$_2$CH$_2$]$_s$NHC(NH)NH$_2$, where P$_1$ is selected from the group consisting of H, (C$_1$-C$_8$)alkyl, (C$_2$-C$_8$)alkenyl, (C$_2$-C$_8$)alkynyl, (C$_3$-C$_8$)aryl, (C$_3$-C$_8$)cycloalkyl, (C$_3$-C$_8$)aryl(C$_1$-C$_6$)alkylene and (C$_3$-C$_8$)cycloalkyl(C$_1$-C$_6$)alkylene; q is an integer from 0 to 10, inclusive; r and s are each independently integers from 1 to 50, inclusive; where R2 and R3 are different and one of R2 or R3 is H, R5 is H or a protecting group, and wherein Base is the nucleobase moiety.

52. The compound of clause 27, wherein R is a nucleic acid analog backbone monomer chosen from: a phosphorothioate backbone monomer, a locked nucleic acid backbone monomer, an unlocked nucleic acid backbone monomer, a 2'-O-methyl-substituted RNA backbone monomer, a morpholino nucleic acid backbone monomer, a threose nucleic acid backbone monomer, or a glycol nucleic acid backbone monomer.

53. The compound of clause 27, wherein R is a ribose mono-, di-, or tri-phosphate or a deoxyribose mono-, di-, or tri-phosphate, such as a 5' monophosphate, diphosphate, or triphosphate of ribose or deoxyribose.

54. A kit comprising a compound of any one of clauses 27-53 in a vessel, wherein R is a nucleic acid or nucleic acid analog backbone monomer.

55. The kit of clause 54, further comprising monomers comprising at least one of each of a JB1-series nucleobase, a JB2-series nucleobase, a JB3-series nucleobase, and a JB4-series nucleobase, and optionally one or more, or optionally all, of a JB5-series nucleobase, a JB6-series nucleobase, a JB7-series nucleobase, a JB8-series nucleobase, a JB9-series nucleobase, a JB10-series nucleobase, a JB11-series nucleobase, a JB12-series nucleobase, a JB13-series nucleobase, JB14, JB15, and JB16, each in separate vessels.

56. An array comprising a genetic recognition reagent of any one of clauses 1-26.

57. A method of detection of a target sequence in a nucleic acid, comprising contacting a genetic recognition reagent of any one of clauses 1-26 with a sample comprising nucleic acid and detecting binding of the genetic recognition reagent with a nucleic acid.

58. A method of isolation and purification or a nucleic acid containing a target sequence, comprising, contacting a nucleic acid sample with a genetic recognition reagent of any of clauses 1-26, separating the nucleic acid sample from the genetic recognition reagent, leaving any nucleic acid bound to the genetic recognition reagent bound to the genetic recognition reagent, and separating the genetic recognition reagent from any nucleic acid bound to the genetic recognition reagent.

59. The method of clause 58, wherein the genetic recognition reagent is immobilized on a substrate, comprising contacting a nucleic acid with the substrate, washing the substrate to remove unbound nucleic acid from the substrate, but leaving bound nucleic acid bound to the substrate, and eluting the bound nucleic acid from the substrate.

60. A composition comprising a genetic recognition reagent or compound according to any one of clauses 1-53 and a pharmaceutically-acceptable excipient.

The present invention has been described with reference to certain exemplary embodiments, dispersible compositions and uses thereof. However, it will be recognized by those of ordinary skill in the art that various substitutions, modifications or combinations of any of the exemplary embodiments may be made without departing from the spirit and scope of the invention. Thus, the invention is not limited by the description of the exemplary embodiments, but rather by the appended claims as originally filed.

We claim:

1. A genetic recognition reagent comprising a plurality of nucleobase moieties attached to a nucleic acid backbone or a nucleic acid analog backbone, in which at least one of the plurality of nucleobase moieties is a ring system chosen from:

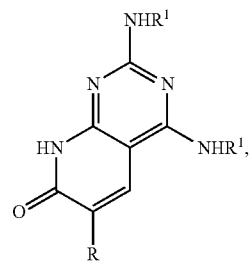

JB1b

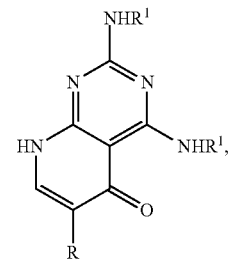

JB1c

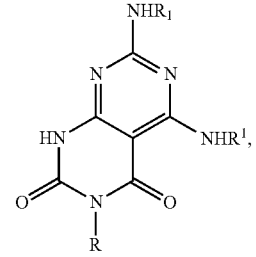

JB1d

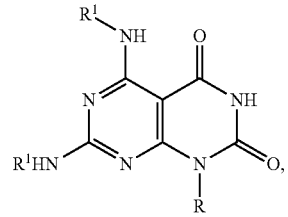

JB2b

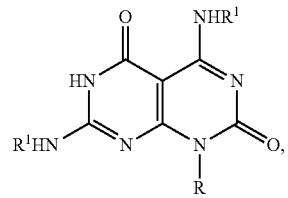

JB3b

JB4b 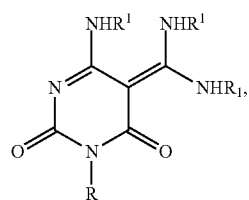
JB4c 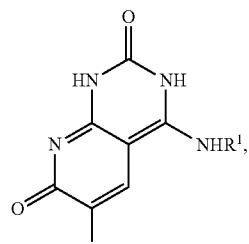
JB4d 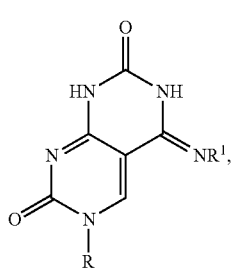
JB4e 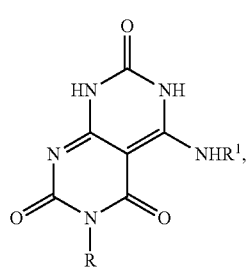
JB5b 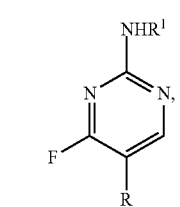
JB5c 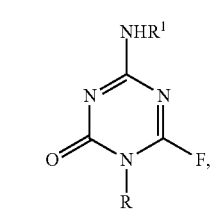
JB5d 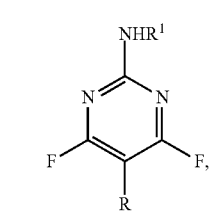
JB7e 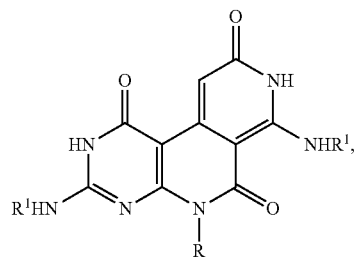
JB7f 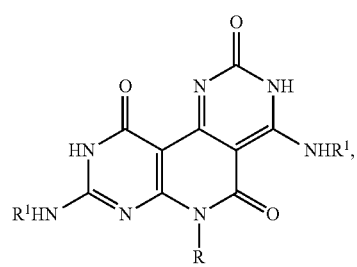
JB8b 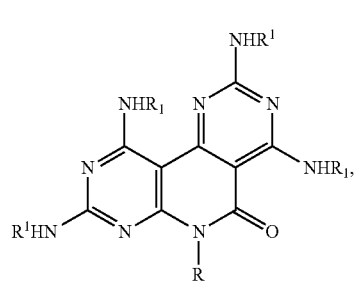
JB9c 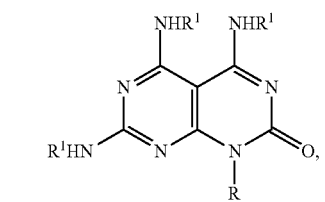
JB10b 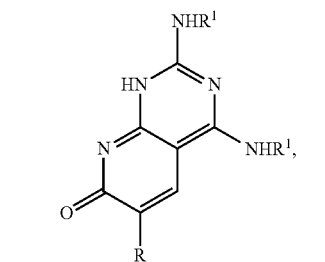
JB10c 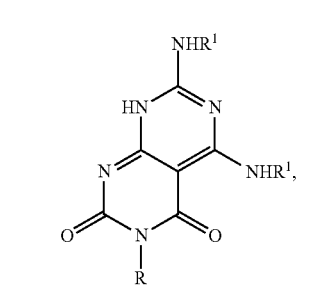

-continued

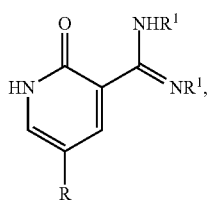
JB11b

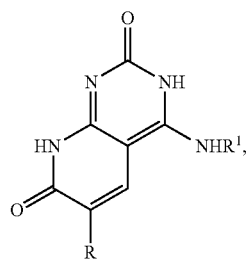
JB11c

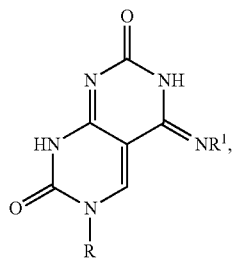
JB11d

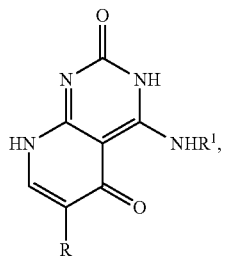
JB11e

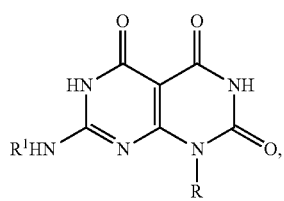
JB12b

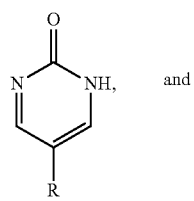
JB13f

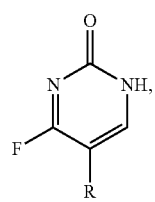
JB13g wherein $R^1$ is H or a protecting group, and R is a residue of the nucleic acid backbone or a residue of the nucleic acid analog backbone in the genetic recognition reagent.

2. The genetic recognition reagent of claim 1, in which $R^1$ is the protecting group, wherein the protecting group is independently: methyl, formyl, ethyl, acetyl, anisyl, benzyl, benzoyl, carbamate, trifluoroacetyl, diphenylmethyl, triphenylmethyl, benzyloxymethyl, benzyloxycarbonyl, 2-nitrobenzoyl, t-Boc (tert-butyloxycarbonyl), 4-methylbenzyl, 4-nitrophenyl, 2-chlorobenzyloxycarbonyl, 2-bromobenzyloxycarbonyl, 2,4,5-trichlorophenyl, thioanizyl, thiocresyl, cbz (carbobenzyloxy), p-methoxybenzyl carbonyl, 9-fluorenylmethyloxycarbonyl, pentafluorophenyl, p-methoxybenzyl, 3,4-dimethozybenzyl, p-methoxyphenyl, 4-toluenesulfonyl, p-nitrobenzenesulfonyl, 9-fluorenylmethyloxycarbonyl, 2-nitrophenylsulfenyl, 2,2,5,7,8-pentamethyl-chroman-6-sulfonyl, or p-bromobenzenesulfonyl.

3. The genetic recognition reagent of claim 1, in which the nucleic acid backbone or the nucleic acid analog backbone is a DNA backbone, RNA backbone, peptide nucleic acid (PNA) backbone, phosphorothioate backbone, locked nucleic acid backbone, unlocked nucleic acid backbone, 2'—O-methyl—substituted RNA backbone, morpholino nucleic acid backbone, threose nucleic acid backbone, or glycol nucleic acid backbone, or any combination thereof.

4. The genetic recognition reagent of claim 1, in which the nucleic acid analog backbone is a peptide nucleic acid (PNA) backbone.

5. The genetic recognition reagent of claim 1, having a structure:

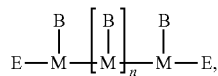

where each instance of M is the residue of the nucleic acid backbone or the residue of the nucleic acid analog backbone, and each instance of B is independently one of the plurality of nucleobase moieties, where at least one instance of B is the ring system, each instance of E is independently an end group, and "n" is zero or a positive integer ranging from 1 to 48.

6. The genetic recognition reagent of claim 1, in which all instances of $R^1$ are H.

7. A compound comprising a nucleobase moiety and R, wherein the compound is:

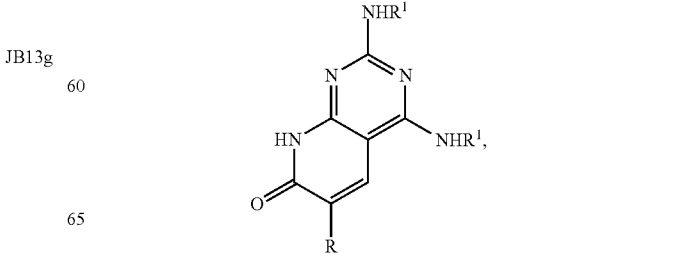
JB1b

-continued
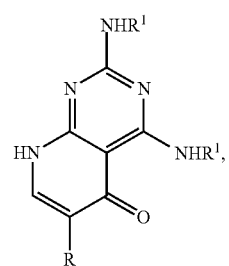
JB1c
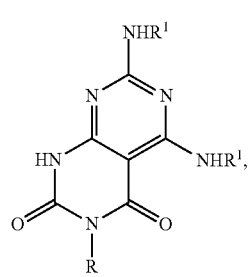
JB1d
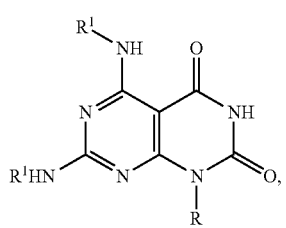
JB2b
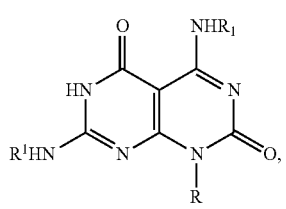
JB3b
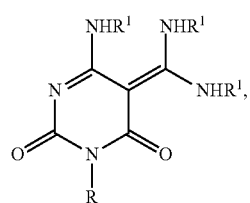
JB4b
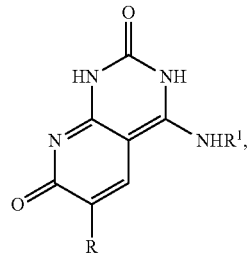
JB4c
-continued
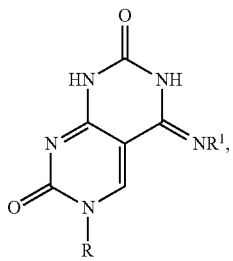
JB4d
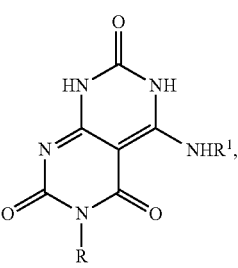
JB4e
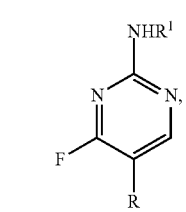
JB5b
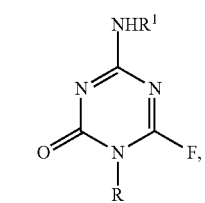
JB5c
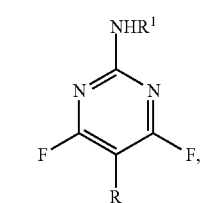
JB5d
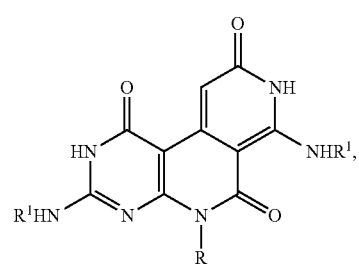
JB7e -continued JB7f
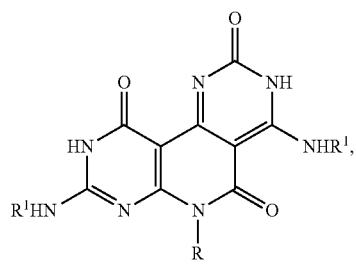

JB8b
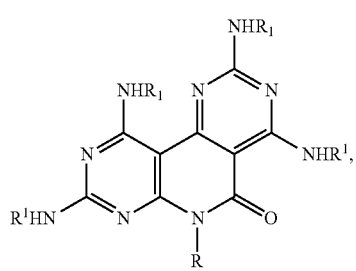

JB9c
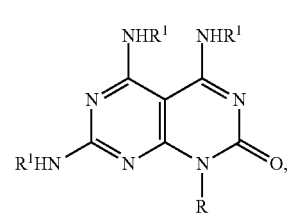

JB10b
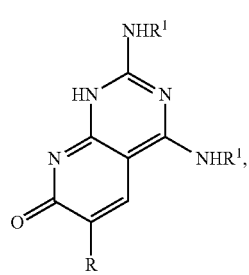

JB10c
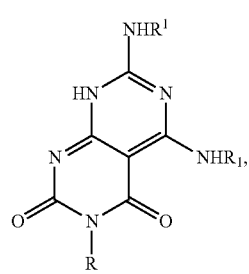

JB11b
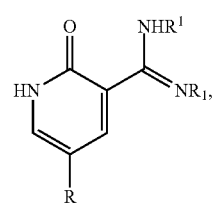

-continued

JB11c
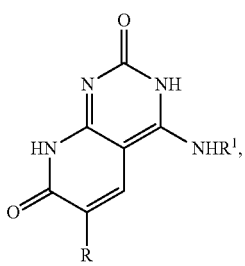

JB11d
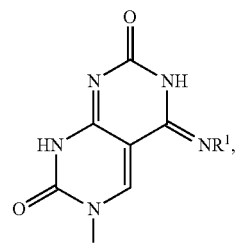

JB11e
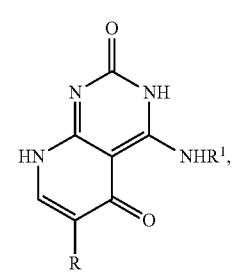

JB12b
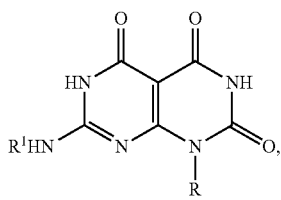

JB13f
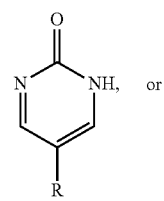

JB13g
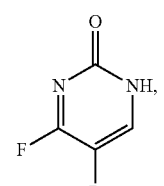

wherein $R^1$ is H or a protecting group, and R is: carboxyl, hydroxyl, amine, cyanate, thiol, epoxide, vinyl, N-hydroxysuccinimide (NHS) ester, azide, alkynyl, maleimide, hydrazide, tetrazine, phosphoramidite, cycloalkyne, nitrile, $(CH_2)nCO_2H$ or $(CH_2)nCO_2Y$ where n=1-5 and Y=succinimidyl; a solid substrate; a nucleic acid backbone monomer; a nucleic acid analog backbone monomer; a residue of a nucleic acid polymer; or a residue of a nucleic acid analog polymer.

8. The compound of claim 7, wherein R is the nucleic acid backbone monomer or the nucleic acid analog backbone monomer.

9. The compound of claim 7, wherein R is the solid substrate, wherein the solid substrate is a silicon wafer, a multi-well dish, a polymeric bead, or an array.

10. The compound of claim 7, wherein each $R^1$ is the protecting group, wherein the protecting group is independently methyl, formyl, ethyl, acetyl, anisyl, benzyl, benzoyl, carbamate, trifluoroacetyl, diphenylmethyl, triphenylmethyl, benzyloxymethyl, benzyloxycarbonyl, 2-nitrobenzoyl, t-Boc (tert-butyloxycarbonyl), 4-methylbenzyl, 4-nitrophenyl, 2-chlorobenzyloxycarbonyl, 2-bromobenzyloxycarbonyl, 2,4,5-trichlorophenyl, thioanizyl, thiocresyl, cbz (carbobenzyloxy), p-methoxybenzyl carbonyl, 9-fluorenylmethyloxycarbonyl, pentafluorophenyl, p-methoxybenzyl, 3,4-dimethozybenzyl, p-methoxyphenyl, 4-toluenesulfonyl, p-nitrobenzenesulfonyl, 9-fluorenylmethyloxycarbonyl, 2-nitrophenylsulfenyl, 2,2,5,7,8-pentamethyl-chroman-6-sulfonyl, or p-bromobenzenesulfonyl.

11. The compound of claim 7, wherein R is the nucleic acid analog backbone monomer, wherein the nucleic acid analog backbone monomer is a peptide nucleic acid (PNA) backbone monomer.

12. The compound of claim 7, wherein R is the nucleic acid analog backbone monomer, and the nucleic acid analog backbone monomer is: a phosphorothioate backbone monomer, a locked nucleic acid backbone monomer, an unlocked nucleic acid backbone monomer, a 2'—O-methyl—substituted RNA backbone monomer, a morpholino nucleic acid backbone monomer, a threose nucleic acid backbone monomer, or a glycol nucleic acid backbone monomer.

13. The compound of claim 7, wherein R is the nucleic acid backbone monomer, wherein the nucleic acid backbone monomer is a ribose mono-, di-, or tri-phosphate, or a deoxyribose mono-, di-, or tri-phosphate.

14. A compound comprising a nucleobase moiety and R, wherein the compound is:

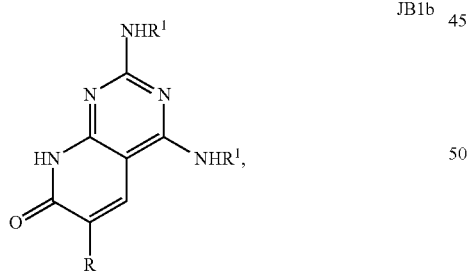
JB1b

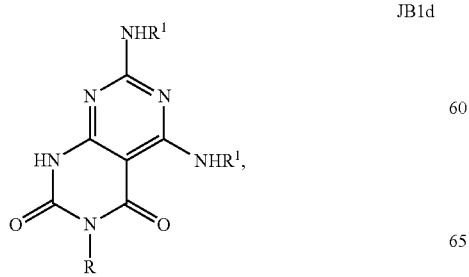
JB1d

-continued

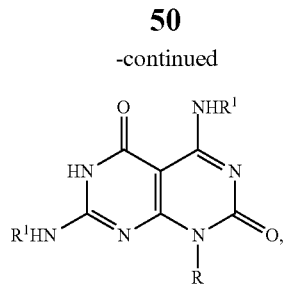
JB3b

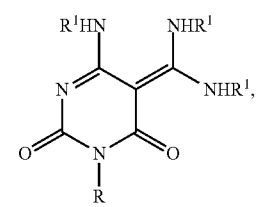
JB4b

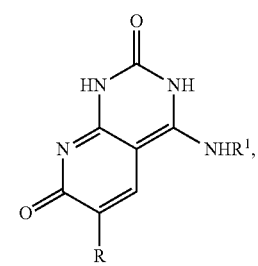
JB4c

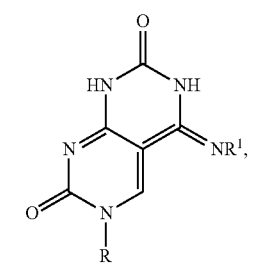
JB4d

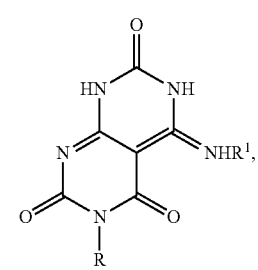
JB4e

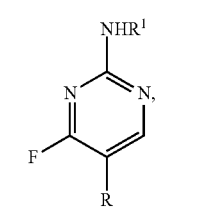
JB5b

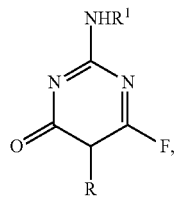
JB5c

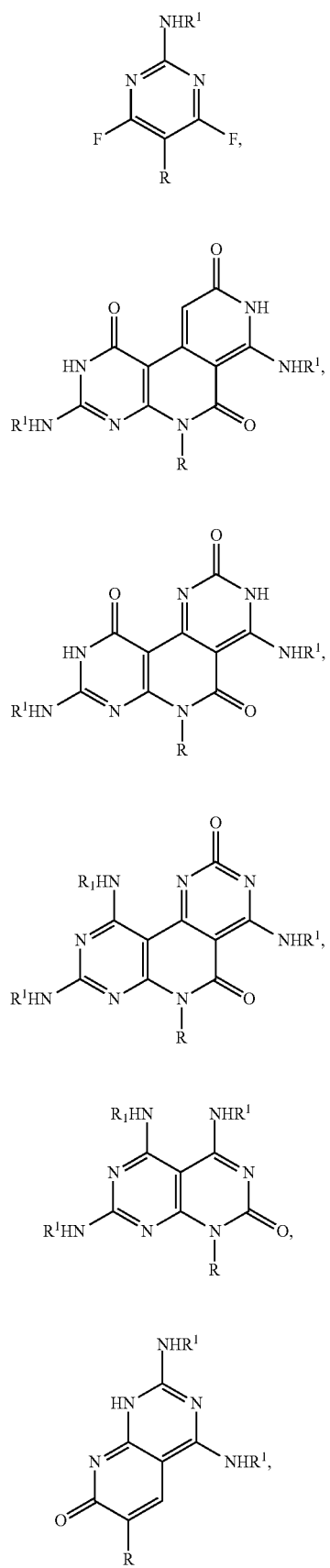
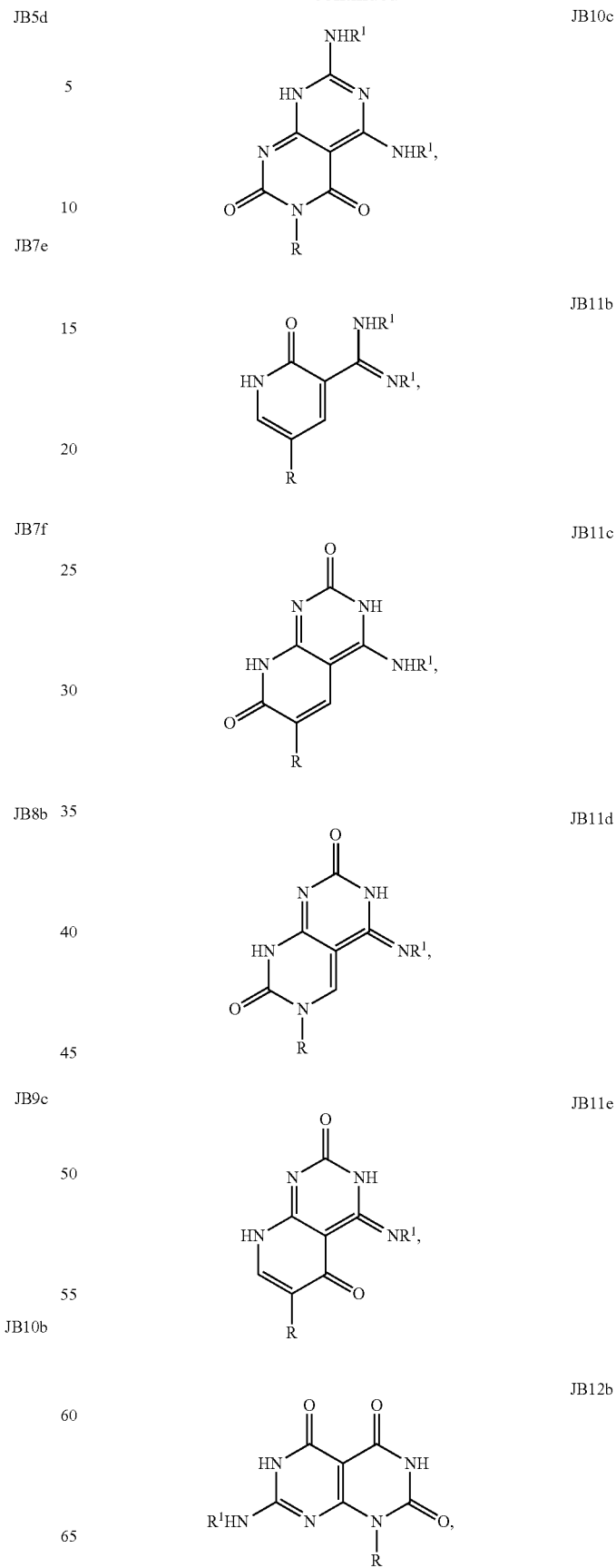

-continued

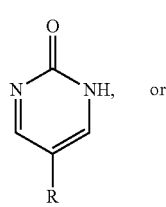
JB13f

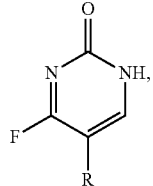
JB13g wherein $R^1$ is H or a protecting group, and R is: carboxyl, hydroxyl, amine, cyanate, thiol, epoxide, vinyl, allyl, N-hydroxysuccinimide (NHS) ester, azide, alkynyl, maleimide, hydrazide, tetrazine, phosphoramidite, cycloalkyne, nitrile, $(CH_2)_nCO_2H$ where n=1-5, a solid substrate, a nucleic acid backbone monomer, a nucleic acid analog backbone monomer, a residue of a nucleic acid polymer, or a residue of a nucleic acid analog polymer.

15. The genetic recognition reagent of claim 1, wherein the nucleic acid analog backbone is a peptide nucleic acid (PNA) backbone in which R and one nucleobase moiety of the plurality of nucleobase moieties form

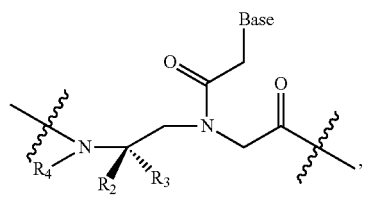

wherein:
each $R_2$, $R_3$ and $R_4$ is independently methyl, ethyl, amino acid side chains, linear or branched $(C_3-C_8)$alkyl, $(C_2-C_8)$alkenyl, $(C_2-C_8)$alkynyl, $(C_1-C_8)$hydroxyalkyl, $(C_3-C_8)$aryl, $(C_3-C_8)$cycloalkyl, $(C_3-C_8)$aryl$(C_1-C_6)$alkylene, $(C_3-C_8)$cycloalkyl$(C_1-C_6)$alkylene, a PEGylated moiety of the preceding comprising from 1 to 50 ($-O-CH_2-CH_2-$) residues, H, $-CH_2-(OCH_2-CH_2)_qOP_1$, $-CH_2-(OCH_2-CH_2)_q-NHP_1$, $-CH_2-(OCH_2-CH_2)_q-SP_1$ and $-CH_2-(SCH_2-CH_2)_q-SP_1$, $-CH_2-(OCH_2-CH_2)_r-OH$, $-CH_2-(OCH_2-CH_2)_r-NH_2$, $-CH_2-(OCH_2-CH_2)_r-NHC(NH)NH_2$, or $-CH_2-(OCH_2-CH_2)_r-S-S$ $[CH_2CH_2]_sNHC(NH)NH_2$, provided that $R_2$ and $R_3$ are different and one of $R_2$ or $R_3$ is H; or $R_3$ and $R_4$ together form a 1,3-propylene linkage and $R_2$ is H; or $R_2$ and $R_4$ together form a 1,3-propylene linkage and $R_3$ is H;
$P_1$ is selected from the group consisting of H, $(C_1-C_8)$alkyl, $(C_2-C_8)$alkenyl, $(C_2-C_8)$alkynyl, $(C_3-C_8)$aryl, $(C_3-C_8)$cycloalkyl, $(C_3-C_8)$aryl$(C_1-C_6)$alkylene and $(C_3-C_8)$cycloalkyl$(C_1-C_6)$alkylene;
q is an integer from 0 to 10, inclusive;
r and s are each independently integers from 1 to 50, inclusive; and
Base is the one nucleobase moiety of the plurality of nucleobase moieties.

16. The genetic recognition reagent of claim 15, in which $R_3$ is H, $R_2$ is an amino acid side chain that is PEGylated, with one or more PEG moieties of one to twelve ($-O-CH_2-CH_2-$) residues.

17. The compound of claim 11, wherein the PNA backbone monomer comprises a residue of the formula:

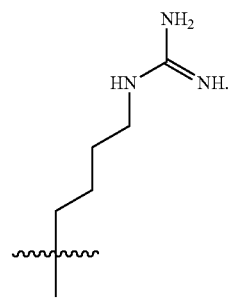 [SMILES: *CCCCNC(=N)N]

18. The compound of claim 11, wherein the PNA backbone monomer is a gamma peptide nucleic acid (γPNA) backbone monomer.

19. The compound of claim 11, wherein the PNA backbone monomer and the nucleobase moiety form

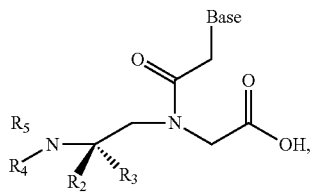

wherein each $R_2$, $R_3$ and $R_4$ is independently methyl, ethyl, amino acid side chains, linear or branched $(C_3-C_8)$alkyl, $(C_2-C_8)$alkenyl, $(C_2-C_8)$alkynyl, $(C_1-C_8)$hydroxyalkyl, $(C_3-C_8)$aryl, $(C_3-C_8)$cycloalkyl, $(C_3-C_8)$aryl$(C_1-C_6)$alkylene, $(C_3-C_8)$cycloalkyl$(C_1-C_6)$alkylene, a PEGylated moiety of the preceding comprising from 1 to 50 ($-O-CH_2-CH_2-$) residues, H, $-CH_2-(OCH_2-CH_2)_qOP_1$, $-CH_2-(OCH_2-CH_2)_q-NHP_1$, $-CH_2-(OCH_2-CH_2)_q-SP_1$ and $-CH_2-(SCH_2-CH_2)_q-SP_1$, $-CH_2-(OCH_2-CH_2)_r-OH$, $-CH_2-(OCH_2-CH_2)_r-NH_2$, $-CH_2-(OCH_2-CH_2)_r-NHC(NH)NH_2$, or $-CH_2-(OCH_2-CH_2)_r-S-S$ $[CH_2CH_2]_sNHC(NH)NH_2$, provided that $R_2$ and $R_3$ are different and one of $R_2$ or $R_3$ is H; or $R_3$ and $R_4$ together form a 1,3-propylene linkage and $R_2$ is H; or $R_2$ and $R_4$ together form a 1,3-propylene linkage and $R_3$ is H;
$R^5$ is a protecting group or H;
$P_1$ is selected from the group consisting of H, $(C_1-C_8)$alkyl, $(C_2-C_8)$alkenyl, $(C_2-C_8)$alkynyl, $(C_3-C_8)$aryl, $(C_3-C_8)$cycloalkyl, $(C_3-C_8)$aryl$(C_1-C_6)$alkylene and $(C_3-C_8)$cycloalkyl$(C_1-C_6)$alkylene;
q is an integer from 0 to 10, inclusive;
r and s are each independently integers from 1 to 50, inclusive; and
Base is the nucleobase moiety.

* * * * *

UNITED STATES PATENT AND TRADEMARK OFFICE
CERTIFICATE OF CORRECTION

PATENT NO. : 11,603,369 B2
APPLICATION NO. : 16/336210
DATED : March 14, 2023
INVENTOR(S) : Danith H. Ly et al.

Page 1 of 5

It is certified that error appears in the above-identified patent and that said Letters Patent is hereby corrected as shown below:

In the Claims

1. Column 41, Lines 3-9, Claim 1, delete " 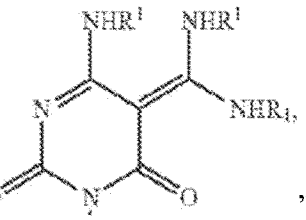 " and insert -- 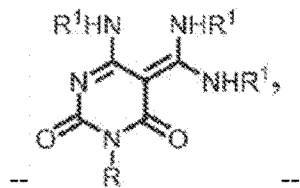 --

2. Column 42, Lines 25-34, Claim 1, delete " 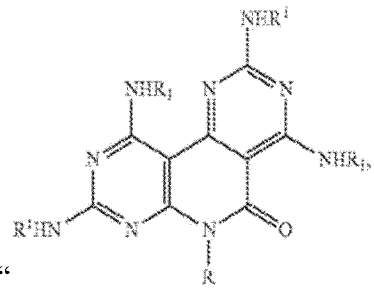 " and insert -- 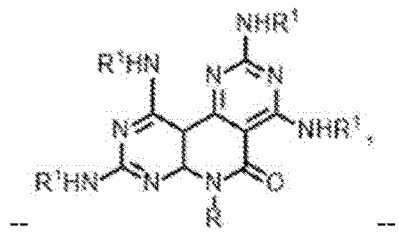 --

Signed and Sealed this
Third Day of October, 2023

Katherine Kelly Vidal
*Director of the United States Patent and Trademark Office*

CERTIFICATE OF CORRECTION (continued)
U.S. Pat. No. 11,603,369 B2

3. Column 44, Line 16, Claim 2, delete "3,4-dimethozybenzyl," and insert -- 3,4-dimethoxybenzyl, --

4. Column 45, Lines 37-44, Claim 7, delete " 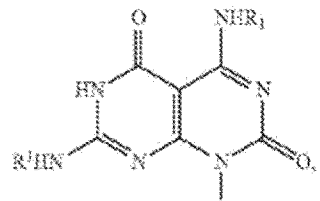 " and insert

-- 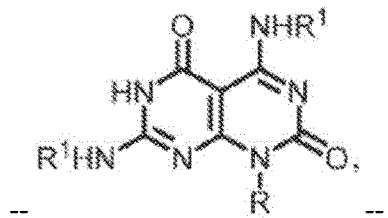 --

5. Column 47, Lines 14-24, Claim 7, delete " 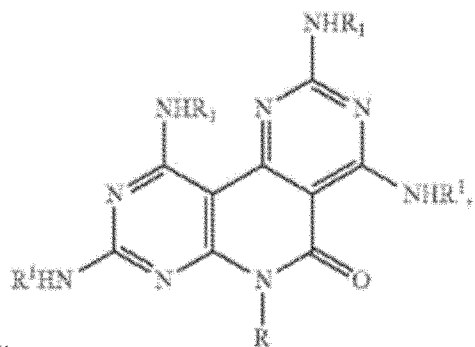 " and insert

-- 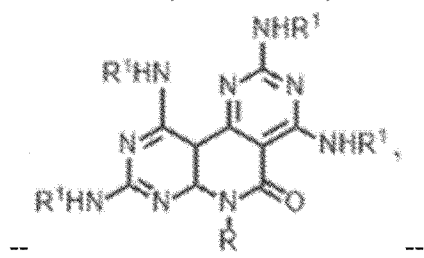 --

6. Column 47, Lines 47-57, Claim 7, delete " 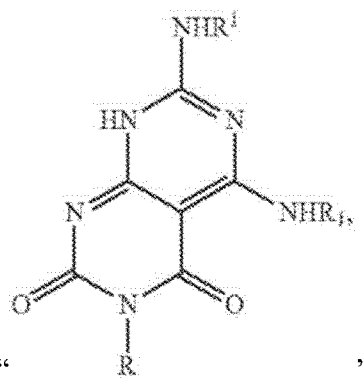 " and insert

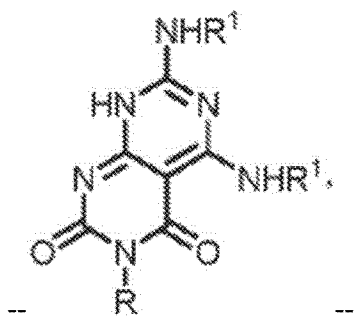
7. Column 47, Lines 59-66, Claim 7, delete " 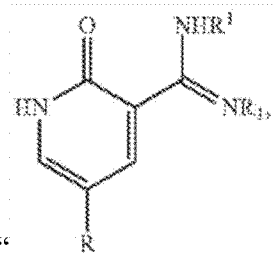 " and insert
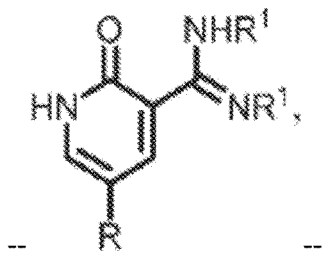
8. Column 49, Line 18, Claim 10, delete "3,4-dimethozybenzyl," and insert -- 3,4-dimethoxybenzyl, --
9. Column 50, Lines 30-38, Claim 14, delete " 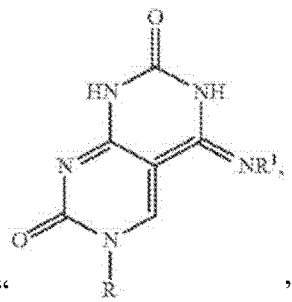 " and insert
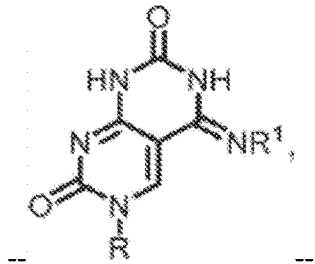

10. Column 50, Lines 41-49, Claim 14, delete " 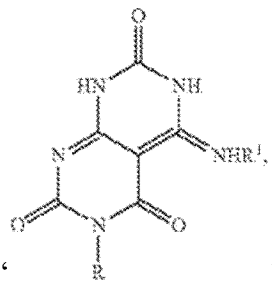 " and insert
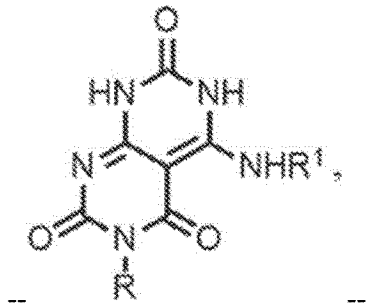
-- --
11. Column 52, Lines 36-45, Claim 14, delete " 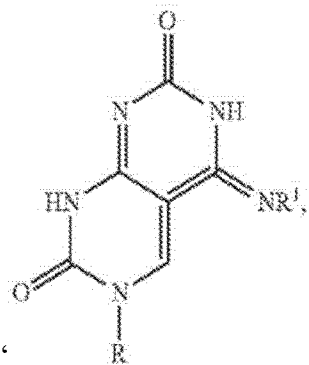 " and insert
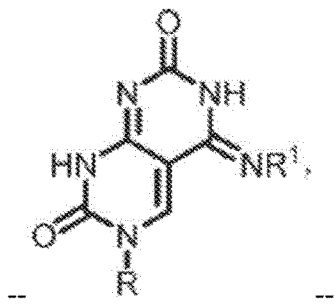
-- --
12. Column 52, Lines 47-57, Claim 14, delete " 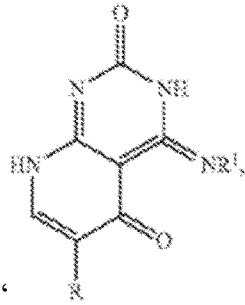 " and insert

CERTIFICATE OF CORRECTION (continued)
U.S. Pat. No. 11,603,369 B2

Page 5 of 5

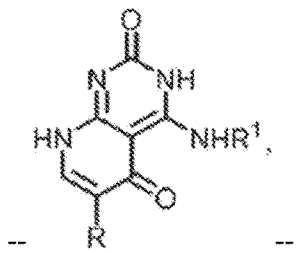
-- R --

13. Column 53, Line 55, Claim 15, delete "S [CH₂CH₂]ₛ," and insert -- S[CH₂CH₂]ₛ --

14. Column 54, Lines 30-38, Claim 19, delete " 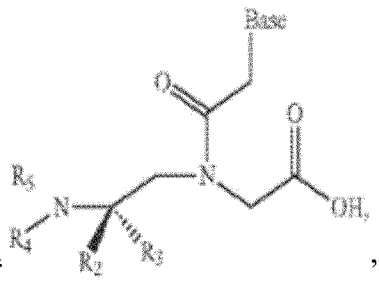 " and insert

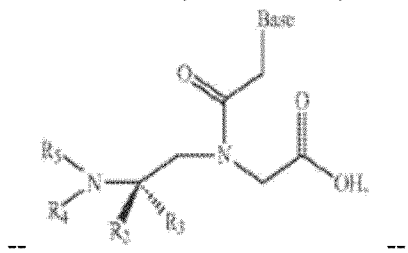
-- --

15. Column 54, Line 51, Claim 19, delete "S [CH₂CH₂]ₛ," and insert -- S[CH₂CH₂]ₛ --